US009115053B2

(12) United States Patent
Tsai et al.

(10) Patent No.: US 9,115,053 B2
(45) Date of Patent: Aug. 25, 2015

(54) ACTIVATORS OF CLASS I HISTONE DEACETLYASES (HDACS) AND USES THEREOF

(75) Inventors: Li-Huei Tsai, Cambridge, MA (US); Ling Pan, Charlestown, MA (US); Stephen J. Haggarty, Dorchester, MA (US); Debasis Patnaik, Quincy, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 73 days.

(21) Appl. No.: 13/554,670

(22) Filed: Jul. 20, 2012

(65) Prior Publication Data
US 2013/0096129 A1 Apr. 18, 2013

Related U.S. Application Data

(60) Provisional application No. 61/510,885, filed on Jul. 22, 2011.

(51) Int. Cl.
| C07D 487/04 | (2006.01) |
| C07C 219/28 | (2006.01) |
| C07D 307/52 | (2006.01) |
| C07D 405/12 | (2006.01) |
| C07D 409/12 | (2006.01) |
| C07C 217/58 | (2006.01) |
| C07D 411/12 | (2006.01) |
| C07D 307/40 | (2006.01) |

(52) U.S. Cl.
CPC ............. *C07C 219/28* (2013.01); *C07C 217/58* (2013.01); *C07D 307/40* (2013.01); *C07D 307/52* (2013.01); *C07D 405/12* (2013.01); *C07D 409/12* (2013.01); *C07D 411/12* (2013.01); *C07D 487/04* (2013.01)

(58) Field of Classification Search
CPC .................................................... C07D 487/04
USPC ........................................................ 544/184
See application file for complete search history.

(56) References Cited

U.S. PATENT DOCUMENTS

| 3,939,253 A | 2/1976 | Bodor et al. |
| 3,998,799 A | 12/1976 | Bodor et al. |

(Continued)

FOREIGN PATENT DOCUMENTS

| EP | 0 263 438 A2 | 4/1988 |
| WO | WO 93/07148 A1 | 4/1993 |

(Continued)

OTHER PUBLICATIONS

Vippagunta, et al. Advanced Drug Delivery Reviews 48 (2001) 3-26.*

(Continued)

*Primary Examiner* — Shawquia Jackson
(74) *Attorney, Agent, or Firm* — Wolf, Greenfield & Sacks, P.C.

(57) ABSTRACT

The present invention provides compounds of Formulae (A), (B), (C), and (D), pharmaceutically acceptable salts, solvates, hydrates, polymorphs, co-crystals, tautomers, stereoisomers, isotopically labeled derivatives, and prodrugs thereof, pharmaceutical compositions thereof, and kits thereof. The present invention further provides methods of using the compounds to treat or prevent neurological disorders. In one aspect, the methods include administering to a subject in need of treatment for a neurological disorder a therapeutically effective amount of DAC-001, DAC-002, DAC-003, DAC-009, or DAC-012, or a compound of Formula (A), (B), (C), or (D).

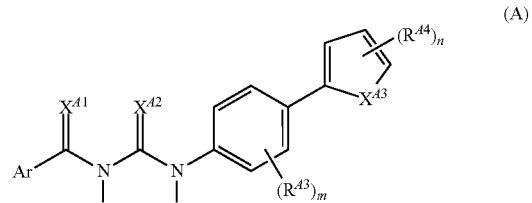

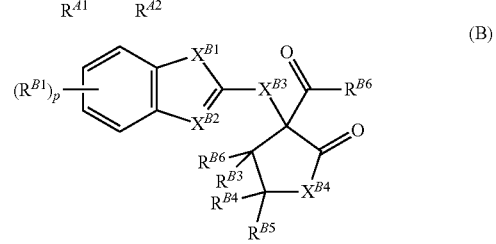

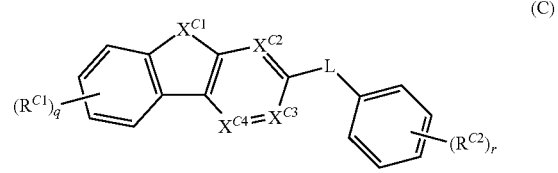

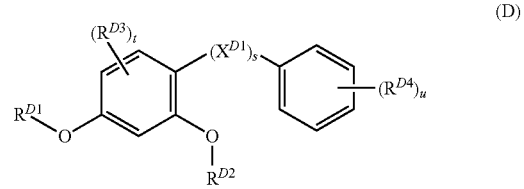

12 Claims, 12 Drawing Sheets

(56) References Cited

U.S. PATENT DOCUMENTS

| | | |
|---|---|---|
| 4,035,507 A | 7/1977 | Bodor et al. |
| 4,086,265 A | 4/1978 | Dodson et al. |
| 4,125,519 A | 11/1978 | Goodman et al. |
| 4,270,537 A | 6/1981 | Romaine |
| 4,596,556 A | 6/1986 | Morrow et al. |
| 4,617,316 A | 10/1986 | Plummer |
| 4,790,824 A | 12/1988 | Morrow et al. |
| 4,886,499 A | 12/1989 | Cirelli et al. |
| 4,940,460 A | 7/1990 | Casey et al. |
| 4,941,880 A | 7/1990 | Burns |
| 5,011,976 A | 4/1991 | Wuts |
| 5,013,756 A | 5/1991 | Follet et al. |
| 5,015,235 A | 5/1991 | Crossman |
| 5,025,036 A | 6/1991 | Carson et al. |
| 5,047,421 A | 9/1991 | Green |
| 5,064,413 A | 11/1991 | Mckinnon et al. |
| 5,102,906 A | 4/1992 | Nakayama et al. |
| 5,141,496 A | 8/1992 | Dalto et al. |
| 5,190,521 A | 3/1993 | Hubbard et al. |
| 5,236,952 A | 8/1993 | Bernauer et al. |
| 5,284,656 A | 2/1994 | Platz et al. |
| 5,312,335 A | 5/1994 | Mckinnon et al. |
| 5,328,483 A | 7/1994 | Jacoby |
| 5,334,144 A | 8/1994 | Alchas et al. |
| 5,339,163 A | 8/1994 | Homma et al. |
| 5,362,733 A | 11/1994 | Backstrom et al. |
| 5,383,851 A | 1/1995 | Mckinnon et al. |
| 5,389,653 A | 2/1995 | Bernauer et al. |
| 5,417,662 A | 5/1995 | Hjertman et al. |
| 5,430,038 A | 7/1995 | Martin et al. |
| 5,430,176 A | 7/1995 | Wuts |
| 5,451,569 A | 9/1995 | Wong et al. |
| 5,466,220 A | 11/1995 | Brenneman |
| 5,476,875 A | 12/1995 | Bernauer et al. |
| 5,480,381 A | 1/1996 | Weston |
| 5,489,614 A | 2/1996 | Korkolainen et al. |
| 5,503,627 A | 4/1996 | Mckinnon et al. |
| 5,520,639 A | 5/1996 | Peterson et al. |
| 5,525,727 A | 6/1996 | Bodor |
| 5,527,288 A | 6/1996 | Gross et al. |
| 5,569,189 A | 10/1996 | Parsons |
| 5,599,302 A | 2/1997 | Lilley et al. |
| 5,614,346 A | 3/1997 | Adel et al. |
| 5,618,803 A | 4/1997 | Bodor |
| 5,633,371 A | 5/1997 | Bernauer et al. |
| 5,649,912 A | 7/1997 | Peterson |
| 5,704,911 A | 1/1998 | Parsons |
| 5,893,397 A | 4/1999 | Peterson et al. |
| 5,993,412 A | 11/1999 | Deily et al. |
| 6,150,412 A | 11/2000 | Pystynen et al. |
| 6,320,078 B1 | 11/2001 | Suzuki et al. |
| 6,407,137 B2 | 6/2002 | Shashoua |
| 6,613,762 B2 | 9/2003 | Cai et al. |
| 7,119,074 B2 | 10/2006 | Ekwuribe et al. |
| 7,528,280 B2 | 5/2009 | Danda et al. |
| 8,088,951 B2 | 1/2012 | Tsai et al. |
| 8,263,547 B2 | 9/2012 | Tsai et al. |
| 2004/0077591 A1 | 4/2004 | Dangond |
| 2004/0087657 A1 | 5/2004 | Richon et al. |
| 2005/0037992 A1 | 2/2005 | Lyons et al. |
| 2006/0008517 A1 | 1/2006 | Lynch et al. |
| 2006/0018921 A1 | 1/2006 | Levenson et al. |
| 2006/0025337 A1 | 2/2006 | Sinclair et al. |
| 2006/0258694 A1 | 11/2006 | Bressi et al. |
| 2007/0015183 A1 | 1/2007 | Krainc |
| 2007/0078083 A1 | 4/2007 | Barlow et al. |
| 2007/0129331 A1 | 6/2007 | Gately et al. |
| 2008/0119434 A1 | 5/2008 | Gu et al. |
| 2008/0188457 A1 | 8/2008 | Barlow et al. |
| 2008/0300205 A1 | 12/2008 | Tsai et al. |
| 2010/0015130 A1 | 1/2010 | Tsai et al. |
| 2010/0075926 A1 | 3/2010 | Tsai et al. |
| 2011/0009475 A1 | 1/2011 | Fischer et al. |
| 2011/0218155 A1 | 9/2011 | Walensky et al. |
| 2011/0224303 A1 | 9/2011 | Tsai et al. |
| 2012/0039909 A1 | 2/2012 | Tsai et al. |
| 2012/0101147 A1 | 4/2012 | Tsai et al. |
| 2012/0322879 A1 | 12/2012 | Tsai et al. |
| 2013/0004517 A1 | 1/2013 | Tsai et al. |

FOREIGN PATENT DOCUMENTS

| | | |
|---|---|---|
| WO | WO 95/05169 A1 | 2/1995 |
| WO | WO 97/13537 A1 | 4/1997 |
| WO | WO 97/37705 A1 | 10/1997 |
| WO | WO 99/34850 A1 | 7/1999 |
| WO | WO 03/053336 A2 | 7/2003 |
| WO | WO 2006/001665 A1 | 1/2006 |
| WO | WO 2006/009373 A1 | 1/2006 |
| WO | WO 2007/049262 A1 | 5/2007 |
| WO | WO 2007/055942 A2 | 5/2007 |
| WO | WO 2007/100657 A2 | 9/2007 |
| WO | WO 2007/127137 A2 | 11/2007 |
| WO | WO 2007/136605 A2 | 11/2007 |
| WO | WO 2008/008472 A2 | 1/2008 |
| WO | WO 2008/011083 A2 | 1/2008 |
| WO | WO 2010/011318 A2 | 1/2010 |
| WO | WO 2010/065117 A1 | 6/2010 |

OTHER PUBLICATIONS

Walensky, et al. Document No. 152:470389, retrieved from CAPLUS; Apr. 16, 2010.*

Williems, et al. Document No. 141:157140, retrieved from CAPLUS; Jul. 29, 2004.*

Cecil Textbook of Medicine, 20th edition (1996), vol. 2, pp. 2050-2057.*

Cecil Textbook of Medicine, 20th edition (1996), vol. 2, pp. 1992-1996.*

FDA mulls drug to slow late-stage Alzheimer's [online], [retrieved on Sep. 23, 2003]. Retrieved from the Internet, URL; http:llwww.cnn.com120031HEALTHlconditionsl091241alzheimers.drug.aplindexhtml>.*

Hahnen et al., Histone deacetylase inhibitors: possible implications for neurodegenerative disorders. *Expert Opin Investig Drugs*. Feb. 2008;17(2):169-84. doi: 10.1517/13543784.17.2.169.

International Preliminary Report on Patentability for PCT/US2012/047609, mailed on Feb. 6, 2014.

Extended European Search Report for EP 09800677.8, mailed Aug. 10, 2012.

International Preliminary Report on Patentability for PCT/US2009/004267, mailed Feb. 3, 2011.

International Search Report and Written Opinion for PCT/US2009/04267, mailed Jan. 14, 2010.

Invitation to Pay Additional Fees for PCT/US2009/04267, mailed Nov. 3, 2009.

Invitation to Pay Additional Fees for PCT/US2012/047609, mailed Nov. 7, 2012.

International Search Report and Written Opinion for PCT/US2012/047609, mailed Feb. 12, 2013.

Genbank Submission; NCBI, Accession No. NM_004964; Janzer et al.; Sep. 2, 2012.

[No Author Listed] Deferoxamine. http://en.wikipedia.org/wiki/Deferoxamine. Accessed Jun. 30, 2008. 1 page.

Abuchowski et al., Soluble polymer-enzyme adducts. In Enzymes as Drugs. Hocenberg et al., eds. Wiley-Interscience. New York, NY. 367-83.

Adamec et al., DNA strand breaks in Alzheimer's disease. Brain Res. Dec. 4, 1999;849(1-2):67-77.

Adjei et al., Bioavailability of leuprolide following intratracheal administration to beagle dogs. Int J Pharmac. Jun. 11, 1990;61(1-2):135-44.

Adjei et al., Pulmonary delivery of peptide drugs: effect of particle size on bioavailability of leuprolide acetate in healthy male volunteers. Pharm Res. Jun. 1990;7(6):565-9.

Ahlijanian et al., Hyperphosphorylated tau and neurofilament and cytoskeletal disruptions in mice overexpressing human p25, an activator of cdk5. Proc Natl Acad Sci U S A. Mar. 14, 2000;97(6):2910-5.

(56) References Cited

OTHER PUBLICATIONS

Alkire, Hypothesis: Supression of memory protein formation underlies anesthetic-induced amnesia. Anesthesiology. 2008;109:768-70.

Al-Ubaidi et al., Photoreceptor degeneration induced by the expression of simian virus 40 large tumor antigen in the retina of transgenic mice. Proc Natl Acad Sci U S A. Feb. 15, 1992;89(4):1194-8.

Andegeko et al., Nuclear retention of ATM at sites of DNA double strand breaks. J Biol Chem. Oct. 12, 2001;276(41):38224-30. Epub Jul. 13, 2001.

Andorfer et al., Cell-cycle reentry and cell death in transgenic mice expressing nonmutant human tau isoforms. J Neurosci. Jun. 1, 2005;25(22):5446-54.

Bates, Huntington's disease. Exploiting expression. Nature. Oct. 18, 2001;413(6857):691, 693-4.

Berge et al., Pharmaceutical salts. J Pharm Sci. Jan. 1977;66(1):1-19.

Bian et al., Axonopathy, tau abnormalities, and dyskinesia, but no neurofibrillary tangles in p25-transgenic mice. J Comp Neurol. May 6, 2002;446(3):257-66.

Boutillier et al., Constitutive repression of E2F1 transcriptional activity through HDAC proteins is essential for neuronal survival. Ann N Y Acad Sci. Nov. 2002;973:438-42.

Boutillier et al., Selective E2F-dependent gene transcription is controlled by histone deacetylase activity during neuronal apoptosis. J Neurochem. Feb. 2003;84(4):814-28.

Bradshaw et al., Fluctuating cognition in dementia with Lewy bodies and Alzheimer's disease is qualitatively distinct. J Neurol Neurosurg Psychiatry. Mar. 2004;75(3):382-7.

Braquet et al., Effect of endothelin-1 on blood pressure and bronchopulmonary system of the guinea pig. J Cardiovascular Pharmacol. 1989;13(Suppl. 5):S143-6.

Bredy et al., The histone deacetylase inhibitor valproic acid enhances acquisition, extinction, and reconsolidation of conditioned fear. Learn Mem. Jan. 3, 2008;15(1):39-45. Print Jan. 2008.

Brehm et al., Retinoblastoma protein recruits histone deacetylase to repress transcription. Nature. Feb. 5, 1998;391(6667):597-601.

Busser et al., Ectopic cell cycle proteins predict the sites of neuronal cell death in Alzheimer's disease brain. J Neurosci. Apr. 15, 1998;18(8):2801-7.

Cardin et al., Memory suppressor genes: enhancing the relationship between synaptic plasticity and memory storage. J Neurosci Res. 1999;58:10-23.

Cerna et al., Histone deacetylation as a target for radiosensitization. Curr Top Dev Biol. 2006;73:173-204.

Cheung et al., Synaptic roles of Cdk5: implications in higher cognitive functions and neurodegenerative diseases. Neuron. Apr. 6, 2006;50(1):13-8.

Citrome, Schizophrenia and valproate. Psychopharmacol Bull. 2003;37 Suppl 2:74-88.

Colangelo, The recovered memory controversy: a representative case study. J Child Sex Abus. Jan.-Feb. 2009;18(1):103-21.

Cruz et al., A Jekyll and Hyde kinase: roles for Cdk5 in brain development and disease. Curr Opin Neurobiol. Jun. 2004;14(3):390-4.

Cruz et al., Aberrant Cdk5 activation by p25 triggers pathological events leading to neurodegeneration and neurofibrillary tangles. Neuron. Oct. 30, 2003;40(3):471-83.

De Ruijter et al., Histone deacetylases (HDACs): characterization of the classical HDAC family. Biochem J. Mar. 15, 2003;370(Pt 3):737-49.

Debs et al., Lung-specific delivery of cytokines induces sustained pulmonary and systemic immunomodulation in rats. J Immunol. May 15, 1988;140(10):3482-8.

Dhavan et al., A decade of CDK5. Nat Rev Mol Cell Biol. Oct. 2001;2(10):749-59.

Dhawan et al., The effect of smoking and eating habits on DNA damage in Indian population as measured in the Comet assay. Mutat Res. Mar. 1, 2001;474(1-2):121-8.

Eliseeva et al., Characterization of novel inhibitors of histone acetyltransferases. Mol Cancer Ther. Sep. 2007;6(9):2391-8.

Ferrante et al., Evidence of increased oxidative damage in both sporadic and familial amyotrophic lateral sclerosis. J Neurochem. Nov. 1997;69(5):2064-74.

Fischer et al., Opposing roles of transient and prolonged expression of p25 in synaptic plasticity and hippocampus-dependent memory. Neuron. Dec. 8, 2005;48(5):825-38.

Fischer et al., Recovery of learning and memory is associated with chromatin remodelling. Nature. May 10, 2007;447(7141):178-82. Epub Apr. 29, 2007.

Frankland et al., The involvement of the anterior cingulate cortex in remote contextual fear memory. Science. May 7, 2004;304(5672):881-3.

Galasinski et al., Phosphatase inhibition leads to histone deacetylases 1 and 2 phosphorylation and disruption of corepressor interactions. J Biol Chem. May 31, 2002;277(22):19618-26. Epub Mar. 27, 2002.

García-Bonilla et al., Calpain-induced proteolysis after transient global cerebral ischemia and ischemic tolerance in a rat model. Neurochem Res. Dec. 2006;31(12):1433-41. Epub Nov. 7, 2006.

Geraerts et al., Forgetting unwanted memories: directed forgetting and thought suppression methods. Acta Psychol (Amst). Mar. 2008;127(3):614-22. Epub Feb. 14, 2008.

Gilmore et al., Neocortical cell migration: GABAergic neurons and cells in layers I and VI move in a cyclin-dependent kinase 5-independent manner. J Neurosci. Dec. 15, 2001;21(24):9690-700.

Gobbel et al., Response of postmitotic neurons to X-irradiation: implications for the role of DNA damage in neuronal apoptosis. J Neurosci. Jan. 1, 1998;18(1):147-55.

Gojo et al., Phase 1 and pharmacologic study of MS-275, a histone deacetylase inhibitor, in adults with refractory and relapsed acute leukemias. Blood. Apr. 1, 2007;109(7):2781-90.

Gould et al., Emerging experimental therapeutics for bipolar disorder: insights from the molecular and cellular actions of current mood stabilizers. Mol Psychiatry. Aug. 2004;9(8):734-55.

Gould et al., Signaling networks in the pathophysiology and treatment of mood disorders. J Psychosom Res. Aug. 2002;53(2):687-97.

Guan et al., HDAC2 negatively regulates memory formation and synaptic plasticity. Nature. May 7, 2009;459(7243):55-60.

Guenther et al., Assembly of the SMRT-histone deacetylase 3 repression complex requires the TCP-1 ring complex. Genes Dev. Dec. 15, 2002;16(24):3130-5.

Gui et al., Histone deacetylase (HDAC) inhibitor activation of p21WAF1 involves changes in promoter-associated proteins, including HDAC1. Proc Natl Acad Sci U S A. Feb. 3, 2004;101(5):1241-6. Epub Jan. 20, 2004.

Hamilton et al., Does oxidative damage to DNA increase with age? Proc Natl Acad Sci U S A. Aug. 28, 2001;98(18):10469-74. Epub Aug. 21, 2001.

Hauser et al., Activation of the mouse histone deacetylase 1 gene by cooperative histone phosphorylation and acetylation. Mol Cell Biol. Nov. 2002;22(22):7820-30.

Hayashi et al., Oxidative damage and breakage of DNA in rat brain after transient MCA occlusion. Brain Res. Jun. 19, 1999;832(1-2):159-63.

Hayashi et al., Phosphorylation of retinoblastoma protein in rat brain after transient middle cerebral artery occlusion. Neuropathol Appl Neurobiol. Aug. 2000;26(4):390-7.

Herrup et al., The induction of multiple cell cycle events precedes target-related neuronal death. Development. Aug. 1995;121(8):2385-95.

Hockly et al., Suberoylanilide hydroxamic acid, a histone deacetylase inhibitor, ameliorates motor deficits in a mouse model of Huntington's disease. Proc Natl Acad Sci U S A. Feb. 18, 2003;100(4):2041-6. Epub Feb. 7, 2003.

Horn et al., Neural network modeling of memory deterioration in Alzheimer's disease. Neural Computation. 1993;5:736-49.

Horn et al., Neuronal-based synaptic compensation: a computational study in Alzheimer's disease. Neural Comput. Aug. 15, 1996;8(6):1227-43.

Hu et al., Identification of novel isoform-selective inhibitors within class I histone deacetylases. J Pharmacol Exp Ther. Nov. 2003;307(2):720-8. Epub Sep. 15, 2003.

(56) References Cited

OTHER PUBLICATIONS

Hubbard et al., Anti-neutrophil-elastase defenses of the lower respiratory tract in alpha 1-antitrypsin deficiency directly augmented with an aerosol of alpha 1-antitrypsin. Ann Intern Med. Aug. 1, 1989;111(3):206-12.

Iavarone et al., E2F and histone deacetylase mediate transforming growth factor beta repression of cdc25A during keratinocyte cell cycle arrest. Mol Cell Biol. Jan. 1999;19(1):916-22.

Ishdorj et al., Lysophosphatidic acid protects cancer cells from histone deacetylase (HDAC) inhibitor-induced apoptosis through activation of HDAC. J Biol Chem. Jun. 13, 2008;283(24):16818-29. Epub Apr. 11, 2008.

Ishizuka et al., The N-CoR/histone deacetylase 3 complex is required for repression by thyroid hormone receptor. Mol Cell Biol. Aug. 2003;23(15):5122-31.

Johannessen et al., Valproate: past, present, and future. CNS Drug Rev. 2003 Summer;9(2):199-216.

Kang et al. Neuroprotective effects of naturally occurring biflavonoids. Bioorg Med Chem Lett. Aug. 1, 2005;15(15):3588-91.

Kim et al., Deregulation of HDAC1 by p25/Cdk5 in neurotoxicity. Neuron. Dec. 10, 2008;60(5):803-17.

Kim et al., Inhibition of histone deacetylation enhances the neurotoxicity induced by the C-terminal fragments of amyloid precursor protein. J Neurosci Res. Jan. 1, 2004;75(1):117-24.

Kim et al., Modality-specific retrograde amnesia of fear. Science. May 1, 1992;256(5057):675-7.

Kim et al., SIRT1 deacetylase protects against neurodegeneration in models for Alzheimer's disease and amyotrophic lateral sclerosis. EMBO J. Jul. 11, 2007;26(13):3169-79. Epub Jun. 21, 2007.

Klein et al., The harlequin mouse mutation downregulates apoptosis-inducing factor. Nature. Sep. 26, 2002;419(6905):367-74.

Konishi et al., Cdc2 phosphorylation of BAD links the cell cycle to the cell death machinery. Mol Cell. May 2002;9(5):1005-16.

Konishi et al., The E2F-Cdc2 cell-cycle pathway specifically mediates activity deprivation-induced apoptosis of postmitotic neurons. J Neurosci. Mar. 1, 2003;23(5):1649-58.

Korzus et al., CBP histone acetyltransferase activity is a critical component of memory consolidation. Neuron. Jun. 24, 2004;42(6):961-72.

Kouzarides, Histone acetylases and deacetylases in cell proliferation. Opin Genet Dev. Feb. 1999;9(1):40-8.

Kruman et al., Cell cycle activation linked to neuronal cell death initiated by DNA damage. Neuron. Feb. 19, 2004;41(4):549-61.

Lagger et al., Essential function of histone deacetylase 1 in proliferation control and CDK inhibitor repression. EMBO J. Jun. 3, 2002;21(11):2672-81.

Langer, New methods of drug delivery. Science. Sep. 28, 1990;249(4976):1527-33.

Langley et al., Remodeling chromatin and stress resistance in the central nervous system: histone deacetylase inhibitors as novel and broadly effective neuroprotective agents. Curr Drug Targets CNS Neurol Disord. Feb. 2005;4(1):41-50.

Lee et al., Neurotoxicity induces cleavage of p35 to p25 by calpain. Nature. May 18, 2000;405(6784):360-4.

Levenson et al., Regulation of histone acetylation during memory formation in the hippocampus. J Biol Chem. Sep. 24, 2004;279(39):40545-59. Epub Jul. 23, 2004.

Levy et al., Individual differences in the suppression of unwanted memories: the executive deficit hypothesis. Acta Psychologica. 2008;127:623-35.

Liu et al., Regulation of neuron survival and death by p130 and associated chromatin modifiers. Genes Dev. Mar. 15, 2005;19(6):719-32.

Liu et al., Regulation of neuronal survival and death by E2F-dependent gene repression and derepression. Neuron. Nov. 8, 2001;32(3):425-38.

Lu et al., Gene regulation and DNA damage in the ageing human brain. Nature. Jun. 24, 2004;429(6994):883-91. Epub Jun. 9, 2004.

Manji et al., The underlying neurobiology of bipolar disorder. World Psychiatry. Oct. 2003;2(3):136-46.

Mao et al., Disrupted in schizophrenia 1 regulates neuronal progenitor proliferation via modulation of GSK3beta/beta-catenin signaling. Cell. Mar. 20, 2009;136(6):1017-31.

McCampbell et al., Histone deacetylase inhibitors reduce polyglutamine toxicity. Proc Natl Acad Sci U S A. Dec. 18, 2001;98(26):15179-84. Epub Dec. 11, 2001.

McShea et al., Neuronal cell cycle re-entry mediates Alzheimer disease-type changes. Biochim Biophys Acta. Apr. 2007;1772(4):467-72. Epub Oct. 3, 2006.

Methot et al., Exploration of the internal cavity of histone deacetylase (HDAC) with selective HDAC1/HDAC2 inhibitors (SHI-1:2). Bioorg Med Chem Lett. Feb. 1, 2008;18(3):973-8. Epub Jan. 7, 2008.

Mitsios et al., Expression of cyclin-dependent kinase 5 mRNA and protein in the human brain following acute ischemic stroke. Brain Pathol. Jan. 2007;17(1):11-23.

Monfils et al., Extinction-reconsolidation boundaries: key to persistent attenuation of fear memories. Science. May 15, 2009;324(5929):951-5. Epub Apr. 2, 2009.

Morrison et al., Neuroprotection by histone deacetylase-related protein. Mol Cell Biol. May 2006;26(9):3550-64.

Nagy et al., Nuclear receptor repression mediated by a complex containing SMRT, mSin3A, and histone deacetylase. Cell. May 2, 1997;89(3):373-80.

Nakazawa et al., Synthesis of Ring-substituted flavonoids and allied compounds. Chem. Pharma. Bulletin. 1963;11:283-288.

Need et al., Handling and environmental enrichment do not rescue learning and memory impairments in alphaCamKII(T286A) mutant mice. Genes Brain Behav. Jun. 2003;2(3):132-9.

Neugebauer et al., Inhibitors of NAD+ dependent histone deacetylases (sirtuins). Curr Pharm Des. 2008;14(6):562-73.

Newmark et al., Preparation and properties of adducts of streptokinase-plasmin complex with polyethylene glycol and pluronic polyol F38. J Appl Biochem. 1982;4:185-9.

Ng et al., Histone deacetylases: silencers for hire. Trends Biochem Sci. Mar. 2000;25(3):121-6.

Nguyen et al., Cycling at the interface between neurodevelopment and neurodegeneration. Cell Death Differ. Dec. 2002;9(12):1294-306.

Nguyen et al., Deregulation of Cdk5 in a mouse model of ALS: toxicity alleviated by perikaryal neurofilament inclusions. Neuron. Apr. 2001;30(1):135-47.

Nithianantharajah et al., Enriched environments, experience-dependent plasticity and disorders of the nervous system. Nat Rev Neurosci. Sep. 2006;7(9):697-709.

Nouspikel et al., Terminally differentiated human neurons repair transcribed genes but display attenuated global DNA repair and modulation of repair gene expression. Mol Cell Biol. Mar. 2000;20(5):1562-70.

Nouspikel et al., When parsimony backfires: neglecting DNA repair may doom neurons in Alzheimer's disease. Bioessays. Feb. 2003;25(2):168-73.

Ohshima et al., Impairment of hippocampal long-term depression and defective spatial learning and memory in p35 mice. J Neurochem. Aug. 2005;94(4):917-25. Epub Jun. 30, 2005.

Oswein et al., Aerosolization of proteins. Proceedings of Symposium on Respiratory Drug Delivery II. Keystone, Colorado. Mar. 1990.

Padmanabhan et al., Role of cell cycle regulatory proteins in cerebellar granule neuron apoptosis. J Neurosci. Oct. 15, 1999;19(20):8747-56.

Palop et al., A network dysfunction perspective on neurodegenerative diseases. Nature. Oct. 19, 2006;443(7113):768-73.

Patrick et al., Conversion of p35 to p25 deregulates Cdk5 activity and promotes neurodegeneration. Nature. Dec. 9, 1999;402(6762):615-22.

Peng et al., ADAR2-dependent RNA editing of AMPA receptor subunit GluR2 determines vulnerability of neurons in forebrain ischemia. Neuron. Mar. 2, 2006;49(5):719-33.

Pflum et al., Histone deacetylase 1 phosphorylation promotes enzymatic activity and complex formation. J Biol Chem. Dec. 14, 2001;276(50):47733-41. Epub Oct. 15, 2001.

Rampon et al., Effects of environmental enrichment on gene expression in the brain. Proc Natl Acad Sci U S A. Nov. 7, 2000;97(23):12880-4.

(56) References Cited

OTHER PUBLICATIONS

Rashidian et al., Cell cycle machinery and stroke. Biochim Biophys Acta. Apr. 2007;1772(4):484-93. Epub Dec. 5, 2006.

Rayman et al., E2F mediates cell cycle-dependent transcriptional repression in vivo by recruitment of an HDAC1/mSin3B corepressor complex. Genes Dev. Apr. 15, 2002;16(8):933-47.

Robison et al., DNA damage and chronic neuronal degenerations. J Neurol Sci. Apr. 1984;64(1):11-20.

Rolig et al., Linking DNA damage and neurodegeneration. Trends Neurosci. Sep. 2000;23(9):417-24.

Roth et al., Histone acetyltransferases. Annu Rev Biochem. 2001;70:81-120.

Salminen et al., Neuronal apoptosis induced by histone deacetylase inhibitors. Brain Res Mol Brain Res. Oct. 30, 1998;61(1-2):203-6.

Sancar et al., Molecular mechanisms of mammalian DNA repair and the DNA damage checkpoints. Annu Rev Biochem. 2004;73:39-85.

Santacruz et al., Tau suppression in a neurodegenerative mouse model improves memory function. Science. Jul. 15, 2005;309(5733):476-81.

Sassone-Corsi et al., Requirement of Rsk-2 for epidermal growth factor-activated phosphorylation of histone H3. Science. Aug. 6, 1999;285(5429):886-91.

Schiller et al., Preventing the return of fear in humans using reconsolidation update mechanisms. Nature. Jan. 7, 2010;463(7277):49-53. Epub Dec. 9, 2009.

Schnurr et al., Cognitive behavioral therapy for posttraumatic stress disorder in women: a randomized controlled trial. JAMA. Feb. 28, 2007;297(8):820-30.

Smith et al., Cyclin-dependent kinase 5 is a mediator of dopaminergic neuron loss in a mouse model of Parkinson's disease. Proc Natl Acad Sci U S A. Nov. 11, 2003;100(23):13650-5. Epub Oct. 31, 2003.

Smith et al., Pulmonary deposition and clearance of aerosolized alpha-l-proteinase inhibitor administered to dogs and to sheep. J Clin Invest. Oct. 1, 1989;84(4):1145-6.

Stadler et al., Histone deacetylase 1 is required for cell cycle exit and differentiation in the zebrafish retina. Dev Dyn. Jul. 2005;233(3):883-9.

Steffan et al., Histone deacetylase inhibitors arrest polyglutamine-dependent neurodegeneration in *Drosophila*. Nature. Oct. 18, 2001;413(6857):739-43.

Sterner et al., Acetylation of histones and transcription-related factors. Microbiol Mol Biol Rev. Jun. 2000;64(2):435-59.

Stiegler et al., The COOH-terminal region of pRb2/p130 binds to histone deacetylase 1 (HDAC1), enhancing transcriptional repression of the E2F-dependent cyclin A promoter. Cancer Res. Nov. 15, 1998;58(22):5049-52.

Swatton et al., Increased MAP kinase activity in Alzheimer's and Down syndrome but not in schizophrenia human brain. Eur J Neurosci. May 2004;19(10):2711-9.

Sweatt, Behavioural neuroscience: Down memory lane. Nature. May 10, 2007;447(7141):151-2.

Tang et al., Differential effects of enrichment on learning and memory function in NR2B transgenic mice. Neuropharmacology. Nov. 2001;41(6):779-90.

Taunton et al., A mammalian histone deacetylase related to the yeast transcriptional regulator Rpd3p. Science. Apr. 19, 1996;272(5260):408-11.

Tsankova et al., Sustained hippocampal chromatin regulation in a mouse model of depression and antidepressant action. Nat Neurosci. Apr. 2006;9(4):519-25. Epub Feb. 26, 2006.

Van Praag et al., Neural consequences of environmental enrichment. Nat Rev Neurosci. Dec. 2000;1(3):191-8.

Vidal et al., RPD3 encodes a second factor required to achieve maximum positive and negative transcriptional states in *Saccharomyces cerevisiae*. Mol Cell Biol. Dec. 1991;11(12):6317-27.

Vincent et al., Mitotic mechanisms in Alzheimer's disease? J Cell Biol. Feb. 1996;132(3):413-25.

Voss et al., Possible axonal regrowth in late recovery from the minimally conscious state. J Clin Invest. Jul. 2006;116(7):2005-11.

Wade et al., Histone acetylation: chromatin in action. Trends Biochem Sci. Apr. 1997;22(4):128-32.

Wang et al., Cdk5 activation induces hippocampal CA1 cell death by directly phosphorylating NMDA receptors. Nat Neurosci. Oct. 2003;6(10):1039-47. Epub Sep. 21, 2003.

Wen et al., Cdk5 is involved in NFT-like tauopathy induced by transient cerebral ischemia in female rats. Biochim Biophys Acta. Apr. 2007;1772(4):473-83. Epub Oct. 18, 2006.

Wilen et al., Strategies in Optical Resolution. Tetrahedron. 1977;33:2725-36.

Wilen, Tables of Resolving Agents and Optical Resolutions. E.L. Eliel, ed. University of Notre Dame Press, Notre Dame, IN. 1972:268-98.

Yamaguchi et al., Histone deacetylase 1 regulates retinal neurogenesis in zebrafish by suppressing Wnt and Notch signaling pathways. Development. Jul. 2005;132(13):3027-43.

Yang et al., DNA replication precedes neuronal cell death in Alzheimer's disease. J Neurosci. Apr. 15, 2001;21(8):2661-8.

Zarate et al., Molecular mechanisms of bipolar disorder. Drug Disc Today: Disease Mech. 2005;2(4):435-45.

Zhu et al. Flavonoids possess neuroprotective effects on cultured pheochromocytoma PC12 cells: a comparison of different flavonoids in activating estrogenic effect and in preventing beta-amyloid-induced cell death. J Agric Food Chem. Mar. 21, 2007;55(6):2438-45. Epub Feb. 27, 2007.

Zhu et al., Activation of cAMP-response-element-binding protein (CREB) after focal cerebral ischemia stimulates neurogenesis in the adult dentate gyrus. Proc Natl Acad Sci U S A. Jun. 22, 2004;101(25):9453-7. Epub Jun. 14, 2004.

* cited by examiner

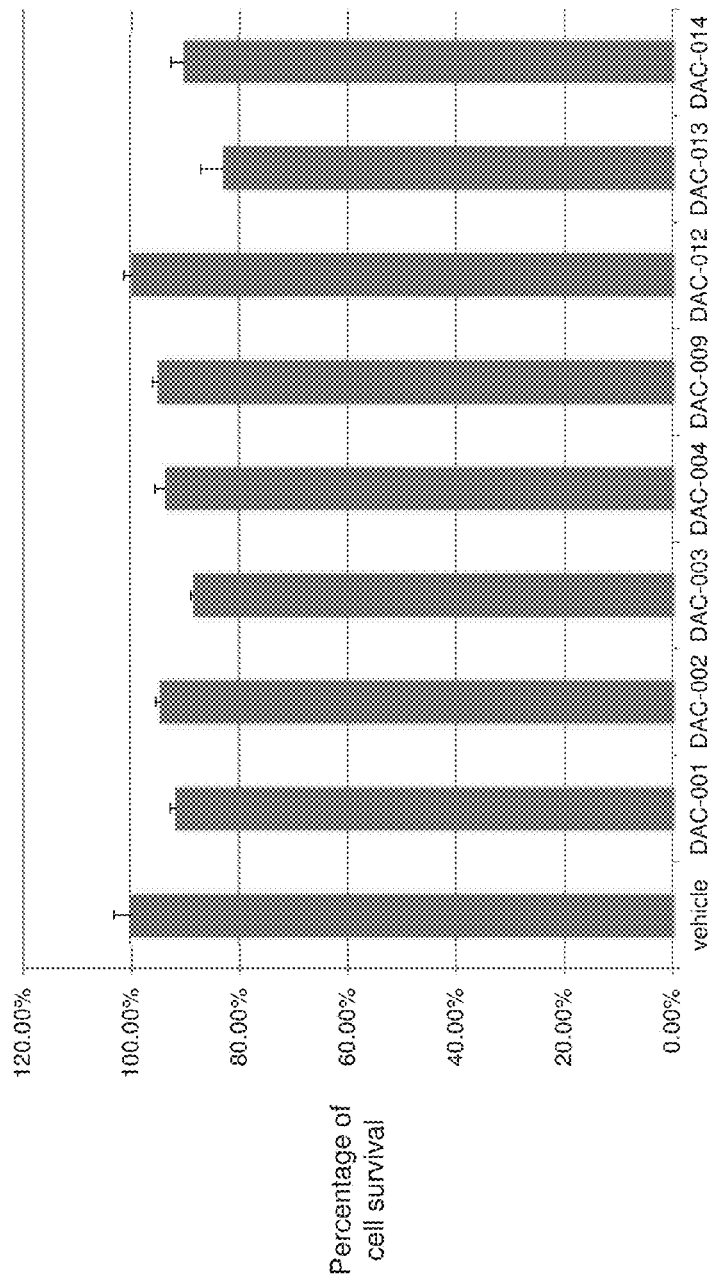

ACTIVATORS OF CLASS I HISTONE DEACETLYASES (HDACS) AND USES THEREOF

RELATED APPLICATIONS

The present application claims priority under 35 U.S.C. §119(e) to U.S. provisional application, U.S. Ser. No. 61/510,885, filed Jul. 22, 2011, which is incorporated herein by reference.

GOVERNMENT SUPPORT

This invention was made with U.S. Government support under grant number RC1-AG035711 awarded by the National Institutes of Health. Accordingly, the U.S. Government has certain rights in the invention.

FIELD OF THE INVENTION

The field of the invention pertains to activators of class I histone deacetylases and their uses in the treatment of neurological disorders.

BACKGROUND OF THE INVENTION

In a variety of neurodegenerative disorders such as ischemia and Alzheimer's disease (Hayashi et al., *Neuropathol. Appl. Neurobiol.* (2000) 26:390-97; Rashidian et al., *Biochim. Biophys. Acta.* (2007) 1772:484-93; Vincent et al., *J. Cell. Biol.* (1996) 132:413-25.; Yang et al., *J. Neurosci.* (2001) 21:2661-68), neurons engage in aberrant cell cycle activities, expressing cell cycle markers such as Ki-67 and PCNA, and undergoing a limited extent of DNA replication (Yang et al., *J. Neurosci.* (2001) 21:2661-68). This behavior is remarkable considering that neurons have terminally differentiated during development and remain quiescent for decades prior to the onset of these events. While the underlying mechanisms are poorly understood, multiple lines of evidence suggest that these activities play an early and contributory role in neuronal death (Andorfer et al., *J. Neurosci.* (2005) 25:5446-54; Busser et al., *J. Neurosci.* (1998) 18:2801-07; Herrup et al., *Development.* (1995) 121:2385-95; Nguyen et al., *Cell Death Differ.* (2002) 9:1294-306.). For example, overexpression of cell cycle activity-inducing proteins such as SV40 large T antigen, c-myc, c-Myb, or E2F-1 causes neuronal death in vitro and in vivo (al-Ubaidi et al., *Proc. Natl. Acad. Sci. USA* (1992) 89:1194-98.; Konishi et al., *J. Neurosci.* (2003) 23:1649-58; Liu et al., *Neuron.* (2001) 32:425-38; McShea et al., *Biochim. Biophys. Acta.* (2007) 1772:467-72), while pharmacological inhibitors of CDKs or other cell cycle components can exert neuroprotective effects (Padmanabhan et al., *J. Neurosci.* (1999) 19:8747-56).

DNA damage may also be involved in multiple conditions involving neuronal death (Adamec et al., *Brain Res.* (1999) 849:67-77; Ferrante et al., *J. Neurochem.* (1997) 69:2064-74; Hayashi et al., *Brain Res.* (1999) 832:159-63; Kruman et al., *Neuron.* (2004) 41:549-61; Robison et al., *J. Neurol. Sci.* (1984) 64:11-20). For example, oxidative damage to neuronal DNA has been observed in rodent models of ischemia (Hayashi et al., *Brain Res.* (1999) 832:159-63). Accumulation of reactive oxygen species results in DNA damage, cell cycle activity, and neurodegeneration in mutant mice with disrupted apoptosis-inducing factor (AIF) (Klein et al., *Nature* (2002) 419:367-74). In addition, congenital syndromes with DNA repair gene mutations, such as ataxia telangiectasia and Werner's syndrome, display a progressive neurodegeneration phenotype, demonstrating the importance of maintaining DNA integrity in the adult brain (Rolig et al., *Trends Neurosci.* (2000) 23:417-24). Importantly, DNA damage is involved in the aging of the human brain (Lu et al., *Nature* (2004) 429:883-91), which suggests that DNA damage may play a role in age-dependent neurological disorders as well.

Nucleosomes, the primary scaffold of chromatin folding, are dynamic macromolecular structures, influencing the conformation of chromatin in solution. The nucleosome core is made up of the histone proteins, H2A, H2B, H3 and H4. Histone acetylation causes nucleosomes and nucleosomal arrangements to behave with altered biophysical properties. The balance between the activities of histone acetyl transferases (HAT) and histone deacetylases (HDAC) determines the level of histone acetylation. Acetylated histones cause relaxation of chromatin and activation of gene transcription, whereas deacetylated chromatin generally is transcriptionally inactive.

HDACs have been grouped in four classes depending on sequence identity, domain organization, and function: Class I: HDAC1 (histone deacetylase 1), HDAC2, HDAC3, HDAC8; Class II: HDAC4, HDAC5, HDAC6, HDAC7, HDAC9, HDAC10; Class III: SIRT1, SIRT2, SIRT3, SIRT4, SIRT5, SIRT6, SIRT7; and Class IV: HDAC11. Within Class I, HDAC1, HDAC2 and HDAC8 are primarily found in the nucleus while HDAC3 and Class II HDACs can shuttle between the nucleus and the cytoplasm. Class III HDACs (the sirtuins), couple the removal of the acetyl group of the histone to NAD hydrolysis, thereby coupling the deacetylation reaction to the energy status of the cell.

A need remains for new compounds and treatment options that result in the protection of cells, including neuronal cells to DNA damage. The suppression of DNA damage in neuronal cells is an important mechanism for suppressing neuronal cell death and provides an opportunity for the treatment or prevention of various neurological disorders.

SUMMARY OF THE INVENTION

The present invention provides inventive compounds of the Formulae (A), (B), (C), and (D), pharmaceutically acceptable salts, solvates, hydrates, polymorphs, co-crystals, tautomers, stereoisomers, isotopically labeled derivatives, and prodrugs thereof, pharmaceutical compositions thereof, and kits thereof. The present invention further provides methods of using the inventive compounds, pharmaceutically acceptable salts, solvates, hydrates, polymorphs, co-crystals, tautomers, stereoisomers, isotopically labeled derivatives, and prodrugs thereof, pharmaceutical compositions thereof, and kits thereof, to study activation of class I histone deacetylase (HDAC) and as therapeutics, e.g., for the treatment of neurological disorders, such as Alzheimer's disease, Parkinson's disease, Huntington's disease, ALS (amyotrophic lateral sclerosis), traumatic brain injury, ischemic brain injury, stroke, frontal temporal dementia, Pick's disease, corticobasal degeneration, supra cerebral palsy, prion diseases (e.g., Creutzfeldt-Jakob disease, Gerstmann-Straussler-Scheinker syndrome, Fatal Familial Insomnia, and Kuru), Nieman Pick type C, spinal cerebellar ataxia, spinal muscular dystrophy, ataxia telangiectasia, hippocampal sclerosis, Cockayne syndrome, Werner syndrome, xeroderma pigmentosaum, and Bloom syndrome.

In one aspect, the invention provides compounds of Formula (A):

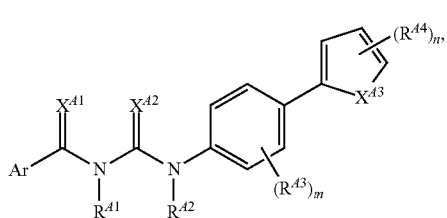

and pharmaceutically acceptable salts, solvates, hydrates, polymorphs, co-crystals, tautomers, stereoisomers, isotopically labeled derivatives, and prodrugs thereof, wherein each instance of $X^{A1}$, $X^{A2}$, and $X^{A3}$ is independently oxygen or sulfur;

each instance of $R^{A1}$ and $R^{A2}$ is independently hydrogen, a nitrogen protecting group, or $C_{1-6}$ alkyl;

Ar is optionally substituted aryl or optionally substituted heteroaryl;

each instance of $R^{A3}$ and $R^{A4}$ is independently selected from the group consisting of halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{A3a}$, —$N(R^{A3b})_2$, —$SR^{A3a}$, —$C(=O)R^{A3a}$, —$C(=O)OR^{A3a}$, —$C(=O)SR^{A3a}$, —$C(=O)N(R^{A3b})_2$, —$OC(=O)R^{A3a}$, —$OC(=O)OR^{A3a}$, —$OC(=O)SR^{A3a}$, —$OC(=O)N(R^{A3b})_2$, —$NR^{A3b}C(=O)R^{A3b}$, —$NR^{A3b}C(=O)OR^{A3a}$, —$NR^{A3b}C(=O)SR^{A3a}$, —$NR^{A3b}C(=O)N(R^{A3b})_2$, —$SC(=O)R^{A3a}$, —$SC(=O)OR^{A3a}$, —$SC(=O)SR^{A3a}$, —$SC(=O)N(R^{A3b})_2$, —$C(=NR^{A3b})R^{A3a}$, —$C(=NR^{A3b})OR^{A3a}$, —$C(=NR^{A3b})SR^{A3a}$, —$C(=NR^{A3b})N(R^{A3b})_2$, —$OC(=NR^{A3b})R^{A3a}$, —$OC(=NR^{A3b})OR^{A3a}$, —$OC(=NR^{A3b})SR^{A3a}$, —$OC(=NR^{A3b})N(R^{A3b})_2$, —$NR^{A3b}C(=NR^{A3b})R^{A3b}$, —$NR^{A3b}C(=NR^{A3b})OR^{A3a}$, —$NR^{A3b}C(=NR^{A3b})SR^{A3a}$, —$NR^{A3b}C(=NR^{A3b})N(R^{A3b})_2$, —$SC(=NR^{A3b})R^{A3a}$, —$SC(=NR^{A3b})OR^{A3a}$, —$SC(=NR^{A3b})SR^{A3a}$, —$SC(=NR^{A3b})N(R^{A3b})_2$, —$C(=S)R^{A3a}$, —$C(=S)OR^{A3a}$, —$C(=S)SR^{A3a}$, —$C(=S)N(R^{A3b})_2$, —$OC(=S)R^{A3a}$, —$OC(=S)OR^{A3a}$, —$OC(=S)SR^{A3a}$, —$OC(=S)N(R^{A3b})_2$, —$NR^{A3b}C(=S)R^{A3b}$, —$NR^{A3b}C(=S)OR^{A3a}$, —$NR^{A3b}C(=S)SR^{A3a}$, —$NR^{A3b}C(=S)N(R^{A3b})_2$, —$SC(=S)R^{A3a}$, —$SC(=S)OR^{A3a}$, —$SC(=S)SR^{A3a}$, —$SC(=S)N(R^{A3b})_2$, —$S(=O)R^{A3a}$, —$SO_2R^{A3a}$, —$NR^{A3b}SO_2R^{A3a}$, —$SO_2N(R^{A3b})_2$, —CN, —SCN, and —$NO_2$, wherein each occurrence of $R^{A3a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, and each occurrence of $R^{A3b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{A3b}$ groups are joined to form an optionally substituted heterocyclic ring;

m is 0, 1, 2, 3, or 4; and n is 0, 1, 2, or 3.

In another aspect, the invention provides compounds of Formula (B):

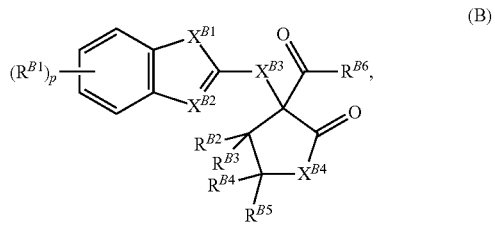

and pharmaceutically acceptable salts, solvates, hydrates, polymorphs, co-crystals, tautomers, stereoisomers, isotopically labeled derivatives, and prodrugs thereof, wherein each instance of $X^{B1}$, $X^{B3}$, and $X^{B4}$ is independently oxygen, sulfur, $NR^{B4a}$, or $C(R^{B4b})_2$ wherein $R^{B4a}$ is hydrogen, a nitrogen protecting group, or $C_{1-6}$ alkyl, and each occurrence of $R^{B4b}$ is hydrogen, halogen, or $C_{1-6}$ alkyl, or two $R^{B4b}$ groups are joined to form an optionally substituted carbocyclic or heterocyclic ring;

$X^{B2}$ is nitrogen or $CR^{B2a}$, wherein $R^{B2a}$ is hydrogen, halogen, or $C_{1-6}$ alkyl;

each instance of $R^{B1}$ is independently selected from the group consisting of halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{B1a}$, —$N(R^{B1b})_2$, —$SR^{B1a}$, —$C(=O)R^{B1a}$, —$C(=O)OR^{B1a}$, —$C(=O)SR^{B1a}$, —$C(=O)N(R^{B1b})_2$, —$OC(=O)R^{B1a}$, —$OC(=O)OR^{B1a}$, —$OC(=O)SR^{B1a}$, —$OC(=O)N(R^{B1b})_2$, —$NR^{B1b}C(=O)R^{B1b}$, —$NR^{B1b}C(=O)OR^{B1a}$, —$NR^{B1b}C(=O)SR^{B1a}$, —$NR^{B1b}C(=O)N(R^{B1b})_2$, —$SC(=O)R^{B1a}$, —$SC(=O)OR^{B1a}$, —$SC(=O)SR^{B1a}$, —$SC(=O)N(R^{B1b})_2$, —$C(=NR^{B1b})R^{B1a}$, —$C(=NR^{B1b})OR^{B1a}$, —$C(=NR^{B1b})SR^{B1a}$, —$C(=NR^{B1b})N(R^{B1b})_2$, —$OC(=NR^{B1b})R^{B1a}$, —$OC(=NR^{B1b})OR^{B1a}$, —$OC(=NR^{B1b})SR^{B1a}$, —$OC(=NR^{B1b})N(R^{B1b})_2$, —$NR^{B1b}C(=NR^{B1b})R^{B1b}$, —$NR^{B1b}C(=NR^{B1b})OR^{B1a}$, —$NR^{B1b}C(=NR^{B1b})SR^{B1a}$, —$NR^{B1b}C(=NR^{B1b})N(R^{B1b})_2$, —$SC(=NR^{B1b})R^{B1a}$, —$SC(=NR^{B1b})OR^{B1a}$, —$SC(=NR^{B1b})SR^{B1a}$, —$SC(=NR^{B1b})N(R^{B1b})_2$, —$C(=S)R^{B1a}$, —$C(=S)OR^{B1a}$, —$C(=S)SR^{B1a}$, —$C(=S)N(R^{B1b})_2$, —$OC(=S)R^{B1a}$, —$OC(=S)OR^{B1a}$, —$OC(=S)SR^{B1a}$, —$OC(=S)N(R^{B1b})_2$, —$NR^{B1b}C(=S)R^{B1b}$, —$NR^{B1b}C(=S)OR^{B1a}$, —$NR^{B1b}C(=S)SR^{B1a}$, —$NR^{B1b}C(=S)N(R^{B1b})_2$, —$SC(=S)R^{B1a}$, —$SC(=S)OR^{B1a}$, —$SC(=S)SR^{B1a}$, —$SC(=S)N(R^{B1b})_2$, —$S(=O)R^{B1a}$, —$SO_2R^{B1a}$, —$NR^{B1b}SO_2R^{B1a}$, —$SO_2N(R^{B1b})_2$, —CN, —SCN, and —$NO_2$, wherein each occurrence of $R^{B1a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, and each occurrence of $R^{B1b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{B1b}$ groups are joined to form an optionally substituted heterocyclic ring;

each instance of $R^{B2}$, $R^{B3}$, $R^{B4}$, and $R^{B5}$ is independently hydrogen, halogen, or $C_{1-6}$ alkyl;

$R^{B6}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{B6a}$, —$N(R^{B6b})_2$, or —$SR^{B6a}$, wherein each occurrence of $R^{B6a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, and each occurrence of $R^{B6b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{B6b}$ groups are joined to form an optionally substituted heterocyclic ring;

p is 0, 1, 2, 3, or 4.

In yet another aspect, the invention provides compounds of Formula (C):

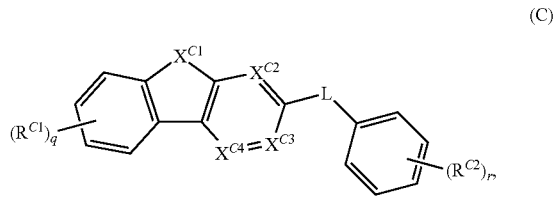

(C)

and pharmaceutically acceptable salts, solvates, hydrates, polymorphs, co-crystals, tautomers, stereoisomers, isotopically labeled derivatives, and prodrugs thereof, wherein $X^{C1}$ is oxygen, sulfur, or $NR^{C1a}$, wherein $R^{C1a}$ is hydrogen, a nitrogen protecting group, or $C_{1-6}$ alkyl;

each instance of $X^{C2}$, $X^{C3}$, and $X^{C4}$ is independently nitrogen or $CR^{C4a}$, wherein $R^{C4a}$ is hydrogen, halogen, or $C_{1-6}$ alkyl;

L is a bond; cyclic or acyclic, substituted or unsubstituted alkylene; cyclic or acyclic, substituted or unsubstituted alkenylene; cyclic or acyclic, substituted or unsubstituted alkynylene; cyclic or acyclic, substituted or unsubstituted heteroalkylene; cyclic or acyclic, substituted or unsubstituted heteroalkenylene; cyclic or acyclic, substituted or unsubstituted heteroalkynylene; substituted or unsubstituted arylene; or substituted or unsubstituted heteroarylene;

each instance of $R^{C1}$ and $R^{C2}$ is independently selected from the group consisting of halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{C2a}$, $-N(R^{C2b})_2$, $-SR^{C2a}$, $-C(=O)R^{C2a}$, $-C(=O)OR^{C2a}$, $-C(=O)SR^{C2a}$, $-C(=O)N(R^{C2b})_2$, $-OC(=O)R^{C2a}$, $-OC(=O)OR^{C2a}$, $-OC(=O)SR^{C2a}$, $-OC(=O)N(R^{C2b})_2$, $-NR^{C2b}C(=O)R^{C2b}$, $-NR^{C2b}C(=O)OR^{C2a}$, $-NR^{C2b}C(=O)SR^{C2a}$, $-NR^{C2b}C(=O)N(R^{C2b})_2$, $-SC(=O)R^{C2a}$, $-SC(=O)OR^{C2a}$, $-SC(=O)SR^{C2a}$, $-SC(=O)N(R^{C2b})_2$, $-C(=NR^{C2b})R^{C2a}$, $C(=NR^{C1b})OR^{C2a}$, $-C(=NR^{C2b})SR^{C2a}$, $-C(=NR^{C2b})N(R^{C2b})_2$, $-OC(=NR^{C2b})R^{C2a}$, $-OC(=NR^{C2b})OR^{C2a}$, $-OC(=NR^{C2b})SR^{C2a}$, $-OC(=NR^{C2b})N(R^{C2b})_2$, $-NR^{C2b}C(=NR^{C2b})R^{C2b}$, $-NR^{C2b}C(=NR^{C2b})OR^{C2a}$, $-NR^{C2b}C(=NR^{C2b})SR^{C2a}$, $-NR^{C2b}C(=NR^{C2b})N(R^{C2b})_2$, $-SC(=NR^{C2b})R^{C2a}$, $-SC(=NR^{C2b})OR^{C2a}$, $-SC(=NR^{C2b})SR^{C2a}$, $-SC(=NR^{C2b})N(R^{C2b})_2$, $-C(=S)R^{C2a}$, $-C(=S)OR^{C2a}$, $-C(=S)SR^{C2a}$, $-C(=S)N(R^{C2b})_2$, $-OC(=S)R^{C2a}$, $-OC(=S)OR^{C2a}$, $-OC(=S)SR^{C2a}$, $-OC(=S)N(R^{C2b})_2$, $-NR^{C2b}C(=S)R^{C2b}$, $-NR^{C2b}C(=S)OR^{C2a}$, $-NR^{C2b}C(=S)SR^{C2a}$, $-NR^{C2b}C(=S)N(R^{C2b})_2$, $-SC(=S)R^{C2a}$, $-SC(=S)OR^{C2a}$, $-SC(=S)SR^{C2a}$, $-SC(=S)N(R^{C2b})_2$, $-S(=O)R^{C2a}$, $-SO_2R^{C2a}$, $-NR^{C2b}SO_2R^{C2a}$, $-SO_2N(R^{C2b})_2$, $-CN$, $-SCN$, and $-NO_2$, wherein each occurrence of $R^{C2a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, and each occurrence of $R^{C2b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{C2b}$ groups are joined to form an optionally substituted heterocyclic ring;

q is 0, 1, 2, 3, or 4; and r is 0, 1, 2, 3, 4, or 5.

In yet another aspect, the invention provides compounds of Formula (D):

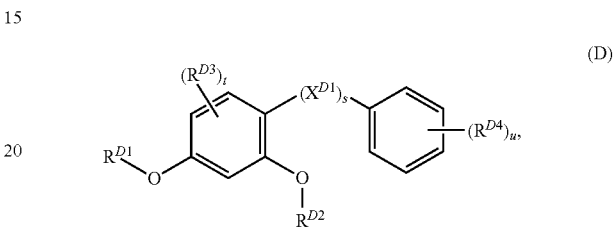

(D)

and pharmaceutically acceptable salts, solvates, hydrates, polymorphs, co-crystals, tautomers, stereoisomers, isotopically labeled derivatives, and prodrugs thereof, wherein each instance of $X^{D1}$ is independently oxygen, sulfur, $NR^{D1a}$, or $C(R^{D1b})_2$, wherein $R^{D1a}$ is hydrogen or $C_{1-6}$ alkyl, and each occurrence of $R^{D1b}$ is hydrogen, halogen, or $C_{1-6}$ alkyl, or two $R^{D1b}$ groups are joined to form an optionally substituted carbocyclic or heterocyclic ring;

s is 0, 1, 2, 3, 4, 5, or 6;

each instance of $R^{D1}$ and $R^{D2}$ is independently hydrogen, an oxygen protecting group, $C_{1-6}$ alkyl, $-C(=O)R^{D2a}$, $-C(=O)OR^{D2a}$, $-C(=O)SR^{D2a}$, $-C(=O)N(R^{D2b})_2$, $-S(=O)R^{D2a}$, or $-S(=O)_2R^{D2a}$, wherein each occurrence of $R^{D2a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, and each occurrence of $R^{D2b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{D2b}$ groups are joined to form an optionally substituted heterocyclic ring;

each instance of $R^{D3}$ and $R^{D4}$ is independently selected from the group consisting of halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{D4a}$, $-N(R^{D4b})_2$, $-SR^{D4a}$, $-C(=O)R^{D4a}$, $-C(=O)OR^{D4a}$, $C(=O)SR^{D4a}$, $-C(=O)N(R^{D4b})_2$, $-OC(=O)R^{D4a}$, $-OC(=O)OR^{D4a}$, $-OC(=O)SR^{D4a}$, $-OC(=O)N(R^{D4b})_2$, $-NR^{D4b}C(=O)R^{D4b}$, $-NR^{D4b}C(=O)OR^{D4a}$, $-NR^{D4b}C(=O)SR^{D4a}$, $-NR^{D4b}C(=O)N(R^{D4b})_2$, $-SC(=O)R^{D4a}$, $-SC(=O)OR^{D4a}$, $-SC(=O)SR^{D4a}$, $-SC(=O)N(R^{D4b})_2$, $-C(=NR^{D4b})R^{D4a}$, $-C(=NR^{D4b})OR^{D4a}$, $-C(=NR^{D4b})SR^{D4a}$, $-C(=NR^{D4b})N(R^{D4b})_2$, $-OC(=NR^{D4b})R^{D4a}$, $-OC(=NR^{D4b})OR^{D4a}$, $-OC(=NR^{D4b})SR^{D4a}$, $-OC(=NR^{D4b})N(R^{D4b})_2$, $-NR^{D4b}C(=NR^{D4b})R^{D4b}$, $-NR^{D4b}C(=NR^{D4b})OR^{D4a}$, $-NR^{D4b}C(=NR^{D4b})SR^{D4a}$, $-NR^{D4b}C(=NR^{D4b})N(R^{D4b})_2$, $-SC(=NR^{D4b})R^{D4a}$, $-SC(=NR^{D4b})OR^{D4a}$, $-SC(=NR^{D4b})SR^{D4a}$, $-SC(=NR^{D4b})N(R^{D4b})_2$, $-C(=S)R^{D4a}$, $-C(=S)OR^{D4a}$, —C(=S)SR$^{D4a}$, —C(=S)N(R$^{D4b}$)$_2$, —OC(=S)R$^{D4a}$, —OC(=S)OR$^{D4a}$, —OC(=S)SR$^{D4a}$, —OC(=S)N(R$^{D4b}$)$_2$, —NR$^{D4b}$C(=S)R$^{D4b}$, —NR$^{D4b}$C(=S)OR$^{D4a}$, —NR$^{D4b}$C(=S)SR$^{D4a}$, —NR$^{D4b}$C(=S)N(R$^{D4b}$)$_2$, —SC(=S)R$^{D4a}$, —SC(=S)OR$^{D4a}$, —SC(=S)SR$^{D4a}$, —SC(=S)N(R$^{D4b}$)$_2$, —S(=O)R$^{D4a}$, —SO$_2$R$^{D4a}$, —NR$^{D4b}$SO$_2$R$^{D4a}$, —SO$_2$N(R$^{D4b}$)$_2$, —CN, —SCN, and —NO$_2$, wherein each occurrence of R$^{D4a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, and each occurrence of R$^{D4b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two R$^{D4b}$ groups are joined to form an optionally substituted heterocyclic ring;

t is 0, 1, 2, or 3; and u is 0, 1, 2, 3, 4 or 5.

In still another aspect, provided are pharmaceutical compositions comprising a compound of any of the Formulae (A), (B), (C), and (D), and pharmaceutically acceptable salts, solvates, hydrates, polymorphs, co-crystals, tautomers, stereoisomers, isotopically labeled derivatives, and prodrugs thereof, and optionally a pharmaceutically acceptable excipient.

In still another aspect, the invention provides methods and compositions for the suppression of DNA damage in neuronal cells.

In still another aspect, the invention provides methods and compositions for the treatment of neurological disorders. In certain embodiments, the method comprises administering to a subject in need of treatment for a neurological disorder a therapeutically effective amount of a class I HDAC (histone deacetylase) activator to treat the neurological disorder. In some embodiments, the neurological disorder is Alzheimer's disease, Parkinson's disease, Huntington's disease, ALS (Amyotrophic lateral sclerosis), traumatic brain injury, or ischemic brain injury. In some embodiments, the class I HDAC activator is selected from the group of compounds consisting of:

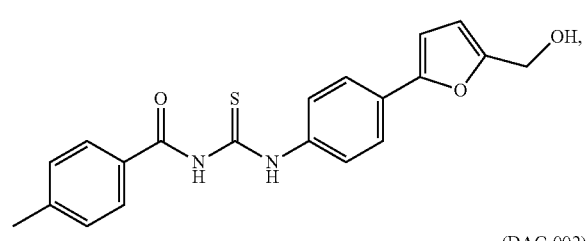
(DAC-001)

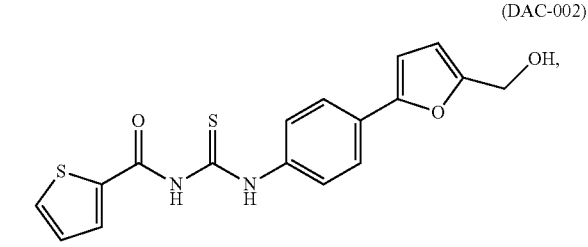
(DAC-002)

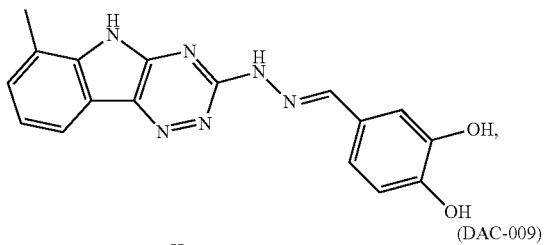
(DAC-003)

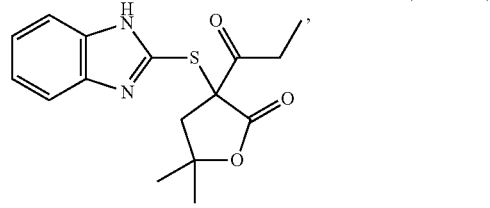
(DAC-009)

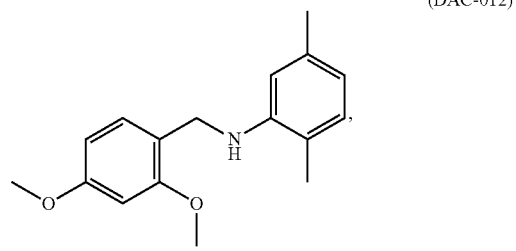
(DAC-012)

and compounds of the Formulae (A), (B), (C), and (D), and pharmaceutically acceptable salts, solvates, hydrates, polymorphs, co-crystals, tautomers, stereoisomers, isotopically labeled derivatives, and prodrugs thereof, or pharmaceutical compositions thereof.

In another aspect, the invention provides kits for treating a neurological disorder comprising a first container comprising a class I HDAC activator selected from the group of compounds consisting of DAC-001, DAC-002, DAC-003, DAC-009, DAC-012, and compounds of the Formulae (A), (B), (C), and (D), and pharmaceutically acceptable salts, solvates, hydrates, polymorphs, co-crystals, tautomers, stereoisomers, isotopically labeled derivatives, and prodrugs thereof, or pharmaceutical compositions thereof.

This Application refers to various issued patent, published patent applications, journal articles, and other publications, all of which are incorporated herein by reference.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of the terms "including", "comprising", "having", "containing", "involving", and variations thereof herein is meant to encompass the items listed thereafter and equivalents thereof as well as additional items.

DEFINITIONS

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

The term "heteroalkyl," as used herein, refers to an alkyl moiety, as defined herein, which contains one or more oxygen, sulfur, nitrogen, phosphorus, or silicon atoms, e.g., in place of carbon atoms.

The term "heteroalkenyl," as used herein, refers to an alkenyl moiety, as defined herein, which contains one or more oxygen, sulfur, nitrogen, phosphorus, or silicon atoms, e.g., in place of carbon atoms.

The term "heteroalkynyl," as used herein, refers to an alkynyl moiety, as defined herein, which contains one or more oxygen, sulfur, nitrogen, phosphorus, or silicon atoms, e.g., in place of carbon atoms.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo(2.2.1)heptanyl ($C_7$), bicyclo (2.2.2)octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro(4.5)decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothiophenyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl, as defined herein, and refers to an alkyl group substituted with an optionally substituted aryl group.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has one ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl, and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl, as defined herein, and refers to an alkyl group substituted with an optionally substituted heteroaryl group.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., the group contains all single bonds.

Alkyl, alkenyl, alkynyl, carbocyclyl, heterocyclyl, aryl, and heteroaryl groups, as defined herein, which are divalent bridging groups are further referred to using the suffix -ene, e.g., alkylene, alkenylene, alkynylene, carbocyclylene, heteroalkylene, heteroalkenylene, heteroalkynylene, heterocyclylene, arylene, and heteroarylene.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl, or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that result in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{cc}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{cc}$, —C(=O)R$^{cc}$, —CO$_2$H, —CO$_2$R$^{cc}$, —OC(=O)R$^{cc}$, —OCO$_2$R$^{cc}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

A "leaving group" is an art-understood term referring to a molecular fragment that departs with a pair of electrons in heterolytic bond cleavage, wherein the molecular fragment is an anion or neutral molecule. See, for example, Smith, *March's Advanced Organic Chemistry* 6th ed. (501-502). Exemplary leaving groups include, but are not limited to, halogen (e.g., chloro, bromo, iodo), activated hydroxyl groups (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$ wherein R$^{aa}$, R$^{bb}$, and R$^{cc}$ are as defined herein), substituted thiol groups (e.g., —SR$^{aa}$, for example, as a molecular fragment departing from of a compound of the formula R$^{aa}$S—SR$^{aa}$), substituted nitrogen groups (e.g., —NR$^{bb}$, for example, as a molecular fragment departing from of a compound of formula Br—N(R$^{bb}$)$_2$, Cl—N(R$^{bb}$)$_2$, I—N(R$^{bb}$)$_2$,$^b$, and F—N(R$^{bb}$)$_2$), —CN, and —N$_2$.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Amide nitrogen protecting groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Carbamate nitrogen protecting groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-(9-(10,10-dioxo-10,10, 10,10-tetrahydrothioxanthyl))methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, (2-(1,3-dithianyl)methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolymethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Sulfonamide nitrogen protecting groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-(2-(trimethylsilyl)ethoxy)methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-((4-methoxyphenyl)diphenylmethyl)amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-((2-pyridyl)mesityl)methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-(phenyl(pentaacylchromium- or tungsten)acyl)amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-ethoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-((2-chloro-4-methyl)phenyl)-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

An "isomer" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention.

"Tautomer" includes two or more interconvertible compounds resulting from at least one formal migration of a hydrogen atom and at least one change in valency (e.g., a single bond to a double bond, a triple bond to a double bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol; amide-to-imide; lactam-to-lactim; enamine-to-imine; and enamine-to-(a different) enamine tautomerizations.

These and other exemplary substituents are described in more detail in the Detailed Description, Examples, and claims. The invention is not intended to be limited in any manner by the above exemplary listing of substituents.

OTHER DEFINITIONS

The term "animal," as used herein, refers to humans as well as non-human animals, including, e.g., mammals, birds, reptiles, amphibians, and fish. Preferably, the non-human animal is a mammal (e.g., a rodent, a mouse, a rat, a rabbit, a monkey, a dog, a cat, a primate, or a pig). A non-human animal may be a transgenic animal.

"Salt" or "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid, or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(Cl^-{}_4 alkyl)_4$ salts. Representative alkali or alkaline earth metal salts include sodium, lithium, potassium, calcium, magnesium, and the like. Further pharmaceutically acceptable salts include, when appropriate, quaternary salts.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

"Treat," "treating," and "treatment" contemplate an action that occurs while a subject is suffering from a condition which reduces the severity of the condition or retards or slows the progression of the condition ("therapeutic treatment"), and also contemplates an action that occurs before a subject begins to suffer from the condition and which inhibits or reduces the severity of the condition ("prophylactic treatment").

An "effective amount" of a compound refers to an amount sufficient to elicit the desired biological response, i.e., treating the condition. As will be appreciated by those of ordinary skill in this art, the effective amount of a compound of the invention may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound is an amount sufficient to provide a therapeutic benefit in the treatment of a condition or to delay or minimize one or more symptoms associated with the condition. A therapeutically effective amount of a compound means an amount of a therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "pharmaceutically acceptable excipient" is an excipient that is non-toxic to recipients at the dosages and concentrations employed, and is compatible with other ingredients of the formulation. Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and Remington: *The Science and Practice of Pharmacy*, 21st Edition (Lippincott Williams & Wilkins, 2005).

A "small molecule" is a low molecular weight organic compound which is not a polymer. The term small molecule, especially within the field of pharmacology, is usually restricted to a molecule that also binds with high affinity to a biopolymer such as protein, polysaccharide, or nucleic acid and in addition alters the activity or function of the biopolymer. The upper limit for a small molecule's molecular weight is about 800 Daltons which allows for the possibility to rapidly diffuse across cell membranes so that they can reach intracellular sites of action.

A "protein" or "peptide" comprises a polymer of amino acid residues linked together by peptide bonds. The term, as used herein, refers to proteins, polypeptides, and peptide of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. A protein may be just a fragment of a naturally occurring protein or peptide. A protein may be naturally occurring, recombinant, or synthetic, or any combination of these.

"Histones" are highly alkaline proteins found in eukaryotic cell nuclei that package and order the DNA into structural units called nucleosomes. They are the chief protein components of chromatin, acting as spools around which DNA winds, and play a role in gene regulation.

"Histone deacetylases" (HDACs) are a class of enzymes that remove acetyl groups from an ε-N-acetyl lysine amino acid on a histone. DNA is wrapped around histones, and DNA expression is regulated by acetylation and deacetylation.

"Class I histone deacetylase" or "class I HDAC" is a subclass of HDACs.

"HDAC1" or "histone deacetylase 1" is a subclass of class I HDACs.

A "DAC" refers to a compound that activates class I HDACs' enzymatic function.

BRIEF DESCRIPTION OF THE DRAWINGS

FIG. 3 includes HDAC1 microfluidics high-throughput screening data.

FIG. 5 shows that DAC compounds protect cells from stress-induced cell death. FIG. 5C shows that DAC compounds have minimal effects on cell proliferation and survival at their working concentration (5 μM for DAC-001 and DAC-003; 10 μM for the others).

DETAILED DESCRIPTION OF CERTAIN EMBODIMENTS OF THE INVENTION

Figure 1:
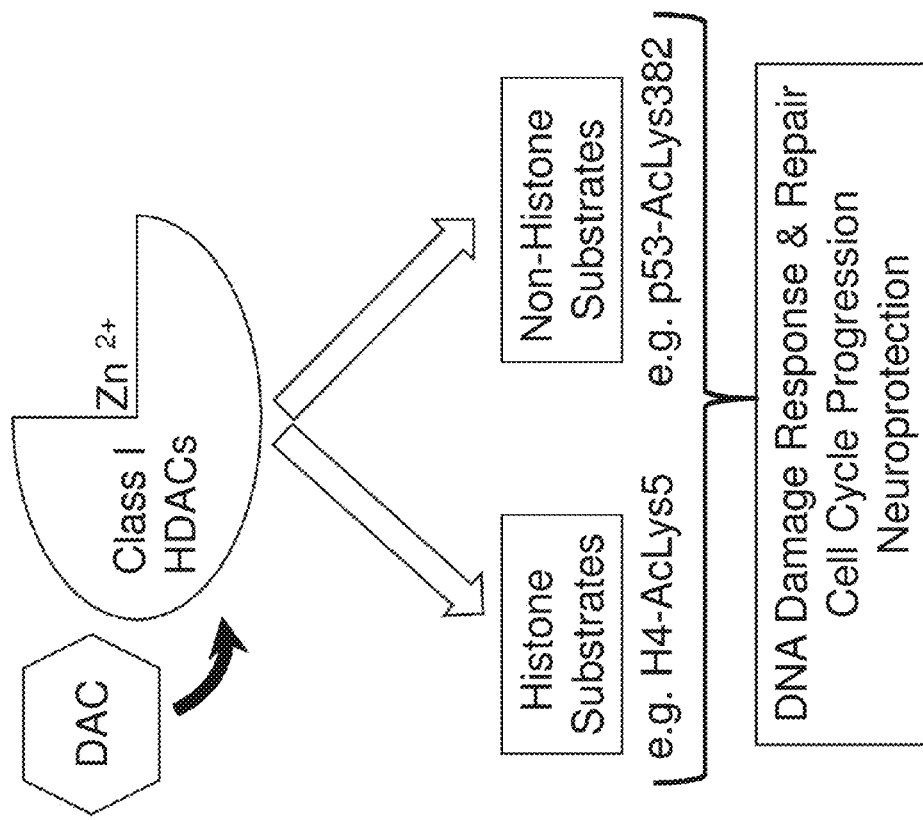
FIG. 1 shows an overview of small molecule modulators of class I HDACs and relevance to response to DNA damage, DNA repair, and neuroprotection. HDAC1, HDAC2, HDAC3, and HDAC8 are zinc-dependent hydrolases that remove acetyl groups from the ε-amino group of lysine side chains. Class I HDACs have also been found to have other enzymatic activities, including esterase activity.

The present invention provides compounds that activate Class I histone deacetlyases (HDACs), and pharmaceutical compositions thereof, for the treatment of human disease. The present invention further provides methods of using the compounds described herein, e.g., as biological probes to study the activation of HDACs, and as therapeutics, e.g., in the treatment of neurological disorders, such as Alzheimer's disease, Parkinson's disease, Huntington's disease, ALS (Amyotrophic lateral sclerosis), traumatic brain injury, ischemic brain injury, stroke, frontal temporal dementia, Pick's disease, corticobasal degeneration, supra cerebral palsy, prion diseases (e.g., Creutzfeldt-Jakob disease, Gerstmann-Straussler-Scheinker syndrome, Fatal Familial Insomnia, and Kuru), Nieman Pick type C, spinal cerebellar ataxia, spinal muscular dystrophy, ataxia telangiectasia, hippocampal sclerosis, Cockayne syndrome, Werner syndrome, xeroderma pigmentosaum, or Bloom syndrome.

Compounds 47,144 compounds were screened for hit compounds, which enhance the enzymatic activity of class I HDAC, especially, HDAC1. Of the hit compounds, multiple common structural frameworks were identified, suggesting the existence of a defined structure-activity-relationship for HDAC1 activation.

The compounds depicted below and herein may be prepared by conventional chemical transformations (including protecting group methodologies), e.g., those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof. The compounds can also be synthesized in manners similar to those described with necessary modifications as recognized by those skilled in the art.

In one aspect, provided is a compound of Formula (A):

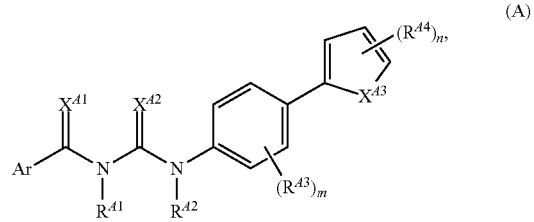

and pharmaceutically acceptable salts, solvates, hydrates, polymorphs, co-crystals, tautomers, stereoisomers, isotopically labeled derivatives, and prodrugs thereof, wherein each instance of $X^{A1}$, $X^{A2}$, and $X^{A3}$ is independently oxygen or sulfur;

each instance of $R^{A1}$ and $R^{A2}$ is independently hydrogen, a nitrogen protecting group, or $C_{1-6}$ alkyl;

Ar is optionally substituted aryl or optionally substituted heteroaryl;

each instance of $R^{A3}$ and $R^{A4}$ is independently selected from the group consisting of halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{A3a}$, $-N(R^{A3b})_2$, $-SR^{A3a}$, $-C(=O)R^{A3a}$, $-C(=O)OR^{A3a}$, $-C(=O)SR^{A3a}$, $-C(=O)N(R^{A3b})_2$, $-OC(=O)R^{A3a}$, $-OC(=O)OR^{A3a}$, $-OC(=O)SR^{A3a}$, $-OC(=O)N(R^{A3b})_2$, $-NR^{A3b}C(=O)R^{A3b}$, $-NR^{A3b}C(=O)OR^{A3a}$, $-NR^{A3b}C(=O)SR^{A3a}$, $-NR^{A3b}C(=O)N(R^{A3b})_2$, $-SC(=O)R^{A3a}$, $-SC(=O)OR^{A3a}$, $-SC(=O)SR^{A3a}$, $-SC(=O)N(R^{A3b})_2$, $-C(=NR^{A3b})R^{A3a}$, $-C(=NR^{A3b})OR^{A3a}$, $-C(=NR^{A3b})SR^{A3a}$, $-C(=NR^{A3b})N(R^{A3b})_2$, $-OC(=NR^{A3b})R^{A3a}$, $-OC(=NR^{A3b})OR^{A3a}$, $-OC(=NR^{A3b})SR^{A3a}$, $-OC(=NR^{A3b})N(R^{A3b})_2$, $-NR^{A3b}C(=NR^{A3b})R^{A3b}$, $-NR^{A3b}C(=NR^{A3b})OR^{A3a}$, $-NR^{A3b}C(=NR^{A3b})SR^{A3a}$, $-NR^{A3b}C(=NR^{A3b})N(R^{A3b})_2$, $-SC(=NR^{A3b})R^{A3a}$, $-SC(=NR^{A3b})OR^{A3a}$, $-SC(=NR^{A3b})SR^{A3a}$, $-SC(=NR^{A3b})N(R^{A3b})_2$, $-C(=S)R^{A3a}$, $-C(=S)OR^{A3a}$, $-C(=S)SR^{A3a}$, $-C(=S)N(R^{A3b})_2$, $-OC(=S)R^{A3a}$, $-OC(=S)OR^{A3a}$, $-OC(=S)SR^{A3a}$, $-OC(=S)N(R^{A3b})_2$, $-NR^{A3b}C(=S)R^{A3b}$, $-NR^{A3b}C(=S)OR^{A3a}$, $-NR^{A3b}C(=S)SR^{A3a}$, $-NR^{A3b}C(=S)N(R^{A3b})_2$, $-SC(=S)R^{A3a}$, $-SC(=S)OR^{A3a}$, $-SC(=S)SR^{A3a}$, $-SC(=S)N(R^{A3b})_2$, $-S(=O)R^{A3a}$, $-SO_2R^{A3a}$, $-NR^{A3b}SO_2R^{A3a}$, $-SO_2N(R^{A3b})_2$, $-CN$, $-SCN$, and $-NO_2$, wherein each occurrence of $R^{A3a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, and each occurrence of $R^{A3b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{A3b}$ groups are joined to form an optionally substituted heterocyclic ring;

m is 0, 1, 2, 3, or 4; and n is 0, 1, 2, or 3.

In certain embodiments, $X^{A1}$, $X^{A2}$, and $X^{A3}$ are oxygen. In certain embodiments, $X^{A1}$ and $X^{A2}$ are oxygen, and $X^{A3}$ is sulfur. In certain embodiments, $X^{A1}$ and $X^{A3}$ are oxygen, and $X^{A2}$ is sulfur. In certain embodiments, $X^{A2}$ and $X^{A3}$ are oxygen, and $X^{A1}$ is sulfur. In certain embodiments, $X^{A1}$ and $X^{A2}$ are sulfur, and $X^{A3}$ is oxygen. In certain embodiments, $X^{A1}$ and $X^{A3}$ are sulfur, and $X^{A2}$ is oxygen. In certain embodiments, $X^{A2}$ and $X^{A3}$ are sulfur, and $X^{A1}$ is oxygen. In certain embodiments, $X^{A1}$, $X^{A2}$, and $X^{A3}$ are sulfur.

In certain embodiments, $R^{A1}$ is hydrogen. In certain embodiments, $R^{A1}$ is a nitrogen protecting group. In certain embodiments, $R^{A1}$ is $C_{1-6}$ alkyl. In certain embodiments, $R^{A1}$ is methyl.

In certain embodiments, $R^{A2}$ is hydrogen. In certain embodiments, $R^{A2}$ is a nitrogen protecting group. In certain embodiments, $R^{A2}$ is $C_{1-6}$ alkyl. In certain embodiments, $R^{A2}$ is methyl.

In certain embodiments, $R^{A1}$ and $R^{A2}$ are both hydrogen.

In certain embodiments, $X^{A1}$ and $X^{A3}$ are oxygen, $X^{A2}$ is sulfur, and $R^{A1}$ and $R^{A2}$ are hydrogen.

In certain embodiments, Ar is aryl. In certain embodiments, Ar is substituted aryl. In certain embodiments, Ar is heteroaryl. In certain embodiments, Ar is substituted heteroaryl.

In certain embodiments, each instance of $R^{A3}$ is independently optionally substituted alkyl. In certain embodiments, each instance of $R^{A3}$ is independently optionally substituted $C_{1-6}$ alkyl. In certain embodiments, each instance of $R^{A3}$ is independently optionally substituted methyl. In certain embodiments, each instance of $R^{A3}$ is independently methyl.

In certain embodiments, each instance of $R^{A4}$ is independently optionally substituted alkyl. In certain embodiments, each instance of $R^{A4}$ is independently optionally substituted $C_{1-6}$ alkyl. In certain embodiments, each instance of $R^{A4}$ is independently optionally substituted methyl. In certain embodiments, each instance of $R^{A4}$ is independently optionally substituted hydroxyl-substituted alkyl. In certain embodiments, each instance of $R^{A4}$ is independently optionally substituted hydroxyl-substituted $C_{1-6}$ alkyl. In certain embodiments, each instance of $R^{A4}$ is independently substituted hydroxymethyl. In certain embodiments, each instance of $R^{A4}$ is independently hydroxymethyl.

In certain embodiments, m is 0. In certain embodiments, m is 1. In certain embodiments, m is 2. In certain embodiments, m is 3. In certain embodiments, m is 4.

In certain embodiments, $X^{A1}$ and $X^{A3}$ are oxygen, $X^{A2}$ is sulfur, $R^{A1}$ and $R^{A2}$ are hydrogen, and m is 0.

In certain embodiments, n is 0. In certain embodiments, n is 1. In certain embodiments, n is 2. In certain embodiments, n is 3.

In certain embodiments, wherein Ar is optionally substituted phenyl, provided is a compound of Formula (A-I):

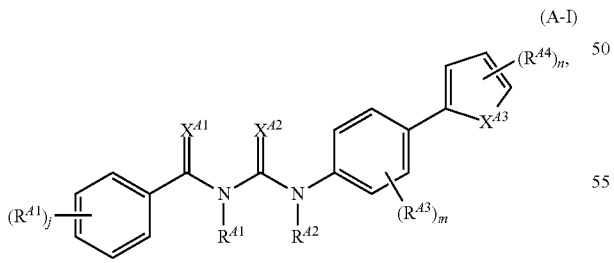

(A-I)

and pharmaceutically acceptable salts, solvates, hydrates, polymorphs, co-crystals, tautomers, stereoisomers, isotopically labeled derivatives, and prodrugs thereof, wherein
$X^{A1}$, $X^{A2}$, $X^{A3}$, $R^{A1}$, $R^{A2}$, $R^{A3}$, $R^{A4}$, m, and n are as defined herein;

each instance of $R^{A1}$ is independently selected from the group consisting of halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{AIa}$, —$N(R^{AIb})_2$, —$SR^{AIa}$, —$C(=O)R^{AIa}$, —$C(=O)OR^{AIa}$, —$C(=O)SR^{AIa}$, —$C(=O)N(R^{AIb})_2$, —$OC(=O)R^{AIa}$, —$OC(=O)OR^{AIa}$, —$OC(=O)SR^{AIa}$, —$OC(=O)N(R^{AIb})_2$, —$NR^{AIb}C(=O)R^{AIb}$, —$NR^{AIb}C(=O)OR^{AIa}$, —$NR^{AIb}C(=O)SR^{AIa}$, —$NR^{AIb}C(=O)N(R^{AIb})_2$, —$SC(=O)R^{AIa}$, —$SC(=O)OR^{AIa}$, —$SC(=O)SR^{AIa}$, —$SC(=O)N(R^{AIb})_2$, —$C(=NR^{AIb})R^{AIa}$, —$C(=NR^{AIb})OR^{AIa}$, —$C(=NR^{AIb})SR^{AIa}$, —$C(=NR^{AIb})N(R^{AIb})_2$, —$OC(=NR^{AIb})R^{AIa}$, —$OC(=NR^{AIb})OR^{AIa}$, —$OC(=NR^{AIb})SR^{AIa}$, —$OC(=NR^{AIb})N(R^{AIb})_2$, —$NR^{AIb}C(=NR^{AIb})R^{AIb}$, —$NR^{AIb}C(=NR^{AIb})OR^{AIa}$, —$NR^{AIb}C(=NR^{AIb})SR^{AIa}$, —$NR^{AIb}C(=NR^{AIb})N(R^{AIb})_2$, —$SC(=NR^{AIb})R^{AIa}$, —$SC(=NR^{AIb})OR^{AIa}$, —$SC(=NR^{AIb})SR^{AIa}$, —$SC(=NR^{AIb})N(R^{AIb})_2$, —$C(=S)R^{AIa}$, —$C(=S)OR^{AIa}$, —$C(=S)SR^{AIa}$, —$C(=S)N(R^{AIb})_2$, —$OC(=S)R^{AIa}$, —$OC(=S)OR^{AIa}$, —$OC(=S)SR^{AIa}$, —$OC(=S)N(R^{AIb})_2$, —$NR^{AIb}C(=S)R^{AIb}$, —$NR^{AIb}C(=S)OR^{AIa}$, —$NR^{AIb}C(=S)SR^{AIa}$, —$NR^{AIb}C(=S)N(R^{AIb})_2$, —$SC(=S)R^{AIa}$, —$SC(=S)OR^{AIa}$, —$SC(=S)SR^{AIa}$, —$SC(=S)N(R^{AIb})_2$, —$S(=O)R^{AIa}$, —$SO_2R^{AIa}$, —$NR^{AIb}SO_2R^{AIa}$, —$SO_2N(R^{AIb})_2$, —CN, —SCN, and —$NO_2$, wherein each occurrence of $R^{AIa}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or each occurrence of $R^{AIb}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{AIb}$ groups are joined to form a heterocyclic ring; and j is 0, 1, 2, 3, 4, or 5.

In certain embodiments of Formula (A-I), j is 0. In certain embodiments, j is 1. In certain embodiments, j is 2. In certain embodiments, j is 3. In certain embodiments, j is 4. In certain embodiments, j is 5.

In certain embodiments, provided is a compound of any of the formulae:

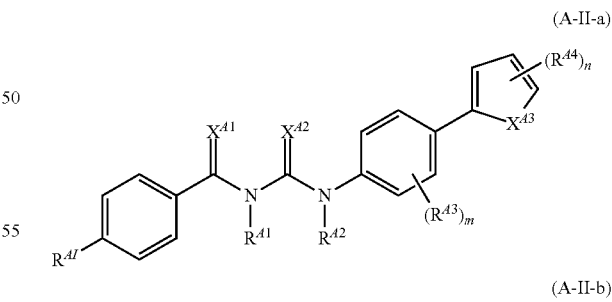

(A-II-a)

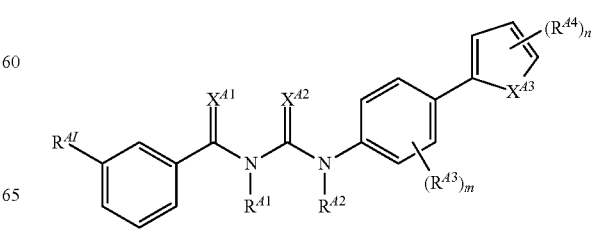

(A-II-b)

(A-II-c)

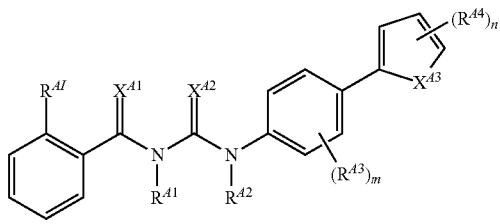

and pharmaceutically acceptable salts, solvates, hydrates, polymorphs, co-crystals, tautomers, stereoisomers, isotopically labeled derivatives, and prodrugs thereof, wherein $X^{A1}$, $X^{A2}$, $X^{A3}$, $R^{A1}$, $R^{A2}$, $R^{A3}$, $R^{A4}$, $R^{AI}$, m, and n are as defined herein.

In certain embodiments, provided is a compound of any of the formulae:

(A-III-a)

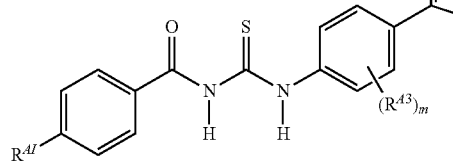

(A-III-b)

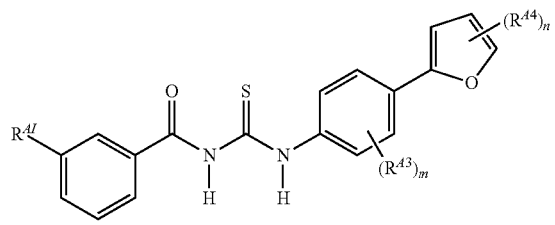

(A-III-c)

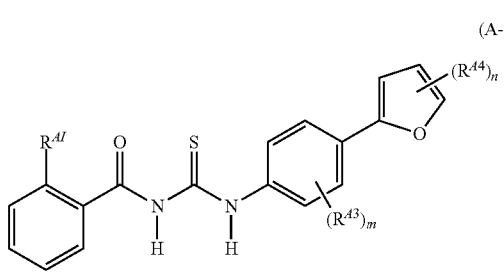

and pharmaceutically acceptable salts, solvates, hydrates, polymorphs, co-crystals, tautomers, stereoisomers, isotopically labeled derivatives, and prodrugs thereof, wherein $R^{A3}$, $R^{A4}$, $R^{AI}$, m, and n are as defined herein.

In certain embodiments, $R^{AI}$ is $C_{1-6}$ alkyl. In certain embodiments, $R^{AI}$ is methyl. In certain embodiments, $R^{AI}$ is ethyl. In certain embodiments, $R^{AI}$ is propyl. In certain embodiments, $R^{AI}$ is butyl.

In certain embodiments, provided is a compound of any of the formulae:

(A-IV-a)

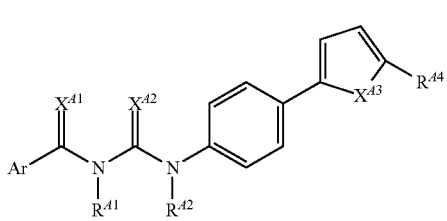

(A-IV-b)

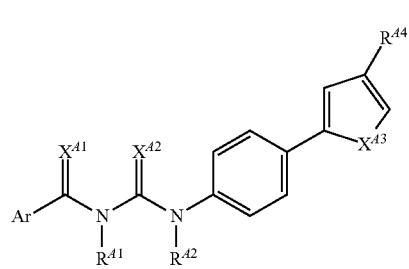

(A-IV-c)

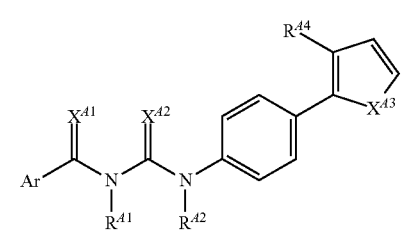

and pharmaceutically acceptable salts, solvates, hydrates, polymorphs, co-crystals, tautomers, stereoisomers, isotopically labeled derivatives, and prodrugs thereof, wherein $X^{A1}$, $X^{A2}$, $X^{A3}$, Ar, $R^{A1}$, $R^{A2}$, and $R^{A4}$ are as defined herein.

In certain embodiments, provided is a compound of any of the formulae:

(A-V-a)

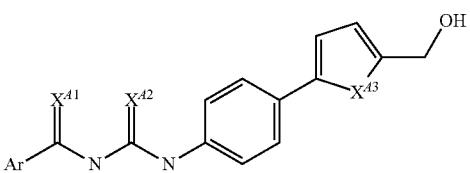

(A-V-b)

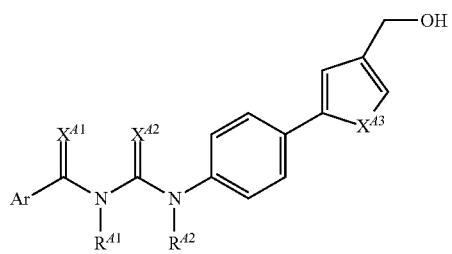

-continued

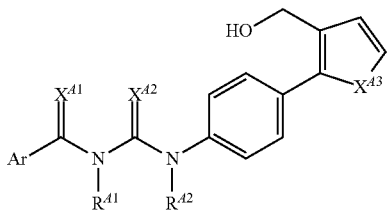

(A-V-c)

and pharmaceutically acceptable salts, solvates, hydrates, polymorphs, co-crystals, tautomers, stereoisomers, isotopically labeled derivatives, and prodrugs thereof, wherein $X^{A1}$, $X^{A2}$, $X^{A3}$, Ar, $R^{A1}$, $R^{A2}$, and $R^{A3}$ are as defined herein.

In certain embodiments, wherein Ar is a optionally substituted thiophenyl, provided is a compound of Formula (A-VI):

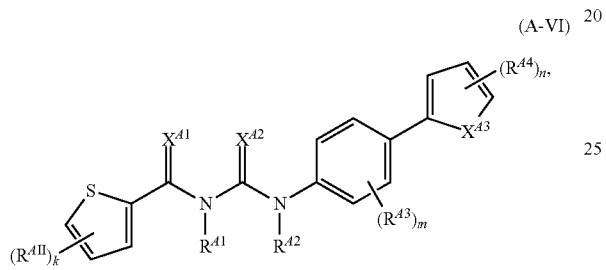

(A-VI)

and pharmaceutically acceptable salts, solvates, hydrates, polymorphs, co-crystals, tautomers, stereoisomers, isotopically labeled derivatives, and prodrugs thereof, wherein
$X^{A1}$, $X^{A2}$, $X^{A3}$, $R^{A1}$, $R^{A2}$, $R^{A3}$, $R^{A4}$, m, and n are as defined herein;

each instance of $R^{AII}$ is independently selected from the group consisting of halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{AIIa}$, —N(R$^{AIIb}$)$_2$, —SR$^{AIIa}$, —C(=O)R$^{AIIa}$, —C(=O)OR$^{AIIa}$, —C(=O)SR$^{AIIa}$, —C(=O)N(R$^{AIIb}$)$_2$, —OC(=O)R$^{AIIa}$, —OC(=O)OR$^{AIIa}$, —OC(=O)SR$^{AIIa}$, —OC(=O)N(R$^{AIIb}$)$_2$, —NR$^{AIIb}$C(=O)R$^{AIIb}$, —NR$^{AIIb}$C(=O)OR$^{AIIa}$, —NR$^{AIIb}$C(=O)SR$^{AIIa}$, —NR$^{AIIb}$C(=O)N(R$^{AIIb}$)$_2$, —SC(=O)R$^{AIIa}$, —SC(=O)OR$^{AIIa}$, —SC(=O)SR$^{AIIa}$, —SC(=O)N(R$^{AIIb}$)$_2$, —C(=NR$^{AIIb}$)R$^{AIIa}$, —C(=NR$^{AIIb}$)OR$^{AIIa}$, —C(=NR$^{AIIb}$)SR$^{AIIa}$, —C(=NR$^{AIIb}$)N(R$^{AIIb}$)$_2$, —OC(=NR$^{AIIb}$)R$^{AIIa}$, —OC(=NR$^{AIIb}$)OR$^{AIIa}$, —OC(=NR$^{AIIb}$)SR$^{AIIa}$, —OC(=NR$^{AIIb}$)N(R$^{AIIb}$)$_2$, —NR$^{AIIb}$C(=NR$^{AIIb}$)R$^{AIIb}$, —NR$^{AIIb}$C(=NR$^{AIIb}$)OR$^{AIIa}$, —NR$^{AIIb}$C(=NR$^{AIIb}$)SR$^{AIIa}$, —NR$^{AIIb}$C(=NR$^{AIIb}$)N(R$^{AIIb}$)$_2$, —SC(=NR$^{AIIb}$)R$^{AIIa}$, —SC(=NR$^{AIIb}$)OR$^{AIIa}$, —SC(=NR$^{AIIb}$)SR$^{AIIa}$, —SC(=NR$^{AIIb}$)N(R$^{AIIb}$)$_2$, —C(=S(R$^{AIIa}$, —C(=S)OR$^{AIIa}$, —C(=S)SR$^{AIIa}$, —C(=S)N(R$^{AIIb}$)$_2$, —OC(=S)R$^{AIIa}$, —OC(=S)OR$^{AIIa}$, —OC(=S)SR$^{AIIa}$, —OC(=S)N(R$^{AIIb}$)$_2$, —NR$^{AIIb}$C(=S)R$^{AIIb}$, —NR$^{AIIb}$C(=S)OR$^{AIIa}$, —NR$^{AIIb}$C(=S)SR$^{AIIa}$, —NR$^{AIIb}$C(=S)N(R$^{AIIb}$)$_2$, —SC(=S)R$^{AIIa}$, —SC(=S)OR$^{AIIa}$, —SC(=S)SR$^{AIIa}$, —SC(=S)N(R$^{AIIb}$)$_2$, —S(=O)R$^{AIIa}$, —SO$_2$R$^{AIIa}$, —NR$^{AIIb}$SO$_2$R$^{AIIa}$, —SO$_2$N(R$^{AIIb}$)$_2$, —CN, —SCN, and —NO$_2$, wherein each occurrence of R$^{AIIa}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, and each occurrence of R$^{AIIb}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two R$^{AIIb}$ groups are joined to form a heterocyclic ring; and k is 0, 1, 2, or 3.

In certain embodiments of Formula (A-VI), k is 0. In certain embodiments, k is 1. In certain embodiments, k is 2. In certain embodiments, k is 3.

In certain embodiments of Formula (A-VI), wherein k is 1, provided is a compound of any of the formulae:

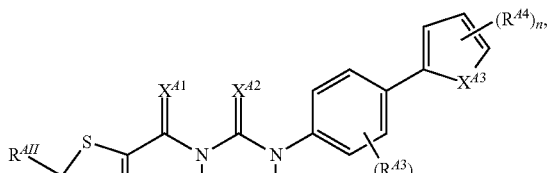

(A-VII-a)

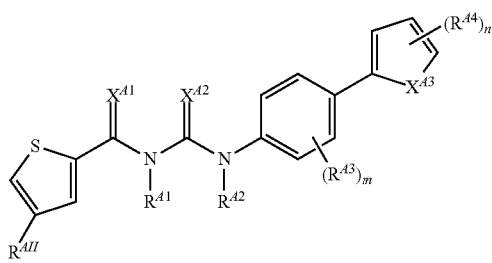

(A-VII-b)

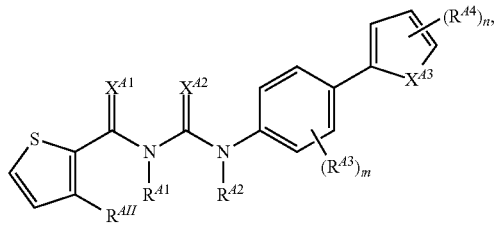

(A-VII-c)

and pharmaceutically acceptable salts, solvates, hydrates, polymorphs, co-crystals, tautomers, stereoisomers, isotopically labeled derivatives, and prodrugs thereof, wherein $X^{A1}$, $X^{A2}$, $X^{A3}$, $R^{A1}$, $R^{A2}$, $R^{A3}$, $R^{A4}$, $R^{AII}$, m, and n are as defined herein.

In certain embodiments of Formula (A-VI), wherein n is 1, provided is a compound of any of the formulae:

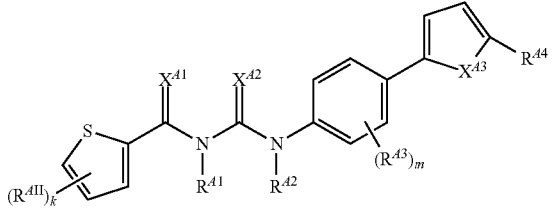

(A-VIII-a)

-continued

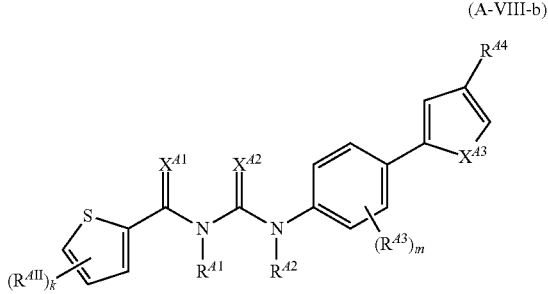
(A-VIII-b)

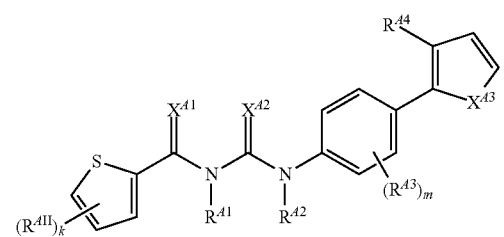
(A-VIII-c)

and pharmaceutically acceptable salts, solvates, hydrates, polymorphs, co-crystals, tautomers, stereoisomers, isotopically labeled derivatives, and prodrugs thereof, wherein $X^{A1}$, $X^{A2}$, $X^{A3}$, $R^{A1}$, $R^{A2}$, $R^{A3}$, $R^{A4}$, $R^{AII}$, k, and m are as defined herein.

In certain embodiments of Formula (A-VI), provided is a compound of any of the formulae:

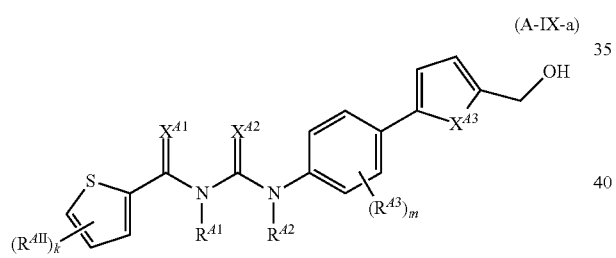
(A-IX-a)

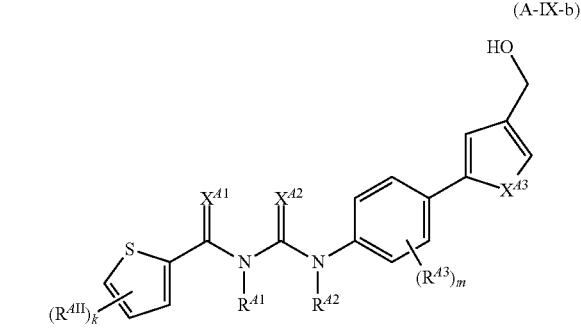
(A-IX-b)

(A-IX-c)

and pharmaceutically acceptable salts, solvates, hydrates, polymorphs, co-crystals, tautomers, stereoisomers, isotopically labeled derivatives, and prodrugs thereof, wherein $X^{A1}$, $X^{A2}$, $X^{A3}$, $R^{A1}$, $R^{A2}$, $R^{A3}$, $R^{AII}$, k, and m are as defined herein.

In certain embodiments, provided is a compound of any of the formulae:

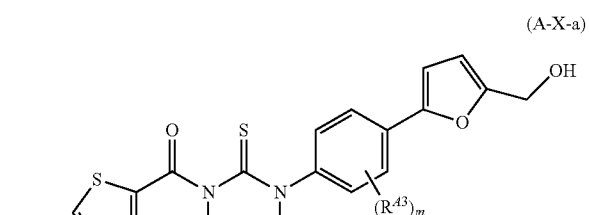
(A-X-a)

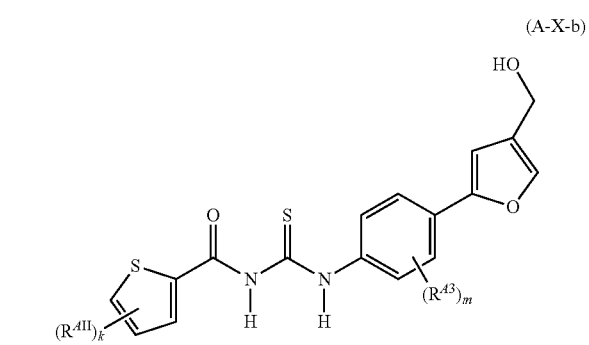
(A-X-b)

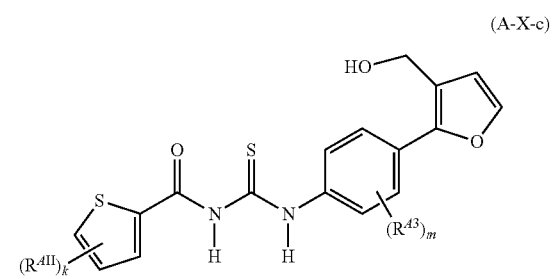
(A-X-c)

and pharmaceutically acceptable salts, solvates, hydrates, polymorphs, co-crystals, tautomers, stereoisomers, isotopically labeled derivatives, and prodrugs thereof, wherein $R^{A3}$, $R^{AII}$, k, and m are as defined herein.

In a certain embodiment, the compound of Formula (A) is not of the formula:

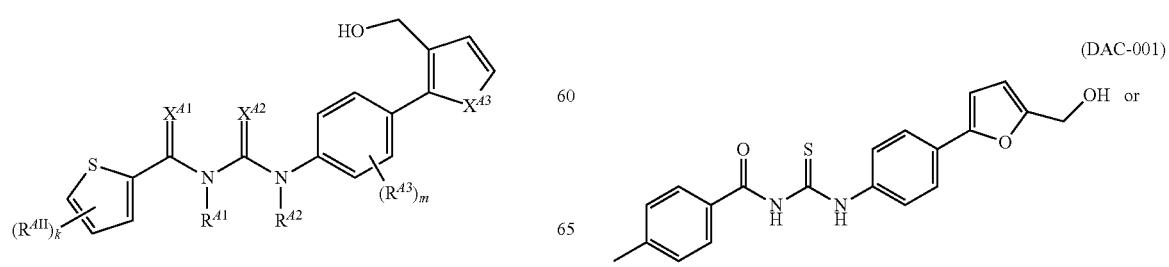
(DAC-001)

-continued

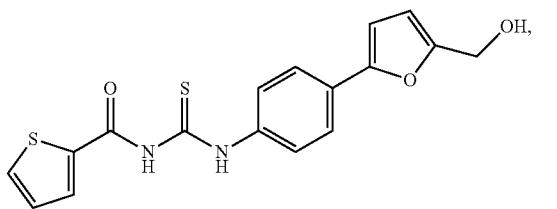

(DAC-002)

or a pharmaceutically acceptable salt thereof.

Another hit from the library was identified with a structural framework as shown in Formula (B):

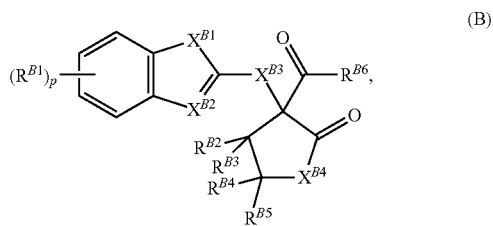

(B)

Therefore, in certain embodiments, provided is a compound of Formula (B), and pharmaceutically acceptable salts, solvates, hydrates, polymorphs, co-crystals, tautomers, stereoisomers, isotopically labeled derivatives, and prodrugs thereof, wherein each instance of $X^{B1}$, $X^{B3}$, and $X^{B4}$ is independently oxygen, sulfur, $NR^{B4a}$, or $C(R^{B4b})_2$ wherein $R^{B4a}$ is hydrogen, a nitrogen protecting group, or $C_{1-6}$ alkyl, and each occurrence of $R^{B4b}$ is hydrogen, halogen, or $C_{1-6}$ alkyl, or two $R^{B4b}$ groups are joined to form an optionally substituted carbocyclic or heterocyclic ring;

$X^{B2}$ is nitrogen or $CR^{B2a}$, wherein $R^{B2a}$ is hydrogen, halogen, or $C_{1-6}$ alkyl;

each instance of $R^{B1}$ is independently selected from the group consisting of halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{B1a}$, $-N(R^{B1b})_2$, $-SR^{B1a}$, $-C(=O)R^{B1a}$, $-C(=O)OR^{B1a}$, $-C(=O)SR^{B1a}$, $-C(=O)N(R^{B1b})_2$, $-OC(=O)R^{B1a}$, $-OC(=O)OR^{B1a}$, $-OC(=O)SR^{B1a}$, $-OC(=O)N(R^{B1b})_2$, $-NR^{B1b}C(=O)R^{B1b}$, $-NR^{B1b}C(=O)OR^{B1a}$, $-NR^{B1b}C(=O)SR^{B1a}$, $-NR^{B1b}C(=O)N(R^{B1b})_2$, $-SC(=O)R^{B1a}$, $-SC(=O)OR^{B1a}$, $-SC(=O)SR^{B1a}$, $-SC(=O)N(R^{B1b})_2$, $-C(=NR^{B1b})R^{B1a}$, $-C(=NR^{B1b})OR^{B1}$, $-C(=NR^{B1b})SR^{B1a}$, $-C(=NR^{B1b})N(R^{B1b})_2$, $-OC(=NR^{B1b})R^{B1a}$, $-OC(=NR^{B1b})OR^{B1a}$, $-OC(=NR^{B1b})SR^{B1a}$, $-OC(=NR^{B1b})N(R^{B1b})_2$, $-NR^{B1b}C(=NR^{B1b})R^{B1b}$, $-NR^{B1b}C(=NR^{B1b})OR^{B1a}$, $-NR^{B1b}C(=NR^{B1b})SR^{B1a}$, $-NR^{B1b}C(=NR^{B1b})N(R^{B1b})_2$, $-SC(=NR^{B1b})R^{B1a}$, $-SC(=NR^{B1b})OR^{B1a}$, $-SC(=NR^{B1b})SR^{B1a}$, $-SC(=NR^{B1b})N(R^{B1b})_2$, $-C(=S)R^{B1a}$, $-C(=S)OR^{B1a}$, $-C(=S)SR^{B1a}$, $-C(=S)N(R^{B1b})_2$, $-OC(=S)R^{B1a}$, $-OC(=S)OR^{B1a}$, $-OC(=S)SR^{B1a}$, $-OC(=S)N(R^{B1b})_2$, $-NR^{B1b}C(=S)R^{B1b}$, $-NR^{B1b}C(=S)OR^{B1a}$, $-NR^{B1b}C(=S)SR^{B1a}$, $-NR^{B1b}C(=S)N(R^{B1b})_2$, $-SC(=S)R^{B1a}$, $-SC(=S)OR^{B1a}$, $-SC(=S)$ $SR^{B1a}$, $-SC(=S)N(R^{B1b})_2$, $-S(=O)R^{B1a}$, $-SO_2R^{B1a}$, $-NR^{B1b}SO_2R^{B1a}$, $-SO_2N(R^{B1b})_2$, $-CN$, $-SCN$, and $-NO_2$, wherein each occurrence of $R^{B1a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, and each occurrence of $R^{B1b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{B1b}$ groups are joined to form an optionally substituted heterocyclic ring;

each instance of $R^{B2}$, $R^{B3}$, $R^{B4}$, and $R^{B5}$ is independently hydrogen, halogen, or $C_{1-6}$ alkyl;

$R^{B6}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{B6a}$, $-N(R^{B6b})_2$, or $-SR^{B6a}$, wherein each occurrence of $R^{B6a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, and each occurrence of $R^{B6b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{B6b}$ groups are joined to form an optionally substituted heterocyclic ring;

p is 0, 1, 2, 3, or 4.

In certain embodiments, $X^{B1}$ is oxygen. In certain embodiments, $X^{B1}$ is sulfur. In certain embodiments, $X^{B1}$ is $NR^{B4a}$, wherein $NR^{B4a}$ is as defined herein. In certain embodiments, $X^{B1}$ is NH. In certain embodiments, $X^{B1}$ is $C(R^{B4b})^2$, wherein $R^{B4b}$ is defined herein.

In certain embodiments, $X^{B2}$ is nitrogen. In certain embodiments, $X^{B2}$ is $CR^{B2a}$, wherein $R^{B2a}$ is as defined herein.

In certain embodiments, $X^{B3}$ is oxygen. In certain embodiments, $X^{B3}$ is sulfur. In certain embodiments, $X^{B3}$ is $NR^{B4a}$, wherein $NR^{B4a}$ is as defined herein. In certain embodiments, $X^{B3}$ is NH. In certain embodiments, $X^{B3}$ is $C(R^{B4b})_2$, wherein $R^{B4b}$ is defined herein.

In certain embodiments, $X^{B4}$ is oxygen. In certain embodiments, $X^{B4}$ is sulfur. In certain embodiments, $X^{B4}$ is $NR^{B4a}$, wherein $NR^{B4a}$ is as defined herein. In certain embodiments, $X^{B4}$ is NH. In certain embodiments, $X^{B4}$ is $C(R^{B4b})^2$, wherein $R^{B4b}$ is defined herein.

In certain embodiments, $X^{B1}$ is NH, and $X^{B2}$ is nitrogen.

In certain embodiments, one or more $R^{B1}$ is independently selected from the group consisting of halogen, optionally substituted alkyl, optionally substituted alkenyl, optionally substituted alkynyl, optionally substituted carbocyclyl, optionally substituted heterocyclyl, optionally substituted aryl, optionally substituted heteroaryl. In certain embodiments, one or more $R^{B1}$ is independently halogen. In certain embodiments, one or more $R^{B1}$ is independently $C_{1-6}$ alkyl.

In certain embodiments, $R^{B2}$ is hydrogen. In certain embodiments, $R^{B2}$ is halogen. In certain embodiments, $R^{B2}$ is fluorine. In certain embodiments, $R^{B2}$ is chlorine. In certain embodiments, $R^{B2}$ is bromine. In certain embodiments, $R^{B2}$ is iodine. In certain embodiments, $R^{B2}$ is $C_{1-6}$ alkyl. In certain embodiments, $R^{B2}$ is methyl. In certain embodiments, $R^{B2}$ is ethyl. In certain embodiments, $R^{B2}$ is propyl. In certain embodiments, $R^{B2}$ is butyl.

In certain embodiments, $R^{B3}$ is hydrogen. In certain embodiments, $R^{B3}$ is halogen. In certain embodiments, $R^{B3}$ is fluorine. In certain embodiments, $R^{B3}$ is chlorine. In certain embodiments, $R^{B3}$ is bromine. In certain embodiments, $R^{B3}$ is iodine. In certain embodiments, $R^{B3}$ is $C_{1-6}$ alkyl. In certain embodiments, $R^{B3}$ is methyl. In certain embodiments, $R^{B3}$ is ethyl. In certain embodiments, $R^{B3}$ is propyl. In certain embodiments, $R^{B3}$ is butyl.

In certain embodiments, $R^{B4}$ is hydrogen. In certain embodiments, $R^{B4}$ is halogen. In certain embodiments, $R^{B4}$ is fluorine. In certain embodiments, $R^{B4}$ is chlorine. In certain embodiments, $R^{B4}$ is bromine. In certain embodiments, $R^{B4}$ is iodine. In certain embodiments, $R^{B4}$ is $C_{1-6}$ alkyl. In certain embodiments, $R^{B4}$ is methyl. In certain embodiments, $R^{B4}$ is ethyl. In certain embodiments, $R^{B4}$ is propyl. In certain embodiments, $R^{B4}$ is butyl.

In certain embodiments, $R^{B5}$ is hydrogen. In certain embodiments, $R^{B5}$ is halogen. In certain embodiments, $R^{B5}$ is fluorine. In certain embodiments, $R^{B5}$ is chlorine. In certain embodiments, $R^{B5}$ is bromine. In certain embodiments, $R^{B5}$ is iodine. In certain embodiments, $R^{B5}$ is $C_{1-6}$ alkyl. In certain embodiments, $R^{B5}$ is methyl. In certain embodiments, $R^{B5}$ is ethyl. In certain embodiments, $R^{B5}$ is propyl. In certain embodiments, $R^{B5}$ is butyl.

In certain embodiments, $R^{B6}$ is hydrogen. In certain embodiments, $R^{B6}$ is optionally substituted alkyl. In certain embodiments, $R^{B6}$ is optionally substituted $C_{1-6}$ alkyl. In certain embodiments, $R^{B6}$ is methyl. In certain embodiments, $R^{B6}$ is ethyl. In certain embodiments, $R^{B6}$ is propyl. In certain embodiments, $R^{B6}$ is butyl. In certain embodiments, $R^{B6}$ is pentyl. In certain embodiments, $R^{B6}$ is hexyl.

In certain embodiments, p is 0. In certain embodiments, p is 1. In certain embodiments, p is 2. In certain embodiments, p is 3. In certain embodiments, p is 4.

In certain embodiments of Formula (B), wherein p is 1, provided is a compound of any one of the formulae:

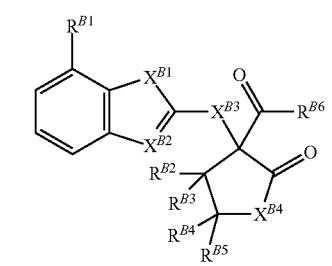
(B-I-a)

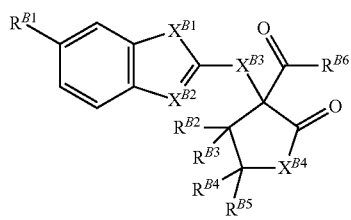
(B-I-b)

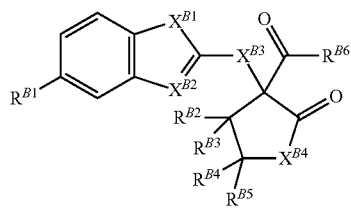
(B-I-c)

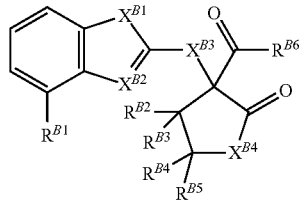
(B-I-d)

and pharmaceutically acceptable salts, solvates, hydrates, polymorphs, co-crystals, tautomers, stereoisomers, isotopically labeled derivatives, and prodrugs thereof, wherein $X^{B1}$, $X^{B2}$, $X^{B3}$, $X^{B4}$, $R^{B1}$, $R^{B2}$, $R^{B3}$, $R^{B4}$, $R^{B5}$, and $R^{B6}$ are as defined herein.

In certain embodiments, provided is a compound of Formula (B-II):

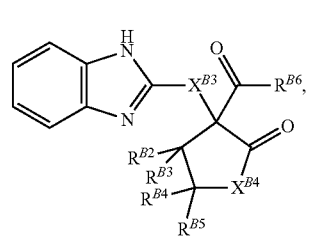
(B-II)

and pharmaceutically acceptable salts, solvates, hydrates, polymorphs, co-crystals, tautomers, stereoisomers, isotopically labeled derivatives, and prodrugs thereof, wherein $X^{B3}$, $X^{B4}$, $R^{B2}$, $R^{B3}$, $R^{B4}$, $R^{B5}$, and $R^{B6}$ are as defined herein.

In certain embodiments, provided is a compound of Formula (B-III):

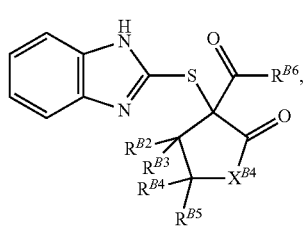
(B-III)

and pharmaceutically acceptable salts, solvates, hydrates, polymorphs, co-crystals, tautomers, stereoisomers, isotopically labeled derivatives, and prodrugs thereof, wherein $X^{B4}$, $R^{B2}$, $R^{B3}$, $R^{B4}$, $R^{B5}$, and $R^{B6}$ are as defined herein.

In certain embodiments, provided is a compound of Formula (B-IV):

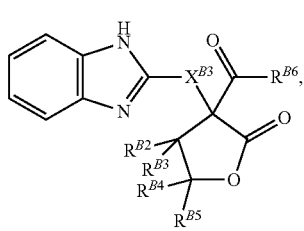
(B-IV)

In certain embodiments, provided is a compound of Formula (B-V):

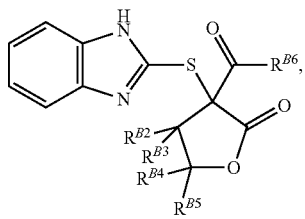
(B-V)

and pharmaceutically acceptable salts, solvates, hydrates, polymorphs, co-crystals, tautomers, stereoisomers, isotopically labeled derivatives, and prodrugs thereof, wherein $R^{B2}$, $R^{B3}$, $R^{B4}$, $R^{B5}$, and $R^{B6}$ are as defined herein.

In certain embodiments, provided is a compound of Formula (B-VI):

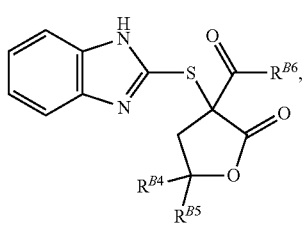
(B-VI)

and pharmaceutically acceptable salts, solvates, hydrates, polymorphs, co-crystals, tautomers, stereoisomers, isotopically labeled derivatives, and prodrugs thereof, wherein $R^{B4}$, $R^{B5}$, and $R^{B6}$ are as defined herein.

In certain embodiments, provided is a compound of Formula (B-VII):

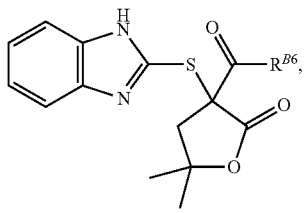
(B-VII)

and pharmaceutically acceptable salts, solvates, hydrates, polymorphs, co-crystals, tautomers, stereoisomers, isotopically labeled derivatives, and prodrugs thereof, wherein $R^{B6}$ is as defined herein.

In certain embodiments, provided is a compound of Formula (B-VIII):

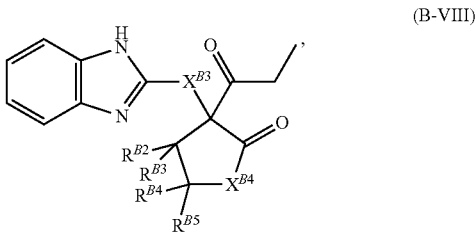
(B-VIII)

and pharmaceutically acceptable salts, solvates, hydrates, polymorphs, co-crystals, tautomers, stereoisomers, isotopically labeled derivatives, and prodrugs thereof, wherein $X^{B3}$, $X^{B4}$, $R^{B2}$, $R^{B3}$, $R^{B4}$, and $R^{B5}$ are as defined herein.

In certain embodiments, provided is a compound of Formula (B-IX):

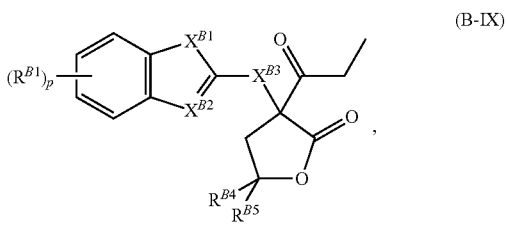
(B-IX)

and pharmaceutically acceptable salts, solvates, hydrates, polymorphs, co-crystals, tautomers, stereoisomers, isotopically labeled derivatives, and prodrugs thereof, wherein $X^{B1}$, $X^{B2}$, $X^{B3}$, $R^{B3}$, $R^{B4}$, and $R^{B5}$ are as defined herein.

In a certain embodiment, the compound of Formula (B) is not of the formula:

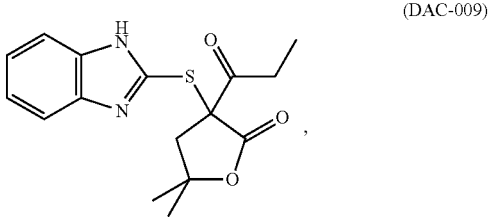 [SMILES: CCC(=O)C1(Sc2nc3ccccc3[nH]2)CC(C)(C)OC1=O]
(DAC-009)

or a pharmaceutically acceptable salt thereof.

Another hit from the library was identified with a structural framework as shown in Formula (C):

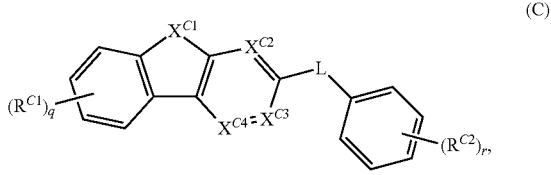
(C)

Therefore, in certain embodiments, provided is a compound of Formula (C), and pharmaceutically acceptable salts, solvates, hydrates, polymorphs, co-crystals, tautomers, stereoisomers, isotopically labeled derivatives, and prodrugs thereof, wherein $X^{C1}$ is oxygen, sulfur, or $NR^{C1a}$, wherein $R^{C1a}$ is hydrogen, a nitrogen protecting group, or $C_{1-6}$ alkyl;

each instance of $X^{C2}$, $X^{C3}$, and $X^{C4}$ is independently nitrogen or $CR^{C4a}$, wherein $R^{C4a}$ is hydrogen, halogen, or $C_{1-6}$ alkyl;

L is a bond; cyclic or acyclic, substituted or unsubstituted alkylene; cyclic or acyclic, substituted or unsubstituted alkenylene; cyclic or acyclic, substituted or unsubstituted alkynylene; cyclic or acyclic, substituted or unsubstituted heteroalkylene; cyclic or acyclic, substituted or unsubstituted heteroalkenylene; cyclic or acyclic, substituted or unsubstituted heteroalkynylene; substituted or unsubstituted arylene; or substituted or unsubstituted heteroarylenelene;

each instance of $R^{C1}$ and $R^{C2}$ is independently selected from the group consisting of halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{C2a}$, $-N(R^{C2b})_2$, $-SR^{C2a}$, $-C(=O)R^{C2a}$, $-C(=O)OR^{C2a}$, $-C(=O)SR^{C2a}$, $-C(=O)N(R^{C2b})_2$, $-OC(=O)R^{C2a}$, $-OC(=O)OR^{C2a}$, $-OC(=O)SR^{C2a}$, $-OC(=O)N(R^{C2b})_2$, $-NR^{C2b}C(=O)R^{C2b}$, $-NR^{C2b}C(=O)OR^{C2a}$, $-NR^{C2b}C(=O)SR^{C2a}$, $-NR^{C2b}C(=O)N(R^{C2b})_2$, $-SC(=O)R^{C2a}$, $-SC(=O)OR^{C2a}$, $-SC(=O)SR^{C2a}$, $-SC(=O)N(R^{C2b})_2$, $-C(=NR^{C2b})R^{C2a}$, $-C(=NR^{C2b})OR^{C2a}$, $-C(=NR^{C2b})SR^{C2a}$, $-C(=NR^{C2b})N(R^{C2b})_2$, $-OC(=NR^{C2b})R^{C2a}$, $-OC(=NR^{C2b})OR^{C2a}$, $-OC(=NR^{C2b})SR^{C2a}$, $-OC(=NR^{C2b})N(R^{C2b})_2$, $-NR^{C2b}C(=NR^{C2b})R^{C2b}$, $-NR^{C2b}C(=NR^{C2b})OR^{C2a}$, $-NR^{C2b}C(=NR^{C2b})SR^{C2a}$, $-NR^{C2b}C(=NR^{C2b})N(R^{C2b})_2$, $-SC(=NR^{C2b})R^{C2a}$, $-SC(=NR^{C2b})OR^{C2a}$, $-SC(=NR^{C2b})SR^{C2a}$, $-SC(=NR^{C2b})N(R^{C2b})_2$, $-C(=S)R^{C2a}$, $-C(=S)OR^{C2a}$, $-C(=S)SR^{C2a}$, $-C(=S)N(R^{C2b})_2$, $-OC(=S)R^{C2a}$, $-OC(=S)OR^{C2a}$, $-OC(=S)SR^{C2a}$, $-OC(=S)N(R^{C2b})_2$, $-NR^{C2b}C(=S)R^{C2b}$, $-NR^{C2b}C(=S)OR^{C2a}$, $-NR^{C2b}C(=S)SR^{C2a}$, $-NR^{C2b}C(=S)N(R^{C2b})_2$, $-SC(=S)R^{C2a}$, $-SC(=S)OR^{C2a}$, $-SC(=S)SR^{C2a}$, $-SC(=S)N(R^{C2b})_2$, $-S(=O)R^{C2a}$, $-SO_2R^{C2a}$, $-NR^{C2b}SO_2R^{C2a}$, $-SO_2N(R^{C2b})_2$, $-CN$, $-SCN$, and $-NO_2$, wherein each occurrence of $R^{C2a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, and each occurrence of $R^{C2b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{C2b}$ groups are joined to form an optionally substituted heterocyclic ring;

q is 0, 1, 2, 3, or 4;

r is 0, 1, 2, 3, 4, or 5, and

In certain embodiments, $X^{C1}$ is $NR^{C1a}$, wherein $R^{C1a}$ is hydrogen, a nitrogen protecting group, or $C_{1-6}$ alkyl. In certain embodiments, $X^{C1}$ is NH. In certain embodiments, $X^{C1}$ is oxygen. In certain embodiments, $X^{C1}$ is sulfur.

In certain embodiments, $X^{C2}$ is nitrogen. In certain embodiments, $X^{C2}$ is $CR^{C4a}$. In certain embodiments, $X^{C3}$ is nitrogen. In certain embodiments, $X^{C3}$ is $CR^{C4a}$. In certain embodiments, $X^{C4}$ is nitrogen. In certain embodiments, $X^{C4}$ is $CR^{C4a}$. In any of the above described embodiments, each instance of $R^{C4a}$ is independently nitrogen or $CR^{C4a}$, wherein $R^{C4a}$ is hydrogen, halogen, or $C_{1-6}$ alkyl.

In certain embodiments, L is a bond. In certain embodiments, L is cyclic or acyclic, substituted or unsubstituted alkylene. In certain embodiments, L is cyclic or acyclic, substituted or unsubstituted alkenylene. In certain embodiments, L is cyclic or acyclic, substituted or unsubstituted alkynylene. In certain embodiments, L is cyclic or acyclic, substituted or unsubstituted heteroalkylene. In certain embodiments, L is cyclic or acyclic, substituted or unsubstituted heteroalkenylene. In certain embodiments, L is cyclic or acyclic, substituted or unsubstituted heteroalkynylene. In certain embodiments, L is substituted or unsubstituted arylene. In certain embodiments, L is substituted or unsubstituted heteroarylene.

In certain embodiments, wherein L is substituted or unsubstituted heteroalkenylene, L comprises at least 5 atoms which are not hydrogen. In certain embodiments, wherein L is substituted or unsubstituted heteroalkenylene, L comprises at least 4 atoms which are not hydrogen. In certain embodiments, wherein L is substituted or unsubstituted heteroalkenylene, L comprises at least 3 atoms which are not hydrogen. In certain embodiments, wherein L is substituted or unsubstituted heteroalkenylene, L comprises at least 2 atoms which are not hydrogen.

In certain embodiments, each instance of $R^{C1}$ is independently selected from the group consisting of halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl. In certain embodiments, at least one $R^{C1}$ is $C_{1-6}$ alkyl. In certain embodiments, at least one $R^{C1}$ is methyl. In certain embodiments, at least one $R^{C1}$ is ethyl. In certain embodiments, at least one $R^{C1}$ is propyl. In certain embodiments, at least one $R^{C1}$ is butyl.

In certain embodiments, q is 0. In certain embodiments, q is 1. In certain embodiments, q is 2. In certain embodiments, q is 3. In certain embodiments, q is 4.

In certain embodiments, r is 0. In certain embodiments, r is 1. In certain embodiments, r is 2. In certain embodiments, r is 3. In certain embodiments, r is 4. In certain embodiments, r is 5.

In certain embodiments, $X^{C1}$, $X^{C2}$, $X^{C3}$, and $X^{C4}$ are nitrogen.

In certain embodiments, provided is a compound of Formula (C-I):

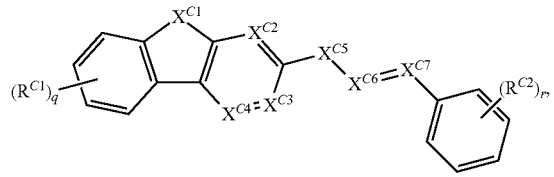

(C-I)

and pharmaceutically acceptable salts, solvates, hydrates, polymorphs, co-crystals, tautomers, stereoisomers, isotopically labeled derivatives, and prodrugs thereof, wherein $X^{C1}$, $X^{C2}$, $X^{C3}$, $X^{C4}$, $R^{C1}$, $R^{C2}$, q, and r are as defined herein;

$X^{C5}$ is oxygen, sulfur, $NR^{C5a}$, or $C(R^{C5b})_2$, wherein $R^{C5a}$ is hydrogen or $C_{1-6}$ alkyl, and each occurrence of $R^{C5b}$ is hydrogen, halogen, or $C_{1-6}$ alkyl, or two $R^{C5b}$ groups are joined to form an optionally substituted carbocyclic or heterocyclic ring; and each instance of $X^{C6}$ and $X^{C7}$ is independently nitrogen or $CR^{C7a}$, wherein $R^{C7a}$ is hydrogen, halogen, or $C_{1-6}$ alkyl.

In certain embodiments of Formula (C-I), or a pharmaceutically acceptable salt thereof, $X^{C5}$ is NH. In certain embodiments of Formula (C-I), or a pharmaceutically acceptable salt thereof, $X^{C5}$ is $NR^{C5a}$, wherein $R^{C5a}$ is as defined herein.

In certain embodiments of Formula (C-I), or a pharmaceutically acceptable salt thereof, $X^{C6}$ is nitrogen.

In certain embodiments of Formula (C-I), or a pharmaceutically acceptable salt thereof, $X^{C7}$ is CH. In certain embodiments of Formula (C-I), or a pharmaceutically acceptable salt thereof, $X^{C7}$ is $C(R^{C5b})_2$, wherein $R^{C5b}$ is as defined herein.

In certain embodiments of Formula (C-I), provided is a compound of Formula (C-II):

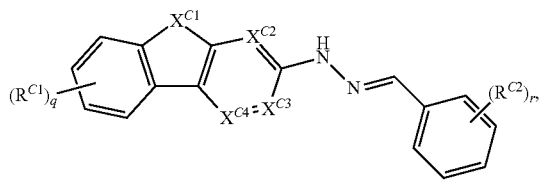

(C-II)

and pharmaceutically acceptable salts, solvates, hydrates, polymorphs, co-crystals, tautomers, stereoisomers, isotopically labeled derivatives, and prodrugs thereof, wherein $X^{C1}$, $X^{C2}$, $X^{C3}$, $X^{C4}$, $R^{C1}$, $R^{C2}$, q, and r are as defined herein.

In certain embodiments, provided is a compound of Formula (C-III):

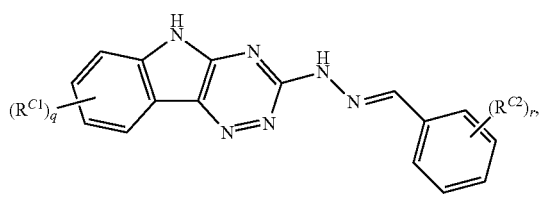

(C-III)

and pharmaceutically acceptable salts, solvates, hydrates, polymorphs, co-crystals, tautomers, stereoisomers, isotopically labeled derivatives, and prodrugs thereof, wherein $R^{C1}$, $R^{C2}$, q, and r are as defined herein.

In certain embodiments of Formula (C-III), wherein q is 1, provided is a compound of any of the formulae:

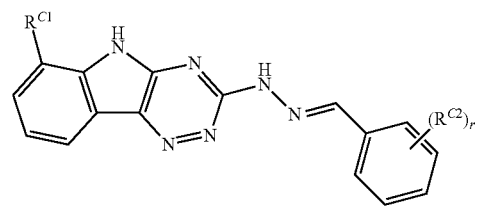

(C-III-a)

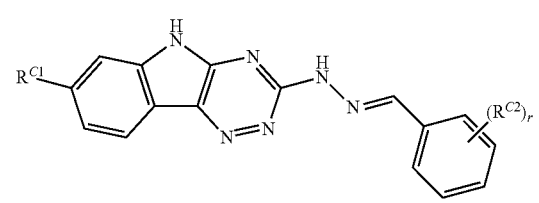

(C-III-b)

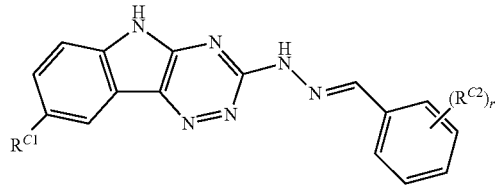

(C-III-c)

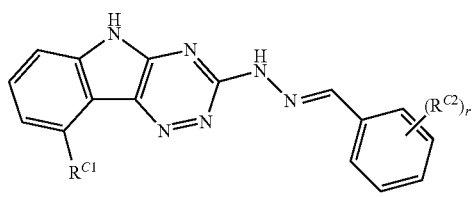

(C-III-d)

and pharmaceutically acceptable salts, solvates, hydrates, polymorphs, co-crystals, tautomers, stereoisomers, isotopically labeled derivatives, and prodrugs thereof, wherein $R^{C1}$, $R^{C2}$, and r are as defined herein.

In certain embodiments of the formulae (C-III-a), (C-III-b), (C-III-c), and (C-III-d), or a pharmaceutically acceptable salt thereof, wherein $R^{C2}$ and r are as defined herein, $R^{C1}$ is $C_{1-6}$ alkyl. In certain embodiments of the formulae (C-III-a), (C-III-b), (C-III-c), and (C-III-d), or a pharmaceutically acceptable salt thereof, wherein $R^{C2}$ and r are as defined herein, $R^{C1}$ is methyl. In certain embodiments of the formulae (C-III-a), (C-III-b), (C-III-c), and (C-III-d), or a pharmaceutically acceptable salt thereof, wherein $R^{C2}$ and r are as defined herein, $R^{C1}$ is ethyl. In certain embodiments of the formulae (C-III-a), (C-III-b), (C-III-c), and (C-III-d), or a pharmaceutically acceptable salt thereof, wherein $R^{C2}$ and r are as defined herein, $R^{C1}$ propyl. In certain embodiments of the formulae (C-III-a), (C-III-b), (C-III-c), and (C-III-d), or a pharmaceutically acceptable salt thereof, wherein $R^{C2}$ and r are as defined herein, $R^{C1}$ is butyl.

In certain embodiments, provided is a compound of Formula (C-IV):

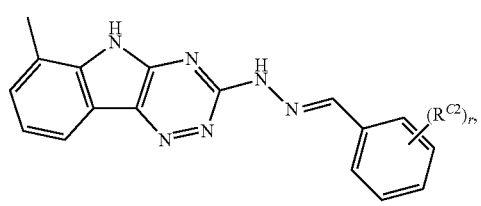

(C-IV)

and pharmaceutically acceptable salts, solvates, hydrates, polymorphs, co-crystals, tautomers, stereoisomers, isotopically labeled derivatives, and prodrugs thereof, wherein $R^{C2}$ and r are as defined herein.

In certain embodiments, provided is a compound of Formula (C-V):

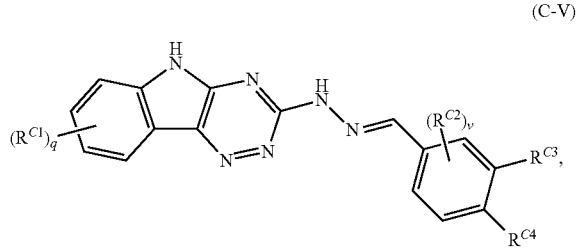

(C-V)

and pharmaceutically acceptable salts, solvates, hydrates, polymorphs, co-crystals, tautomers, stereoisomers, isotopically labeled derivatives, and prodrugs thereof, wherein each instance of $R^{C3}$ and $R^{C4}$ is independently selected from the group consisting of halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{C4a}$, —$N(R^{C4b})_2$, —$SR^{C4a}$, —$C(=O)R^{C4a}$, —$C(=O)OR^{C4a}$, —$C(=O)SR^{C4a}$, —$C(=O)N(R^{C4b})_2$, —$OC(=O)R^{C4a}$, —$OC(=O)OR^{C4a}$, —$OC(=O)SR^{C4a}$, —$OC(=O)N(R^{C4b})_2$, —$NR^{C4b}C(=O)R^{C4b}$, —$NR^{C4b}C(=O)OR^{C4a}$, —$NR^{C4b}C(=O)SR^{C4a}$, —$NR^{C4b}C(=O)N(R^{C4b})_2$, —$SC(=O)R^{C4a}$, —$SC(=O)OR^{C4a}$, —$SC(=O)SR^{C4a}$, —$SC(=O)N(R^{C4b})_2$, —$C(=NR^{C4b})R^{C4a}$, —$C(=NR^{C4b})OR^{C4a}$, —$C(=NR^{C4b})SR^{C4a}$, —$C(=NR^{C4b})N(R^{C4b})_2$, —$OC(=NR^{C4b})R^{C4a}$, —$OC(=NR^{C4b})OR^{C4a}$, —$OC(=NR^{C4b})SR^{C4a}$, —$OC(=NR^{C4b})N(R^{C4b})_2$, —$NR^{C4b}C(=NR^{C4b})R^{C4b}$, —$NR^{C4b}C(=NR^{C4b})OR^{C4a}$, —$NR^{C4b}C(=NR^{C4b})SR^{C4a}$, —$NR^{C4b}C(=NR^{C4b})N(R^{C4b})_2$, —$SC(=NR^{C4b})R^{C4a}$, —$SC(=NR^{C4b})OR^{C4a}$, —$SC(=NR^{C4b})SR^{C4a}$, —$SC(=NR^{C4b})N(R^{C4b})_2$, —$C(=S)R^{C4a}$, $C(=S)OR^{C4a}$, —$C(=S)SR^{C4a}$, —$C(=S)N(R^{C4b})_2$, —$OC(=S)R^{C4a}$, —$OC(=S)OR^{C4a}$, —$OC(=S)SR^{C4a}$, —$OC(=S)N(R^{C4b})_2$, —$NR^{C4b}C(=S)R^{C4b}$, —$NR^{C4b}C(=S)OR^{C4a}$, —$NR^{C4b}C(=S)SR^{C4a}$, —$NR^{C4b}C(=S)N(R^{C4b})_2$, —$SC(=S)R^{C4a}$, —$SC(=S)OR^{C4a}$, 13 $SC(=S)SR^{C4a}$, —$SC(=S)N(R^{C4b})^2$, —$S(=O)R^{C4a}$, —$SO_2R^{C4a}$, —$NR^{C4b}SO_2R^{C4a}$, —$SO_2N(R^{C4b})_2$, —CN, —SCN, and —$NO_2$, wherein each occurrence of $R^{C4a}$ independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, and each occurrence of $R^{C4b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{C4b}$ groups are joined to form an optionally substituted heterocyclic ring; and v is 0, 1, 2, or 3.

In certain embodiments, v is 0. In certain embodiments, v is 1. In certain embodiments, v is 2. In certain embodiments, v is 3.

In certain embodiments of Formula (C-V), wherein v is 1, provided is a compound of any of the formulae:

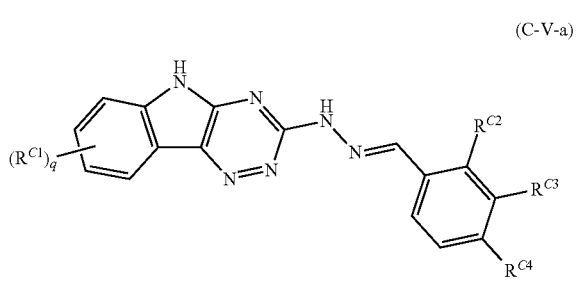

(C-V-a)

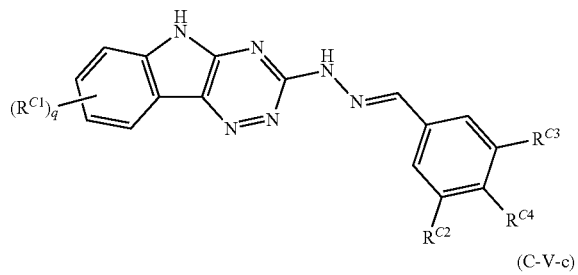

(C-V-b)

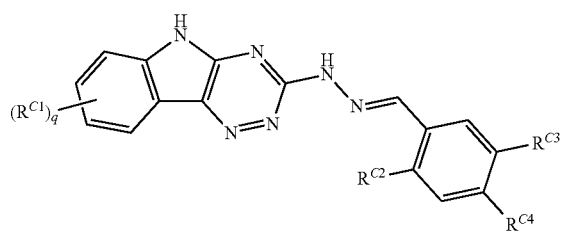

(C-V-c)

and pharmaceutically acceptable salts, solvates, hydrates, polymorphs, co-crystals, tautomers, stereoisomers, isotopically labeled derivatives, and prodrugs thereof, wherein $R^{C1}$, $R^{C2}$, $R^{C3}$, $R^{C4}$, and q are as defined herein.

In certain embodiments of the formulae (C-V-a), (C-V-b), and (C-V-c), or a pharmaceutically acceptable salt thereof, $R^{C2}$, $R^{C3}$, or $R^{C4}$ is hydroxyl, —$OR^{C2a}$, —$N(R^{C2b})_2$, or —$SR^{C2a}$, wherein $R^{C1}$, q, $R^{C2a}$, and $R^{C2b}$ are as defined herein. In certain embodiments of the formulae (C-V-a), (C-V-b), and (C-V-c), or a pharmaceutically acceptable salt thereof, $R^{C2}$ and $R^{C3}$ are independently hydroxyl, —$OR^{C2a}$, —$N(R^{C2b})_2$, or —$SR^{C2a}$, wherein $R^{C1}$, $R^{C4}$, q, $R^{C2a}$, and $R^{C2b}$ are as defined herein. In certain embodiments of the formulae (C-V-a), (C-V-b), and (C-V-c), or a pharmaceutically acceptable salt thereof, $R^{C2}$ and $R^{C4}$ are independently hydroxyl, —$OR^{C2a}$, —$N(R^{C2b})_2$, or —$SR^{C2a}$, wherein $R^{C1}$, $R^{C3}$, q, $R^{C2a}$, and $R^{C2b}$ are as defined herein. In certain embodiments of the formulae (C-V-a), (C-V-b), and (C-V-c), or a pharmaceutically acceptable salt thereof, $R^{C3}$ and $R^{C4}$ are independently hydroxyl, —$OR^{C2a}$, —$N(R^{C2b})_2$, or —$SR^{C2a}$, wherein $R^{C1}$, $R^{C2}$, q, $R^{C2a}$, and $R^{C2b}$ are as defined herein. In certain embodiments of the formulae (C-V-a), (C-V-b), and (C-V-c), or a pharmaceutically acceptable salt thereof, $R^{C2}$, $R^{C3}$, and $R^{C4}$ are independently hydroxyl, —$OR^{C2a}$, —$N(R^{C2b})_2$, or —$SR^{C2a}$, wherein $R^{C1}$, q, $R^{C2a}$, and $R^{C2b}$ are as defined herein.

In certain embodiments of Formula (C-V), provided is a compound of Formula (C-VI):

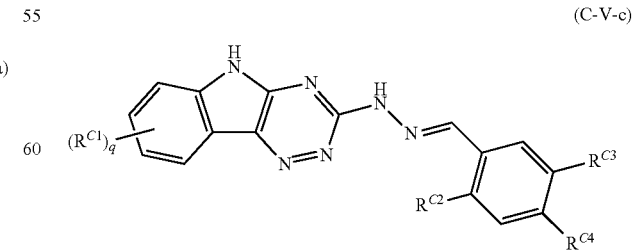

(C-V-c)

and pharmaceutically acceptable salts, solvates, hydrates, polymorphs, co-crystals, tautomers, stereoisomers, isotopically labeled derivatives, and prodrugs thereof, wherein $R^{C1}$, $R^{C3}$, $R^{C4}$, and q are as defined herein.

In certain embodiments of Formula (C-VI), or a pharmaceutically acceptable salt thereof, $R^{C3}$ is hydroxyl, $-OR^{C4a}$, $-N(R^{C4b})_2$, or $-SR^{C4a}$, wherein $R^{C1}$, $R^{C4}$, q, $R^{C4a}$, and $R^{C4b}$ are as defined herein. In certain embodiments of Formula (C-VI), or a pharmaceutically acceptable salt thereof, $R^{C4}$ is hydroxyl, $-OR^{C4a}$, $-N(R^{C4b})_2$, or $-SR^{C4a}$, wherein $R^{C1}$, $R^{C3}$, q, $R^{C4a}$, and $R^{C4b}$ are as defined herein. In certain embodiments of Formula (C-VI), or a pharmaceutically acceptable salt thereof, $R^{C3}$ and $R^{C4}$ are independently hydroxyl, $-OR^{C4a}$, $-N(R^{C4b})_2$, or $-SR^{C4a}$, wherein $R^{C1}$, q, $R^{C4a}$, and $R^{C4b}$ are as defined herein. In certain embodiments of Formula (C-VI), $R^{C3}$ and $R^{C4}$ are both hydroxyl, $-OR^{C4a}$, $-N(R^{C4b})_2$, or $-SR^{C4a}$, wherein $R^{C1}$, q, $R^{C4b}$ are as defined herein.

In certain embodiments of Formula (C-V), provided is a compound of Formula (C-VII):

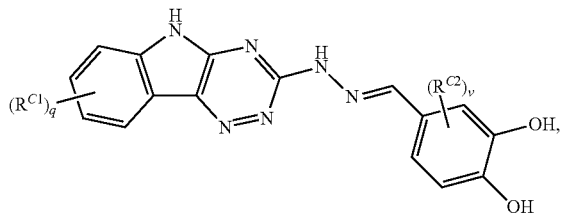

(C-VII)

and pharmaceutically acceptable salts, solvates, hydrates, polymorphs, co-crystals, tautomers, stereoisomers, isotopically labeled derivatives, and prodrugs thereof, wherein $R^{C1}$, $R^{C2}$, q, and v are as defined herein.

In certain embodiments of Formula (C-V), provided is a compound of Formula (C-VIII):

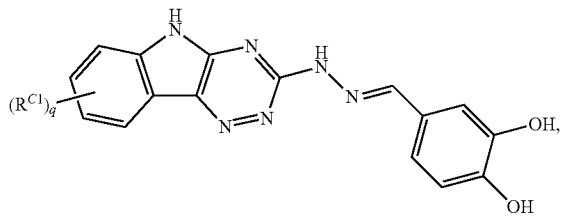

(C-VIII)

and pharmaceutically acceptable salts, solvates, hydrates, polymorphs, co-crystals, tautomers, stereoisomers, isotopically labeled derivatives, and prodrugs thereof, wherein $R^{C1}$ and q are as defined herein.

In certain embodiments of Formula (C-VIII), or a pharmaceutically acceptable salt thereof, each instance of $R^{C1}$ is $C_{1-6}$ alkyl. In certain embodiments of Formula (C-VIII), or a pharmaceutically acceptable salt thereof, each instance of $R^{C1}$ is methyl. In certain embodiments of Formula (C-VIII), or a pharmaceutically acceptable salt thereof, each instance of $R^{C1}$ is ethyl. In certain embodiments of Formula (C-VIII), or a pharmaceutically acceptable salt thereof, each instance of $R^{C1}$ is propyl. In certain embodiments of Formula (C-VIII), or a pharmaceutically acceptable salt thereof, each instance of $R^{C1}$ is butyl.

In certain embodiments of Formula (C-VIII), wherein q is 1, provided is a compound of any of the formulae:

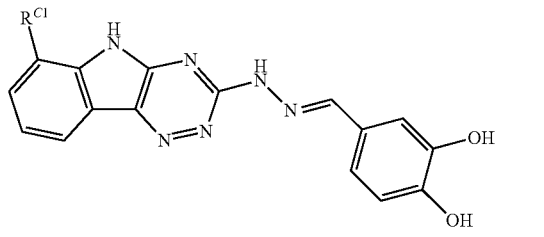

(C-VIII-a)

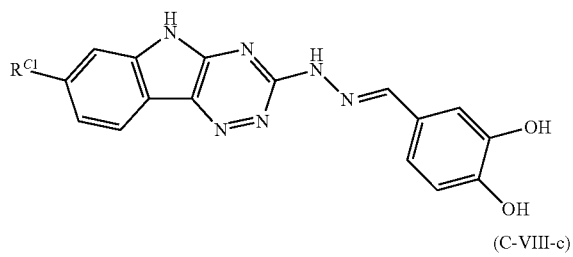

(C-VIII-b)

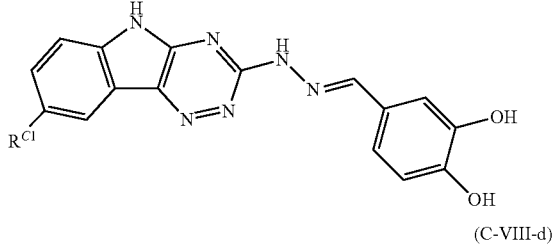

(C-VIII-c)

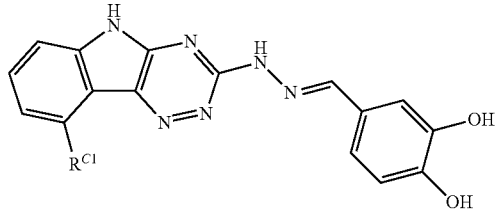

(C-VIII-d)

and pharmaceutically acceptable salts, solvates, hydrates, polymorphs, co-crystals, tautomers, stereoisomers, isotopically labeled derivatives, and prodrugs thereof, wherein $R^{C1}$ is as defined herein.

In certain embodiments, the compound of Formula (C) is not of the formula:

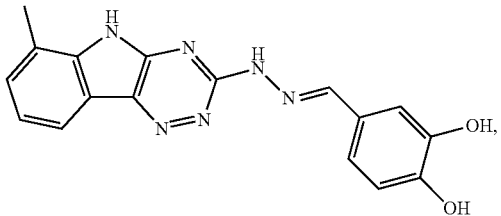

(DAC-003)

or a pharmaceutically acceptable salt thereof.

Another hit from the library was identified with a structural framework as shown in Formula (D):

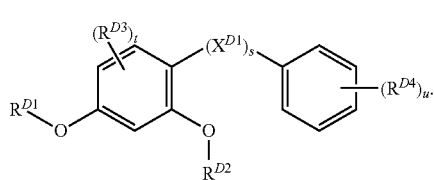

Therefore, in certain embodiments, provided is a compound of Formula (D), and pharmaceutically acceptable salts, solvates, hydrates, polymorphs, co-crystals, tautomers, stereoisomers, isotopically labeled derivatives, and prodrugs thereof, wherein each instance of $X^{D1}$ is independently oxygen, sulfur, $NR^{D1a}$, or $C(R^{D1b})_2$, wherein $R^{D1a}$ is hydrogen or $C_{1-6}$ alkyl, and each occurrence of $R^{D1b}$ is hydrogen, halogen, or $C_{1-6}$ alkyl, or two $R^{D1b}$ groups are joined to form an optionally substituted carbocyclic or heterocyclic ring;

s is 0, 1, 2, 3, 4, 5, or 6;

each instance of $R^{D1}$ and $R^{D2}$ is independently hydrogen, an oxygen protecting group, $C_{1-6}$ alkyl, $-C(=O)R^{D2a}$, $-C(=O)OR^{D2a}$, $-C(=O)SR^{D2a}$, $-C(=O)N(R^{D2b})_2$, $-S(=O)R^{D2a}$, or $-S(=O)_2R^{D2a}$, wherein each occurrence of $R^{D2a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, and each occurrence of $R^{D2b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{D2b}$ groups are joined to form an optionally substituted heterocyclic ring;

each instance of $R^{D3}$ and $R^{D4}$ is independently selected from the group consisting of halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{D4a}$, $-N(R^{D4b})_2$, $-SR^{D4a}$, $-C(=O)R^{D4a}$, $-C(=O)OR^{D4a}$, $-C(=O)SR^{D4a}$, $-C(=O)N(R^{D4b})_2$, $-OC(=O)R^{D4a}$, $-OC(=O)OR^{D4a}$, $-OC(=O)SR^{D4a}$, $-OC(=O)N(R^{D4b})_2$, $-NR^{D4b}C(=O)R^{D4b}$, $-NR^{D4b}C(=O)OR^{D4a}$, $-NR^{D4b}C(=O)SR^{D4a}$, $-NR^{D4b}C(=O)N(R^{D4b})_2$, $-SC(=O)R^{D4a}$, $-SC(=O)OR^{D4a}$, $-SC(=O)SR^{D4a}$, $-SC(=O)N(R^{D4b})_2$, $-C(=NR^{D4b})R^{D4a}$, $-C(=NR^{D4b})OR^{D4a}$, $-C(=NR^{D4b})SR^{D4a}$, $-C(=NR^{D4b})N(R^{D4b})_2$, $-OR(=NR^{D4b})R^{D4a}$, $-OC(=NR^{D4b})OR^{D4a}$, $-OC(=NR^{D4b})SR^{D4a}$, $-OC(=NR^{D4b})N(R^{D4b})_2$, $-NR^{D4b}C(=NR^{D4b})R^{D4b}$, $-NR^{D4b}C(=NR^{D4b})OR^{D4a}$, $-NR^{D4b}C(=NR^{D4b})SR^{D4a}$, $-NR^{D4b}C(=NR^{D4b})N(R^{D4b})_2$, $-SC(=NR^{D4b})R^{D4a}$, $-SC(=NR^{D4b})OR^{D4a}$, $-SC(=NR^{D4b})SR^{D4a}$, $-SC(=NR^{D4b})N(R^{D4b})_2$, $-C(=S)R^{D4a}$, $-C(=S)OR^{D4a}$, $-C(=S)SR^{D4a}$, $-C(=S)N(R^{D4b})_2$, $-OC(=S)R^{D4a}$, $-OC(=S)OR^{D4a}$, $-OC(=S)SR^{D4a}$, $-OC(=S)N(R^{D4b})_2$, $-NR^{D4b}C(=S)R^{D4b}$, $-NR^{D4b}C(=S)OR^{D4a}$, $-NR^{D4b}C(=S)SR^{D4a}$, $-NR^{D4b}C(=S)N(R^{D4b})_2$, $-SC(=S)R^{D4a}$, $-SC(=S)OR^{D4a}$, $-SC(=S)SR^{D4a}$, $-SC(=S)N(R^{D4b})_2$, $-S(=O)R^{D4a}$, $-SO_2R^{D4a}$, $-NR^{D4b}SO_2R^{D4a}$, $-SO_2N(R^{D4b})_2$, $-CN$, $-SCN$, and $-NO_2$, wherein each occurrence of $R^{D4a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, and each occurrence of $R^{D4b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two $R^{D4b}$ groups are joined to form an optionally substituted heterocyclic ring;

t is 0, 1, 2, or 3; and u is 0, 1, 2, 3, 4 or 5.

In certain embodiments, s is 0. In certain embodiments, s is 1. In certain embodiments, s is 2. In certain embodiments, s is 3. In certain embodiments, s is 4. In certain embodiments, s is 5. In certain embodiments, s is 6.

In certain embodiments of Formula (D), wherein s is 2, provided is a compound of Formula (D-I):

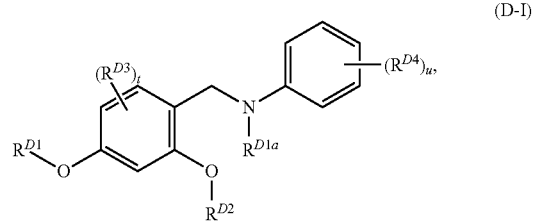

and pharmaceutically acceptable salts, solvates, hydrates, polymorphs, co-crystals, tautomers, stereoisomers, isotopically labeled derivatives, and prodrugs thereof, wherein $R^{D1}$, $R^{D2}$, $R^{D3}$, $R^{D4}$, $R^{D1a}$, t, and u are as defined herein.

In certain embodiments of Formula (D-I), provided is a compound of Formula (D-II):

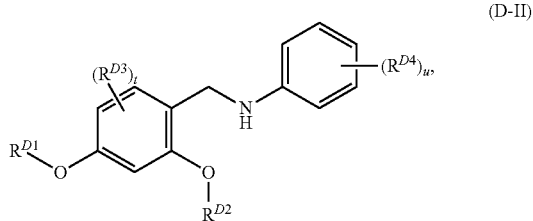

and pharmaceutically acceptable salts, solvates, hydrates, polymorphs, co-crystals, tautomers, stereoisomers, isotopically labeled derivatives, and prodrugs thereof, wherein $R^{D1}$, $R^{D2}$, $R^{D3}$, $R^{D4}$, t, and u are as defined herein.

In certain embodiments of Formula (D-II), or a pharmaceutically acceptable salt thereof, $R^{D1}$, $R^{D2}$, or both is $C_{1-6}$ alkyl. In certain embodiments of Formula (D-II), or a pharmaceutically acceptable salt thereof, $R^{D1}$, $R^{D2}$, or both is methyl. In certain embodiments of Formula (D-II), or a pharmaceutically acceptable salt thereof, $R^{D1}$, $R^{D2}$, or both is ethyl. In certain embodiments of Formula (D-II), or a pharmaceutically acceptable salt thereof, $R^{D1}$, $R^{D2}$, or both is propyl. In certain embodiments of Formula (D-II), or a pharmaceutically acceptable salt thereof, $R^{D1}$, $R^{D2}$, or both is butyl.

In certain embodiments of Formula (D-II), wherein t is 1, provided is a compound of any of the formulae:

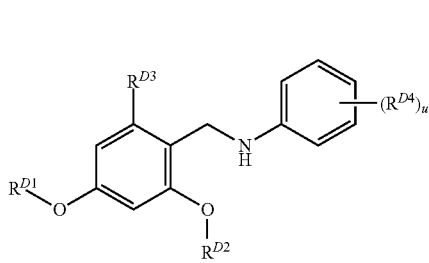
(D-II-a)

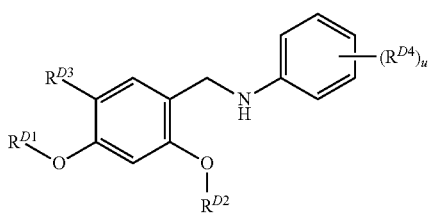
(D-II-b)

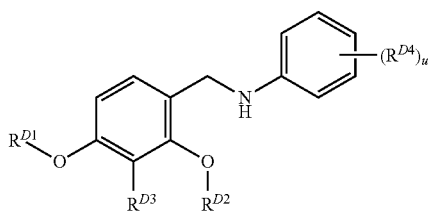
(D-II-c)

and pharmaceutically acceptable salts, solvates, hydrates, polymorphs, co-crystals, tautomers, stereoisomers, isotopically labeled derivatives, and prodrugs thereof, wherein $R^{D1}$, $R^{D2}$, $R^{D3}$, $R^{D4}$, and u are as defined herein.

In certain embodiments of Formula (D-II), provided is a compound of Formula (D-III):

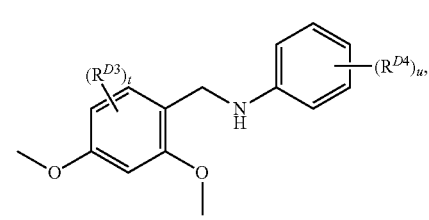
(D-III)

and pharmaceutically acceptable salts, solvates, hydrates, polymorphs, co-crystals, tautomers, stereoisomers, isotopically labeled derivatives, and prodrugs thereof, wherein $R^{D3}$, $R^{D4}$, t, and u are as defined herein.

In certain embodiments of Formula (D-III), wherein t is 1, provided is a compound of any of the formulae:

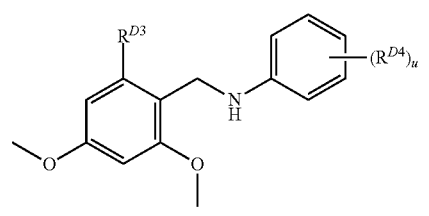
(D-III-a)

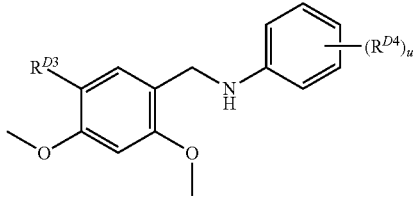
(D-III-b)

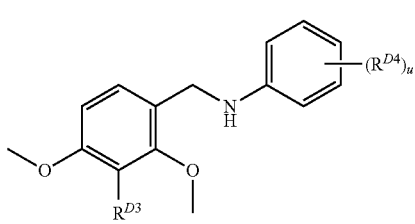
(D-IIIc)

and pharmaceutically acceptable salts, solvates, hydrates, polymorphs, co-crystals, tautomers, stereoisomers, isotopically labeled derivatives, and prodrugs thereof, wherein $R^{D3}$, $R^{D4}$, and u are as defined herein.

In certain embodiments of Formula (D), provided is a compound of Formula (D-III):

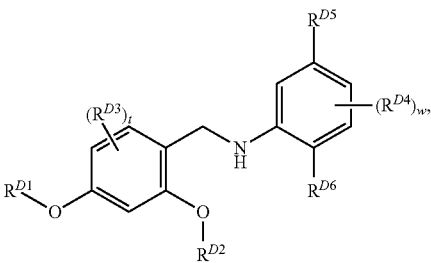
(D-IV)

and pharmaceutically acceptable salts, solvates, hydrates, polymorphs, co-crystals, tautomers, stereoisomers, isotopically labeled derivatives, and prodrugs thereof, wherein
$R^{D1}$, $R^{D2}$, $R^{D3}$, $R^{D4}$, and t are as defined herein;

each instance of $R^{D5}$ and $R^{D6}$ is independently selected from the group consisting of halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{D6a}$, —$N(R^{D6b})_2$, —$SR^{D6a}$, —$C(=O)R^{D6a}$, —$C(=O)OR^{D6a}$, —$C(=O)SR^{D6a}$, —$C(=O)N(R^{D6b})_2$, —$OC(=O)R^{D6a}$, —$OC(=O)OR^{D6a}$, —$OC(=O)SR^{D6a}$, —$OC(=O)N(R^{D6b})_2$, —$NR^{D6b}C(=O)R^{D6b}$, —$NR^{D6b}C(=O)OR^{D6a}$, —$NR^{D6b}C(=O)SR^{D6a}$, —$NR^{D6b}C(=O)N(R^{D6b})_2$, —$SC(=O)R^{D6a}$, —$SC(=O)OR^{D6a}$, —$SC(=O)SR^{D6a}$, —$SC(=O)N(R^{D6b})_2$, —$C(=NR^{D6b})R^{D6a}$, —$C(=NR^{D6b})OR^{D6a}$, —$C(=NR^{D6b})SR^{D6a}$, —$C)=NR^{D6b})N(R^{D6b})_2$, —$OC(=NR^{D6b})R^{D6a}$, —$OC(=NR^{D6b})OR^{D6a}$, —$OC(=NR^{D6b})SR^{D6a}$, —$OC(=NR^{D6b})N(R^{D6b})_2$, —$NR^{D6b}C(=NR^{D6b})R^{D6b}$, —$NR^{D6b}C(=NR^{D6b})OR^{D5a}$, —$NR^{D6b}C(=NR^{D6b})SR^{D6a}$, —$NR^{D6b}C(=NR^{D6b})N(R^{D6b})_2$, —$SC(=NR^{D6b})R^{D6a}$, —$SC(=NR^{D6b})OR^{D6a}$, —$SC(=NR^{D6b})SR^{D6a}$, —$SC(=NR^{D6b})N(R^{D6b})_2$, —$C(=S)R^{D6a}$, —$C(=S)OR^{D6a}$, —$C(=S)SR^{D6a}$, —$C(=S)N(R^{D6b})_2$, —$OC(=S)R^{D6a}$, —OC(=S)OR$^{D6a}$, —OC(=S)SR$^{D6a}$, —OC(=S)N(R$^{D6b}$)$_2$, —NR$^{D6b}$C(=S)R$^{D6b}$, —NR$^{D6b}$C(=S)OR$^{D6a}$, —NR$^{D6b}$C(=S)SR$^{D6a}$, —NR$^{D6b}$C(=S)N(R$^{D6b}$)$_2$, —SC(=S)R$^{D6a}$, —SC(=S)OR$^{D6a}$, —SC(=S)SR$^{D6a}$, —SC(=S)N(R$^{D6b}$)$_2$, —S(=O)R$^{D6a}$, —SO$_2$R$^{D6a}$, —NR$^{D6b}$SO$_2$R$^{D6a}$, —SO$_2$N(R$^{D6b}$)$_2$, —CN, —SCN, and —NO$_2$, wherein each occurrence of R$^{D6a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, and each occurrence of R$^{D6b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two R$^{D6b}$ groups are joined to form an optionally substituted heterocyclic ring; and w is 0, 1, 2, or 3.

In certain embodiments of Formula (D-IV), wherein w is 1, provided is a compound of any of the formulae:

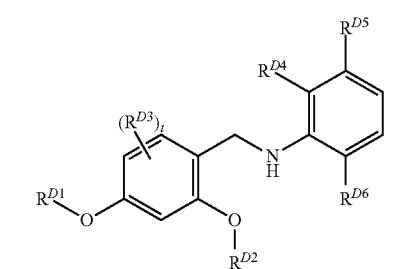

(D-IV-a)

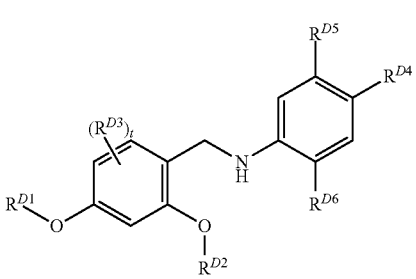

(D-IV-b)

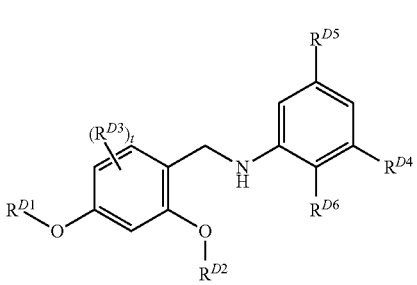

(D-IV-c)

and pharmaceutically acceptable salts, solvates, hydrates, polymorphs, co-crystals, tautomers, stereoisomers, isotopically labeled derivatives, and prodrugs thereof, wherein R$^{D1}$, R$^{D2}$, R$^{D3}$, R$^{D4}$, R$^{D5}$, R$^{D6}$, and t are as defined herein.

In certain embodiments of Formula (D-IV), or a pharmaceutically acceptable salt thereof, R$^{D5}$, R$^{D6}$, or both are C$_{1-6}$ alkyl. In certain embodiments of Formula (D-IV), or a pharmaceutically acceptable salt thereof, R$^{D5}$, R$^{D6}$, or both are methyl. In certain embodiments of Formula (D-IV), or a pharmaceutically acceptable salt thereof, R$^{D5}$, R$^{D6}$, or both are ethyl. In certain embodiments of Formula (D-IV), or a pharmaceutically acceptable salt thereof, R$^{D5}$, R$^{D6}$, or both are propyl. In certain embodiments of Formula (D-IV), or a pharmaceutically acceptable salt thereof, R$^{D5}$, R$^{D6}$, or both are butyl.

In certain embodiments, provided is a compound of Formula (D-V):

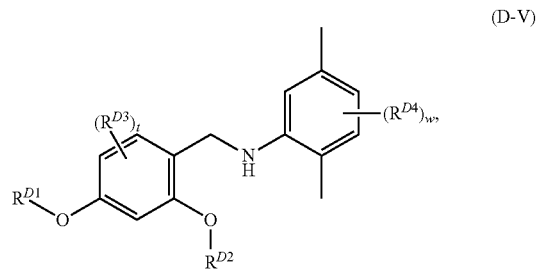

(D-V)

and pharmaceutically acceptable salts, solvates, hydrates, polymorphs, co-crystals, tautomers, stereoisomers, isotopically labeled derivatives, and prodrugs thereof, wherein R$^{D1}$, R$^{D2}$, R$^{D3}$, R$^{D4}$, t and w are as defined herein.

In certain embodiments of Formula (D-V), and pharmaceutically acceptable salts, solvates, hydrates, polymorphs, co-crystals, tautomers, stereoisomers, isotopically labeled derivatives, and prodrugs thereof, wherein w is 1, provided is a compound of any of the formulae:

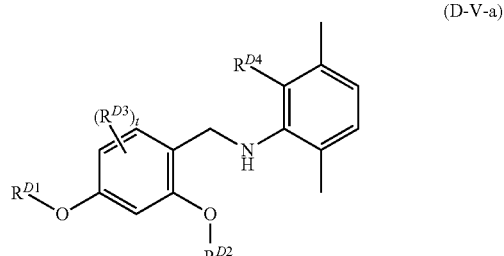

(D-V-a)

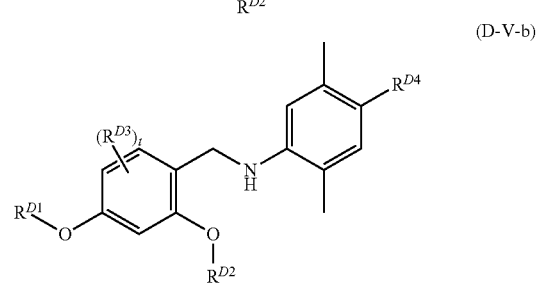

(D-V-b)

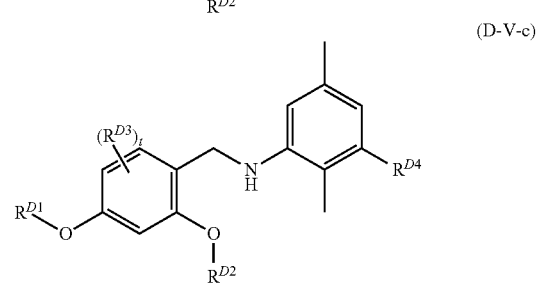

(D-V-c)

and pharmaceutically acceptable salts, solvates, hydrates, polymorphs, co-crystals, tautomers, stereoisomers, isotopically labeled derivatives, and prodrugs thereof, wherein R$^{D1}$, R$^{D2}$, R$^{D3}$, R$^{D4}$, and t are as defined herein.

In certain embodiments, provided is a compound of Formula (D-VI):

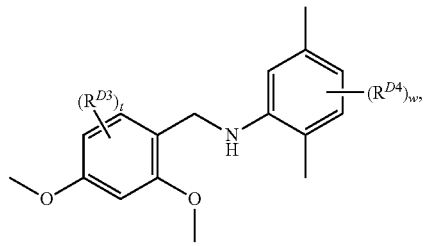

(D-VI)

and pharmaceutically acceptable salts, solvates, hydrates, polymorphs, co-crystals, tautomers, stereoisomers, isotopically labeled derivatives, and prodrugs thereof, wherein $R^{D3}$, $R^{D4}$, t, and w are as defined herein.

In certain embodiments, the compound of Formula (D) is not of the formula:

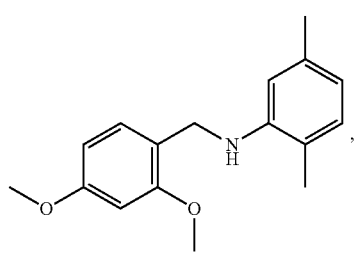

(DAC-012)

or a pharmaceutically acceptable salt thereof.

Pharmaceutical Compositions, Kits, and Administration

The present invention provides pharmaceutical compositions comprising a compound of the present invention, e.g., a compound of any one of the Formulae (A), (B), (C), and (D), and pharmaceutically acceptable salts, solvates, hydrates, polymorphs, co-crystals, tautomers, stereoisomers, isotopically labeled derivatives, and prodrugs thereof, as described herein, and a pharmaceutically acceptable excipient. In certain embodiments, the compound of the present invention or a pharmaceutically acceptable salt thereof is provided in an effective amount in the pharmaceutical composition. In certain embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, anti-cancer agents, anti-diabetic agents, anti-inflammatory agents, immunosuppressant agents, and a pain-relieving agent. Therapeutically active agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Thus, in one aspect, provided is a pharmaceutical composition comprising a compound of any one of the Formulae (A), (B), (C), and (D), and pharmaceutically acceptable salts, solvates, hydrates, polymorphs, co-crystals, tautomers, stereoisomers, isotopically labeled derivatives, and prodrugs thereof, and a pharmaceutically acceptable excipient. In certain embodiments, provided is a composition described herein, wherein the compound or pharmaceutically acceptable salt thereof is provided in an effective amount.

In another aspect, provided is a kit for treating or preventing a neurological disorder comprising:

a first container comprising an HDAC (histone deacetylase) activator; and instructions for administering the HDAC activator to a subject to treat a neurological disorder. In certain embodiments, the HDAC activator is a class I HDAC activator. In certain embodiments, the class I HDAC activator is an HDAC1 (histone deacetylase 1) activator.

In certain embodiments, provided is a kit for treating a neurological disorder comprising:

a first container comprising the compound of Formula (DAC-001):

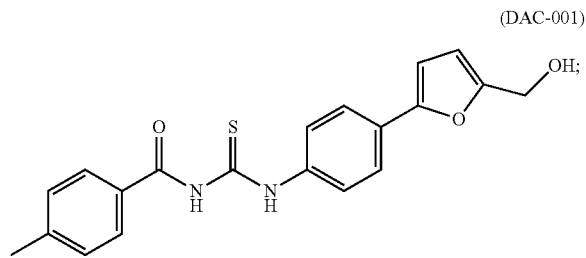 [SMILES: Cc1ccc(C(=O)NC(=S)Nc2ccc(-c3ccc(CO)o3)cc2)cc1]

(DAC-001)

and instructions for administering the compound of Formula (DAC-001) to a subject to treat a neurological disorder.

In certain embodiments, provided is a kit for treating a neurological disorder comprising:

a first container comprising the compound of Formula (DAC-002):

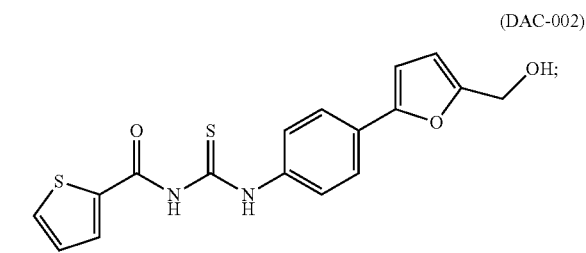 [SMILES: O=C(NC(=S)Nc1ccc(-c2ccc(CO)o2)cc1)c1cccs1]

(DAC-002)

and instructions for administering the compound of Formula (DAC-002) to a subject to treat a neurological disorder.

In certain embodiments, provided is a kit for treating a neurological disorder comprising:

a first container comprising the compound of Formula (DAC-009):

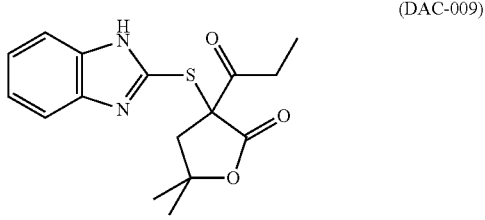 [SMILES: CCC(=O)C1(Sc2nc3ccccc3[nH]2)CC(C)(C)OC1=O]

(DAC-009)

or a pharmaceutically acceptable salt thereof; and instructions for administering the compound of Formula (DAC-009) to a subject to treat a neurological disorder.

In certain embodiments, provided is a kit for treating a neurological disorder comprising:

a first container comprising the compound of Formula (DAC-003):

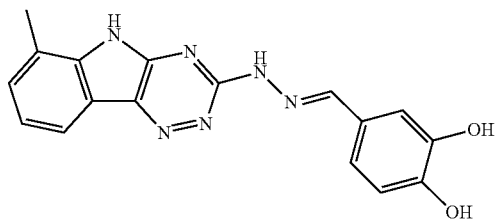

(DAC-003)

or a pharmaceutically acceptable salt thereof; and instructions for administering the compound of Formula (DAC-003) to a subject to treat a neurological disorder.

In certain embodiments, provided is a kit for treating a neurological disorder comprising:

a first container comprising the compound of Formula (DAC-012):

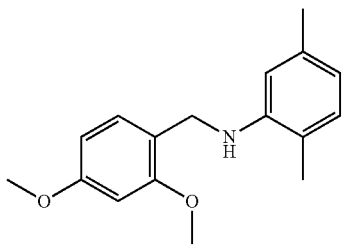

(DAC-012)

or a pharmaceutically acceptable salt thereof; and instructions for administering the compound of Formula (DAC-012) to a subject to treat a neurological disorder.

In certain embodiments, provided is a kit for treating a neurological disorder comprising:

a first container comprising a compound selected from the group of compounds consisting of the compounds of the Formulae (A), (B), (C), and (D), or a pharmaceutically acceptable salt thereof; and instructions for administering the compound selected in the previous step to a subject to treat a neurological disorder.

Methods of Treatment

In one aspect, the invention provides methods and compositions for the treatment or prevention of neurological disorders. In some embodiments, neurological disorders are treated by decreasing the amount of DNA damage within the neuronal cell. In some embodiments, neurological disorders are treated by increasing HDAC activity within the neuronal cell. In some embodiments, neurological disorders are treated by decreasing histone acetyl transferase activity within the neuronal cell. In some embodiments, neurological disorders are treated by increasing the activity of class I histone deacetylases. In some embodiments, neurological disorders are treated by increasing the activity of class I HDAC. In some embodiments, neurological disorders are treated by increasing the activity of HDAC1. In some embodiments, neurological disorders are treated by increasing the activity of HDAC2. In some embodiments, neurological disorders are treated by increasing the activity of HDAC3. In some embodiments, neurological disorders are treated by increasing the activity of HDAC8.

Regulating histone acetylation is an integral aspect of chromatin modulation and gene regulation that plays a critical role in many biological processes including cell proliferation and differentiation (Roth et al., *Annu. Rev. Biochem.* (2001) 70:81-120). Recent reports have detailed the importance of histone acetylation in CNS functions such as neuronal differentiation, memory formation, drug addiction, and depression (Citrome, *Psychopharmacol. Bull.* (2003) 37 Suppl. 2:74-88; Johannessen et al., *CNS Drug Rev.* (2003) 9:199-216; Tsankova et al., *Nature Neuroscience* (2006) 9:519-525). Histone deacetylases remove acetyl groups from histones, resulting in increased chromatin compaction and decreased accessibility to DNA for interacting molecules such as transcription factors (Cerna et al., *Curr. Top. Dev. Biol.* (2006) 73:173-204).

Of the HDACs, HDAC1 was the first protein identified to have histone-directed deacetylase activity (Taunton et al., *Science* (1996) 272:408-411; Vidal et al., *Mol. Cell Biol.* (1991) 11:6317-6327). HDAC1 plays important roles in regulating the cell cycle and is required in the transcriptional repression of cell cycle genes such as p21/WAF, E2F-1, and cyclins A and E (Brehm et al., *Nature* (1998) 391:597-601; Iavarone et al., *Mol. Cell Biol.* (1999) 19:916-922; Lagger et al., *Embo. J.* (2002) 21:2672-2681; Rayman et al., *Genes Dev.* (2002) 16:933-947; Stadler et al., *Dev. Dyn.* (2005) 233:883-889; Stiegler et al., *Cancer Res.* (1998) 58:5049-5052). The association of HDAC1 with promotor regions of specific genes is linked to their transcriptional repression (Brehm et al., *Nature* (1998) 391:597-601; Gui et al., *Proc. Natl. Acad. Sci. USA* (2004) 101:1241-1246; Iavarone et al., *Mol. Cell Biol.* (1999) 19:916-922; Rayman et al., *Genes Dev.* (2002) 16:933-947).

It has been found that agents that increase HDAC1 activity are neuroprotective (PCT Patent Application Publication No. WO 2010/011318). Those agents may serve for the treatment of neurological disorders, including Alzheimer's disease, Parkinson's disease, Huntington's disease, amyotrophic lateral sclerosis (ALS), ischemic brain damage, traumatic brain injury, stroke, frontal temporal dementia, Pick's disease, corticobasal degeneration, supra cerebral palsy, prion diseases (e.g., Creutzfeldt-Jakob disease, Gerstmann-Straussler-Scheinker syndrome, Fatal Familial Insomnia, and Kuru), Nieman Pick type C, spinal cerebellar ataxia, spinal muscular dystrophy, ataxia telangiectasia, hippocampal sclerosis, Cockayne syndrome, Werner syndrome, xeroderma pigmentosaum, and Bloom syndrome.

Nucleosomes, the primary scaffold of chromatin folding, are dynamic macromolecular structures, influencing chromatin solution conformations. The nucleosome core is made up of histone proteins, H2A, H2B, H3, and H4. Histone acetylation causes nucleosomes and nucleosomal arrangements to behave with altered biophysical properties. The balance between activities of histone acetyl transferases (HAT) and histone deacetylases determines the level of histone acetylation. Acetylated histones cause relaxation of chromatin and activation of gene transcription, whereas deacetylated chromatin generally is transcriptionally inactive.

In some embodiments, neurological disorders are treated by decreasing histone acetylation by the administration of histone acetylase activators. In some embodiments, neurological disorders are treated by decreasing histone acetylation by methods other than increasing HDAC activity. Methods for decreasing histone acetylation, by a method other than a classic HDAC activator include, but are not limited to, the administration of nucleic acid molecule inhibitors such as antisense and RNAi molecules which reduce the expression of histone acetyl transferases and the administration of histone acetyl transferase inhibitors. Histone acetyl transferase inhibitors are known in the art (Eliseeva et al., *Mol. Cancer Ther.* (2007) 6:2391-98). The invention embraces methods that regulate the function of any protein involved with histone modification, function and regulation.

In some embodiments, neurological disorders are treated by protecting cells from DNA damage by increasing the histone deacetylation activity within the cell. Protection from DNA damage includes both a decrease in the current level of DNA damage accumulated within the cell, or a decrease in the rate of DNA damage acquired by the cell, including DNA damage acquired during exposure of the cell to DNA damaging events, such as exposure to DNA damaging agents, including radiation, and events that lead to increased oxidative stress. Increased deacetylase activity can protect against any form of DNA damage, including base modifications, DNA single strand breaks, and DNA double strand breaks. DNA double strand breaks are potentially the most damaging to the cell, and other forms of DNA damage can be turned into DNA double strand breaks by the action of DNA repair enzymes and other cellular processes. DNA damage, including DNA double strand breaks, can accumulate in both actively dividing and non-dividing cells. In actively dividing cells, DNA double strand breaks may inhibit the replication machinery, while in both actively dividing and non-dividing cells the transcription machinery may be inhibited by DNA double strand breaks. In addition, DNA double strand breaks may initiate potentially damaging recombination events. Thus, increased deacetylase activity may be protective in any cell type, including dividing and non-dividing cells. In some embodiments, increased deacetylase activity is protective in neuronal cells. In some embodiments, increased deacetylase activity is induced in cells that are susceptible to acquiring DNA damage, or cells that will be subjected to a DNA damage inducing event. For instance, histone deacetylase activity may be increased in cells or tissue in a subject that need to be protected when a DNA damaging agent is administered throughout the body (for instance, during chemotherapy). In some embodiments, neuroprotection is provided by increasing the histone deacetylation activity within a neuronal cell. In some embodiments, neuroprotection is provided by decreasing the histone acetyl transferase activity within a neuronal cell.

The invention embraces any method of increasing deacetylase activity. In some embodiments, deacetylase activity is increased by increasing the activity of class I HDAC. In some embodiments, deacetylase activity is increased by increasing the activity of HDAC1. In some embodiments, deacetylase activity is increased by increasing the activity of HDAC2. In some embodiments, deacetylase activity is increased by increasing the activity of HDAC3. In some embodiments, deacetylase activity is increased by increasing the activity of HDAC8. In some embodiments, deacetylase activity is increased by adding an HDAC activator to the cell. In some embodiments, the HDAC activator is a class I HDAC activator. In some embodiments, the HDAC activator is an HDAC1 activator. In some embodiments, the HDAC activator is an HDAC2 activator. In some embodiments, the HDAC activator is an HDAC3 activator. In some embodiments, the HDAC activator is an HDAC8 activator. In some embodiments, HDAC activity is increased by increasing the expression level of one or more HDACs. In some embodiments, HDAC activity is increased by selectively increasing the expression level of one or more HDACs relative to one or more HDACs. In some embodiments, HDAC activity is increased by selectively increasing the expression level of one or more HDACs by 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% to 60%, 60% to 70%, 70% to 80%, 80% to 90%, or 90% to 100% relative to one or more HDACs. In some embodiments, HDAC activity is increased by selectively increasing the expression level of one or more HDACs by 100% to 200%, 200% to 300%, 300% to 500%, 500% to 1000%, 1000% to 10000%, or 10000% to 100000% relative to one or more other HDACs. In some embodiments, the expression level is increased by increasing the level and/or activity of transcription factors that act on a specific gene encoding a histone deacetylase. In some embodiments, the activity is increased by decreasing the activity of repressor elements. In some embodiments, deacetylase activity within a cell or subject is increased by administering histone deacetylase protein to the cell or subject. In some embodiments, the activity is increased by inactivating or sequestering an agent that acts as an inhibitor on a HDAC suppressor pathway.

An "HDAC activator" as defined herein is any compound that results in an increase in the level of HDAC activity. Any increase in enzymatic function of an HDAC is embraced by the invention. In some embodiments, the activity increase of HDAC is an increase in HDAC deacetylase activity. In some embodiments, the activity increase of HDAC is an increase in HDAC esterase activity. HDAC activity corresponds to the level of histone deacetylase activity of the HDAC. One of ordinary skill in the art can select suitable compounds on the basis of the known structures of histone deacetylases. Examples of such compounds are peptides, nucleic acids expressing such peptides, small molecules, etc., each of which can be naturally occurring molecules, synthetic molecules, and/or FDA approved molecules, that specifically react with the histone deacetylase and increase its activity.

In certain embodiments, the HDAC activator is a naturally occurring compound or a compound that has been synthesized, or a pharmaceutically acceptable salt thereof, such as a compound of the Formula (DAC-001), (DAC-002), (DAC-003), (DAC-009), or (DAC-012), or pharmaceutically acceptable salt thereof.

In certain embodiments, the HDAC activator is a compound of Formula (A), (B), (C), or (D), or pharmaceutically acceptable salt thereof.

In certain embodiments, provided is a method for treating or preventing a neurological disorder in a subject, the method comprising administering to a subject in need of treatment for a neurological disorder a therapeutically effective amount of the compound of Formula (DAC-001), or a pharmaceutically acceptable salt thereof.

In certain embodiments, provided is a method for treating or preventing a neurological disorder in a subject, the method comprising administering to a subject in need of treatment for a neurological disorder a therapeutically effective amount of the compound of Formula (DAC-002), or a pharmaceutically acceptable salt thereof.

In certain embodiments, provided is a method for treating or preventing a neurological disorder in a subject, the method comprising administering to a subject in need of treatment for a neurological disorder a therapeutically effective amount of the compound of Formula (DAC-009), or a pharmaceutically acceptable salt thereof.

In certain embodiments, provided is a method for treating or preventing a neurological disorder in a subject, the method comprising administering to a subject in need of treatment for a neurological disorder a therapeutically effective amount of the compound of Formula (DAC-003), or a pharmaceutically acceptable salt thereof.

In certain embodiments, provided is a method for treating or preventing a neurological disorder in a subject, the method comprising administering to a subject in need of treatment for a neurological disorder a therapeutically effective amount of the compound of Formula (DAC-012), or a pharmaceutically acceptable salt thereof.

In certain embodiments, provided is a method for treating or preventing a neurological disorder in a subject, the method comprising administering to a subject in need of treatment for a neurological disorder a therapeutically effective amount of a compound of Formula (A), or a pharmaceutically acceptable salt thereof.

In certain embodiments, provided is a method for treating or preventing a neurological disorder in a subject, the method comprising administering to a subject in need of treatment for a neurological disorder a therapeutically effective amount of a compound of Formula (B), or a pharmaceutically acceptable salt thereof.

In certain embodiments, provided is a method for treating or preventing a neurological disorder in a subject, the method comprising administering to a subject in need of treatment for a neurological disorder a therapeutically effective amount of a compound of Formula (C), or a pharmaceutically acceptable salt thereof.

In certain embodiments, provided is a method for treating or preventing a neurological disorder in a subject, the method comprising administering to a subject in need of treatment for a neurological disorder a therapeutically effective amount of a compound of Formula (D), or a pharmaceutically acceptable salt thereof.

In certain embodiments, the neurological disorder being treated or prevented is Alzheimer's disease.

In certain embodiments, the neurological disorder being treated or prevented is Parkinson's disease.

In certain embodiments, the neurological disorder being treated or prevented is Huntington's disease.

In certain embodiments, the neurological disorder being treated or prevented is ALS (amyotrophic lateral sclerosis).

In certain embodiments, the neurological disorder being treated or prevented is traumatic brain injury.

In certain embodiments, the neurological disorder being treated or prevented is ischemic brain injury.

In certain embodiments, the neurological disorder being treated or prevented is stroke.

In certain embodiments, the neurological disorder being treated or prevented is frontal temporal dementia.

In certain embodiments, the neurological disorder being treated or prevented is Pick's disease.

In certain embodiments, the neurological disorder being treated or prevented is corticobasal degeneration.

In certain embodiments, the neurological disorder being treated or prevented is supra cerebral palsy.

In certain embodiments, the neurological disorder being treated or prevented is prion diseases (e.g., Creutzfeldt-Jakob disease, Gerstmann-Straussler-Scheinker syndrome, Fatal Familial Insomnia, and Kuru).

In certain embodiments, the neurological disorder being treated or prevented is Nieman Pick type C.

In certain embodiments, the neurological disorder being treated or prevented is spinal cerebellar ataxia.

In certain embodiments, the neurological disorder being treated or prevented is spinal muscular dystrophy.

In certain embodiments, the neurological disorder being treated or prevented is ataxia telangiectasia.

In certain embodiments, the neurological disorder being treated or prevented is hippocampal sclerosis.

In certain embodiments, the neurological disorder being treated or prevented is Cockayne syndrome.

In certain embodiments, the neurological disorder being treated or prevented is Werner syndrome.

In certain embodiments, the neurological disorder being treated or prevented is xeroderma pigmentosaum.

In certain embodiments, the neurological disorder being treated or prevented is Bloom syndrome.

EXAMPLES

In order that the invention described herein may be more fully understood, the following examples are set forth. It should be understood that these examples are for illustrative purposes only and are not to be construed as limiting this invention in any manner.

Example 1

Recombinant HDAC1 Expression, Purification, and Proteomic Analysis

Recombinant, full-length human HDAC1 (GenBank Accession No. NM_004964) with a C-terminal FLAG tag was produced by BPS Biosciences (San Diego, Calif.) using large-scale insect cell protein expression and purification in order to support a large-scale high-throughput screen (HTS).

To determine the quality of the protein preparation, and to confirm the existence of only HDAC1 as the only deacetylase in the preparation, NanoLC-MS/MS peptide sequencing technology was carried out by ProtTech, Inc (Norristown, Pa.). In brief, each protein gel band was destained, cleaned, and digested in-gel with sequencing grade modified trypsin obtained from Promega (Madison, Wis.). All other chemicals used in proteolytic digestion and HPLC were obtained from Sigma (St. Louis, Mo.). The resulting peptide mixture was analyzed using a LC-MS/MS system Thermo (Palo Alto, Calif.), in which a high pressure liquid chromatography (HPLC) with a 75 micrometer inner diameter reverse phase $C_{18}$ column was on-line coupled with a Quadrupole ion trap mass spectrometer. The mass spectrometric data acquired were used to search the most recent non-redundant protein database (downloaded from NCBI) with ProtTech's proprietary software suite.

For the two principle bands in the preparation isolated after SDS-PAGE, the first was identified as histone deacetylase 1 (HDAC1) with multiple peptides with a minor fraction of peptides from chaperonin TCP-1β4 that contains t-complex polypeptide 1 (TCP-1) beta subunit 4 (β4) from the Sf9 cells. The second predominant band was identified as heat shock cognate protein 70 (HSC70) from the Sf9 cells with a minor fraction of HDAC1. Interestingly, HSC70 has been reported to have ATPase function, which is common to many chromatin-remodeling complexes, and HSC70 has been shown to interact with Tau protein, a protein implicated in the pathology of Alzheimer's disease and other neurodegenerative disorders. An "ATPase" is an enzyme that uses ATP, i.e., adenosine triphosphate, as an energy source. In the case of TCP-1β4, these findings are of potential interest because, for HDAC3, a similar class I HDAC, the assembly of the SMRT-HDAC3 co-repressor complex requires the TCP-1 ring complex (Guenther et al., *Genes Dev.* (2002) 16:3130-35). It is thus possible that the regulation of HDAC1 conformation by TCP-1 ring complex is important for its deacetylase activity, which will be taken into consideration when the mechanisms of action of hits identified in the HTS are analyzed.

Example 2

Primary HDAC1 High-Throughput Screen

Using the microfluidics-based HDAC1 assay developed by Nanosyn (Durham, N.C.) at total of 47,144 compounds from a diverse, drug-like library were tested for their ability to enhance the deacetylase activity of recombinant HDAC1. Compounds were tested with a reaction time of 6 h with compounds tested at a single concentration (10 μM) in duplicate. As a positive control, the biflavonoid gingketin was chosen.

High-Throughput Screen Information 47,144 compounds were tested for their effect on the enzymatic activity of HDAC1. Compounds were tested in duplicate at 10 μM nominal final concentration in 384-well plate format. The reference activator compound, ginkgetin (50 μM), was included in duplicates in each HTS plate as a positive control condition. 24 negative control samples (DMSO only) were included in each plate to provide for the 0% activation baseline.

Screening Results

Within each HTS plate, the effect of individual compounds on the enzymatic activity of HDAC1 was calculated as % change in the conversion of the peptide substrate relative to the average substrate conversion value calculated across the 24 negative control samples.

A compounds was considered active if its effect (calculated as average of two duplicates) on the enzymatic activity of HDAC1 is above the 6σ standard deviations value of the assay, which is the commonly accepted statistical significance threshold for active compounds in HTS.

Figure 2A:
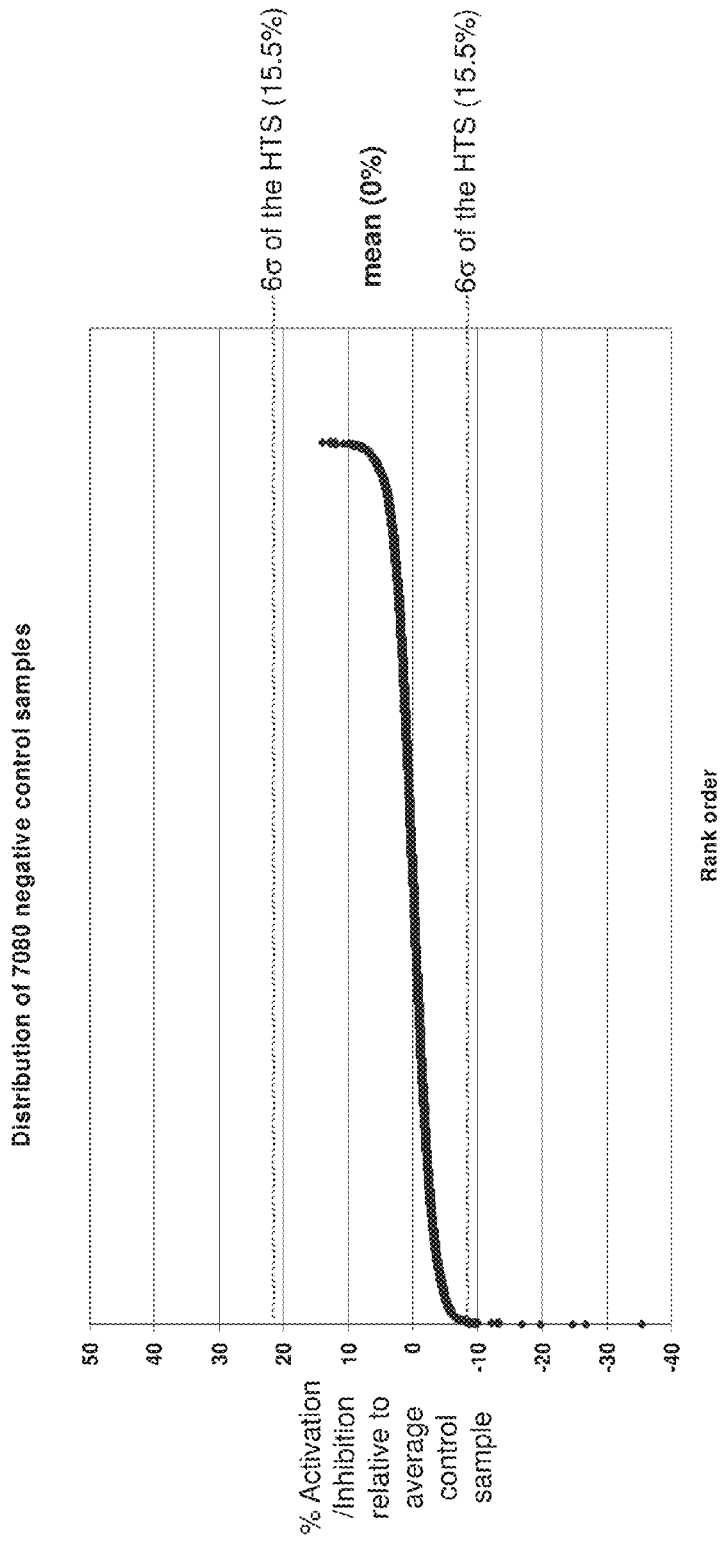
FIG. 2 shows HDAC1 microfluidics assay control data of 7,080 negative control samples (DMSO) (FIG. 2A) and 580 ginkgetin positive controls (50 µM) (FIG. 2B).
Figure 2B:
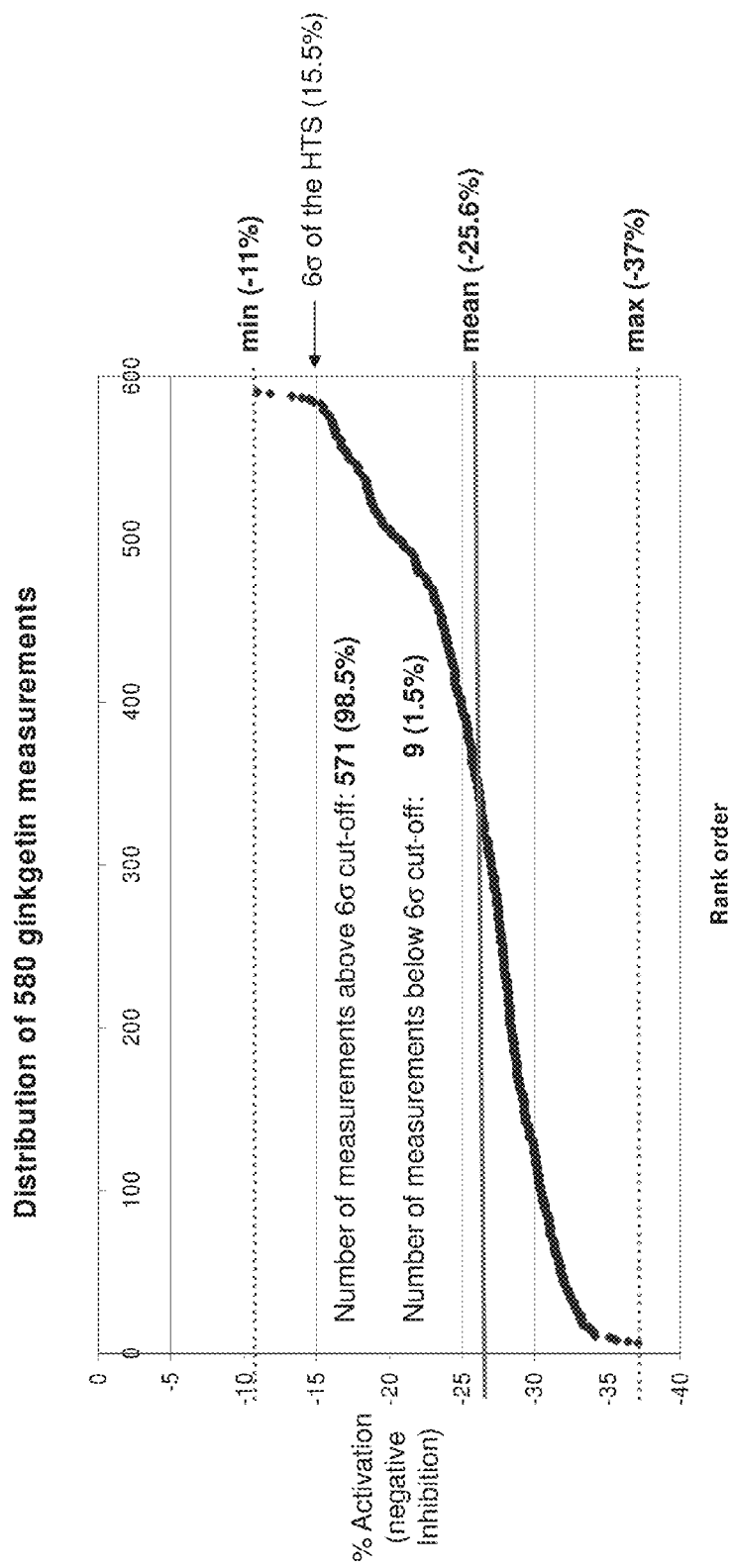

HDAC1 microfluidics assay control data of 7,080 negative control samples (DMSO) and 580 ginkgetin positive control samples (50 μM) are shown in FIG. 2A and FIG. 2B, respectively.

Figure 3A:
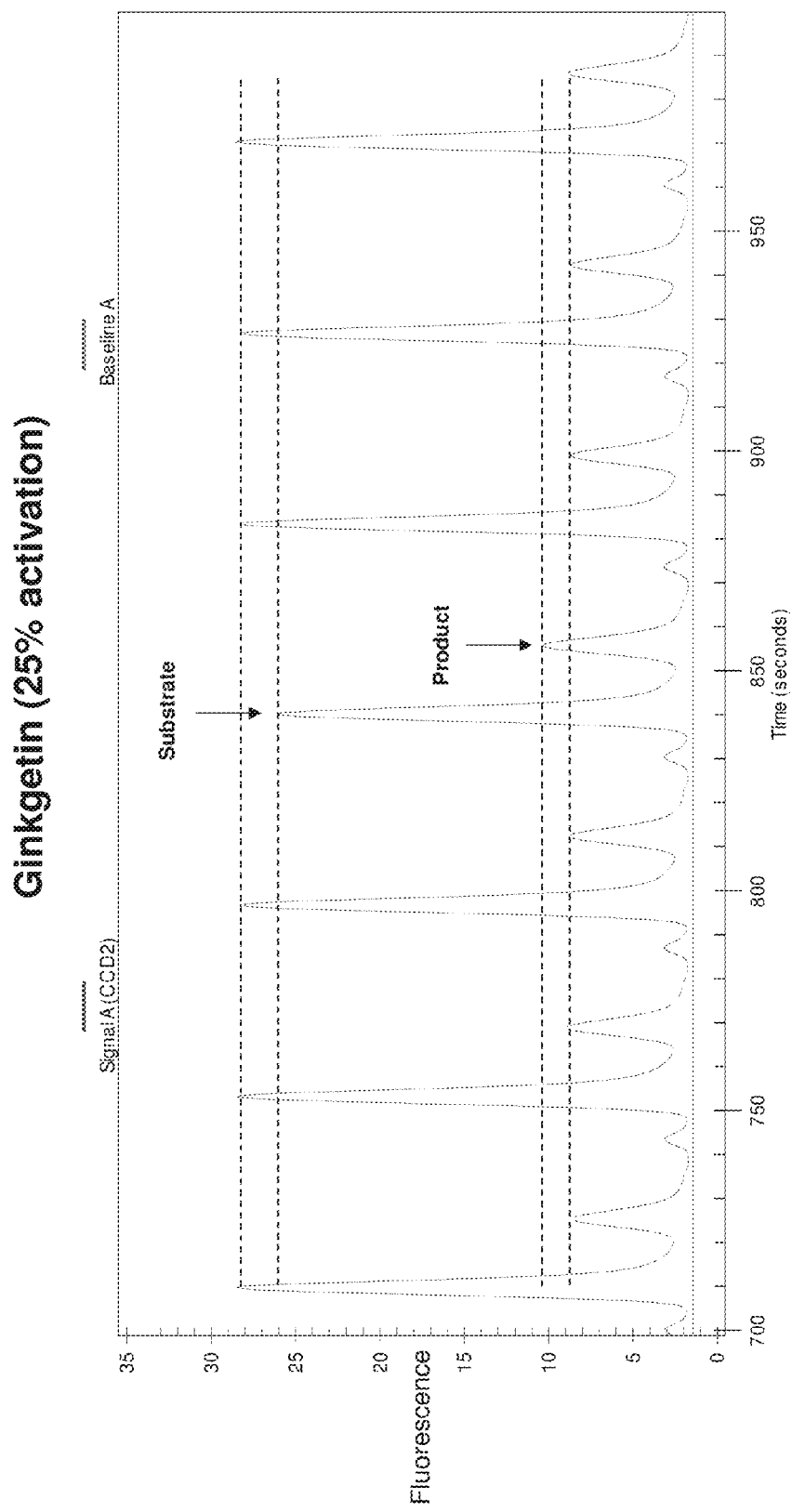
FIG. 3A depicts a primary microfluidic fluorescence reader trace for ginkgetin (positive control; for its structure, see FIG. 6A) showing increased conversion of the peptidic substrate FAM-TSRHKacKL to the deacetylated product FAM-TSRHKKL (illustrated with arrows).
Figure 3B:
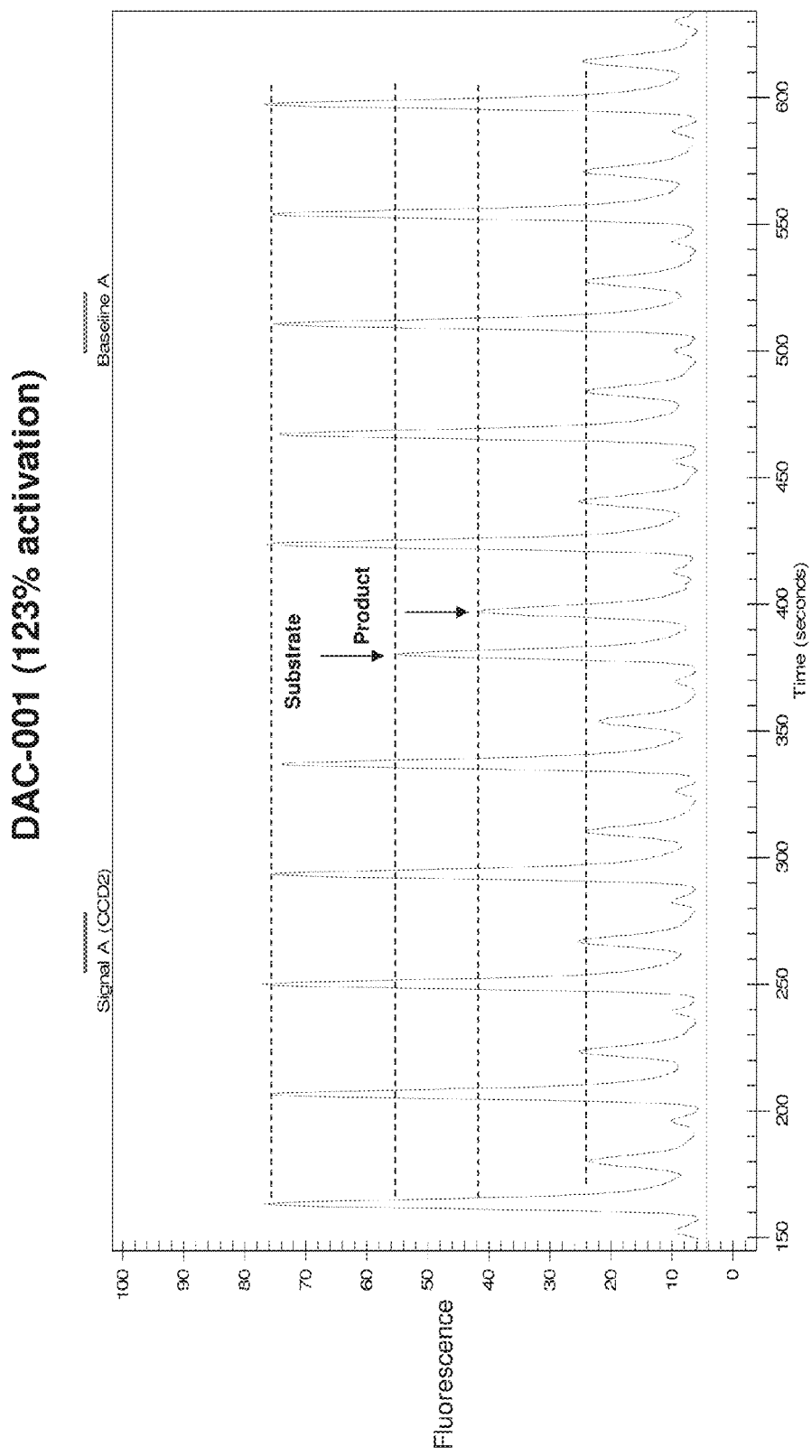
FIG. 3B depicts a primary microfluidic fluorescence reader trace for DAC-001, showing increased conversion of the peptidic substrate FAM-TSRHKacKL to the deacetylated product FAM-TSRHKKL (illustrated with arrows).

FIG. 3 includes HDAC1 HTS data. FIG. 3A depicts a primary microfluidic fluorescence reader trace for ginkgetin (positive control) showing increased conversion of the peptidic substrate FAM-TSRHKacKL to the deacetylated product FAM-TSRHKKL (illustrated with arrows). FIG. 3B depicts a primary microfluidic fluorescence reader trace for DAC-001, showing increased conversion of the peptide substrate FAM-TSRHKacKL to the deacetylated product FAM-TSRHKKL (illustrated with arrows).

HTS results are summarized in Table 1. A total of 21 hits, including DAC-001, DAC-002, DAC-003, DAC-009, and DAC-012, were identified by the HTS, the structures of which were determined using HPLC/UV/MS/ELSD analysis. Analysis of the structures of the hit compounds revealed multiple common structural frameworks suggesting the existence of a defined structure-activity-relationship for HDAC1 activation. All confirmed hits were re-ordered from commercial sources for further testing. Percent activation data are included in Table 2 for ginkgetin, DAC-001, DAC-002, DAC-003, DAC-009, and DAC-012.

TABLE 1

Summary of data obtained from high-thoughput screening

| | | |
|---|---|---|
| Total number of compounds screened | | 47,144 |
| 6σ value of the assay | | 15.5% activation |
| Positive control | Name | ginkgetin |
| | Total number of measurements | 580 |
| | Average effect | 26% activation (standard deviation: 4%) |
| | Measurements above 6σ | 571 (98.5% of total number of measurements) |
| | Measurements below 6σ | 9 (1.5% of total number of measurements) |
| Estimated probability that a potentially active compound has not been detected in at least one of the two replica samples | | <0.00023 |
| Total number of active compounds | | 21 (0.044% of total number of compounds screened) |

TABLE 2

Activation of HDAC1 by certain compounds in high-thoughput screening

| | Percent activation (%) | | |
|---|---|---|---|
| Compound ID | Replicate 1 | Replicate 2 | Average |
| ginkgetin | | | 25.6 ± 4.7 |
| DAC-001 | 122.6 | 138.4 | 130.5 |
| DAC-002 | 52.7 | 56.6 | 54.7 |
| DAC-003 | 24.2 | 24.9 | 24.6 |
| DAC-009 | 15.1 | 22.2 | 18.7 |
| DAC-012 | 17.5 | 17.9 | 17.7 |

Example 3

Secondary HDAC1 High-Throughput Screen

Figure 6A:
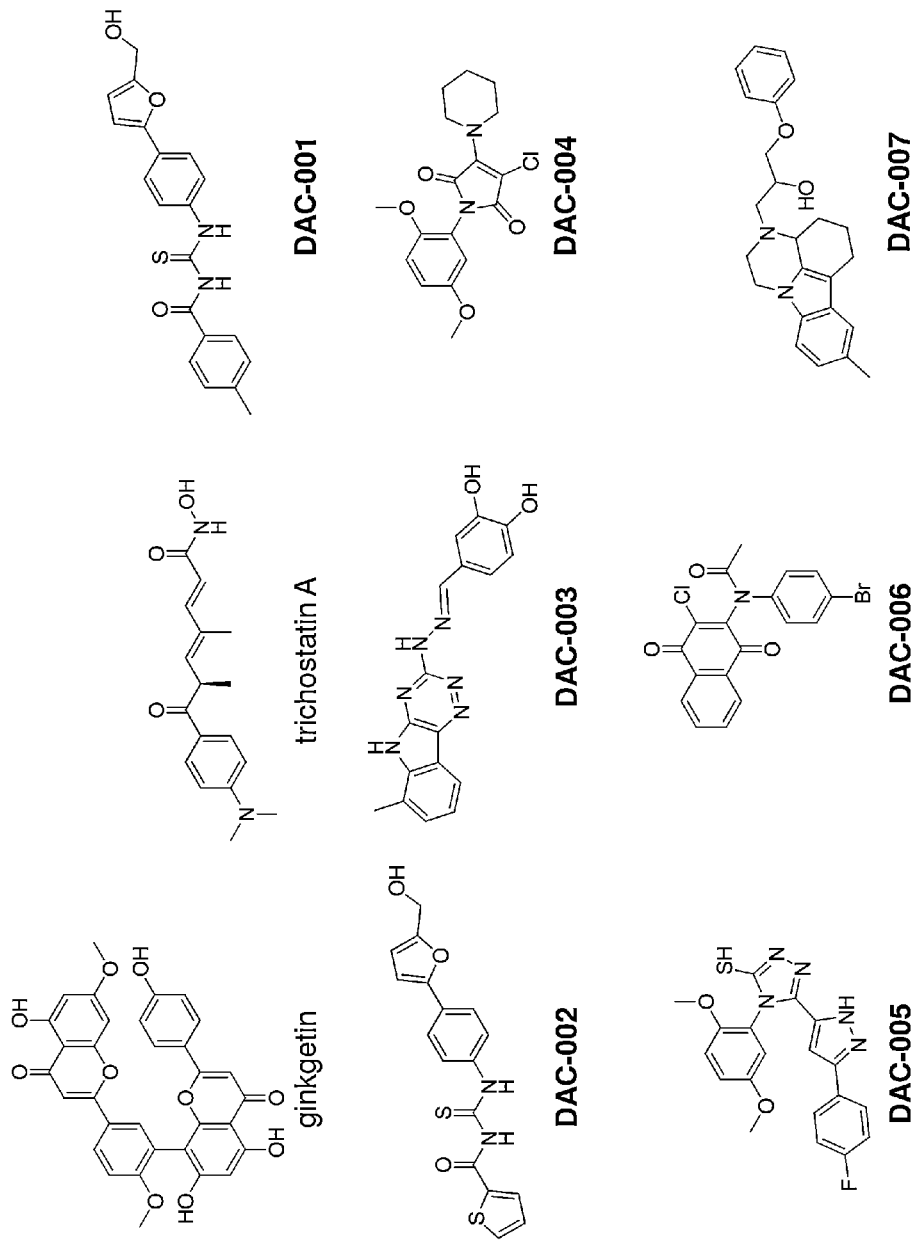
FIG. 6A-C shows the twenty-one (21) hit structures from the high throughput HDAC1 activator screen.
Figure 6B:
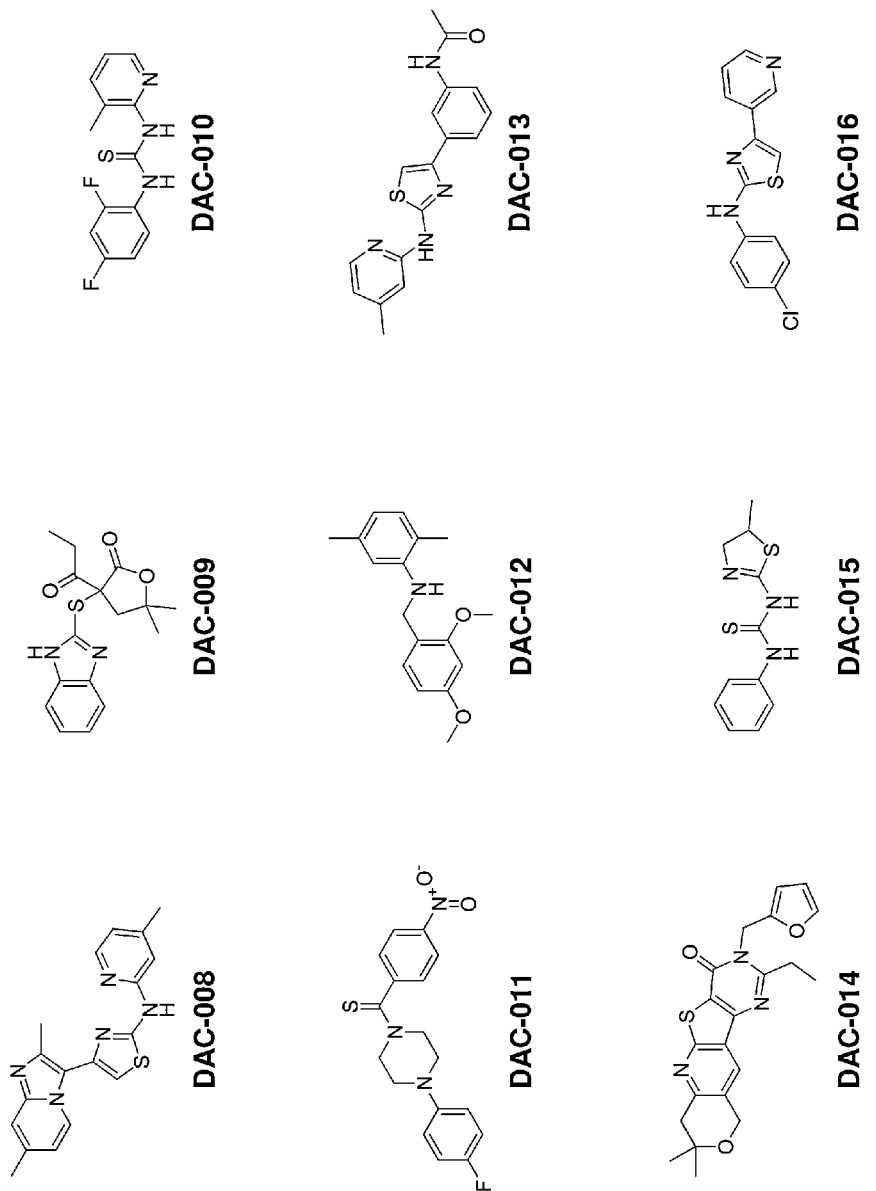
Figure 6C:
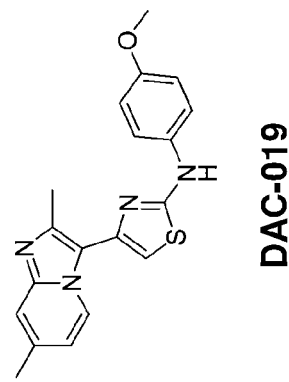
Figure 6C:
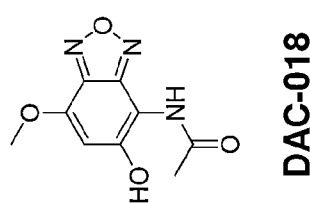
Figure 6C:
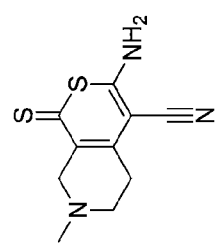
Figure 6C:
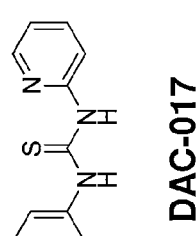
Figure 6C:
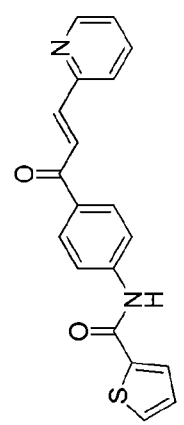

Based upon the results of the HDAC1 activator screen performed, a total of 21 compounds (for structures, see FIG. 6) were initially selected as hits due to their ability to enhance the deacetylase activity of recombinant HDAC1. Those hits, designated as "DACs" (deacetylase activating compounds), were measured using a microfluidics-based assay with an acetylated peptidic substrate (FAM-TSRHKacKL) over a reaction time of 6 h. The 21 HTS hits plus two controls: ginkgetin (an activator) and TSA (trichostatin A, an inhibitor; for its structure, see FIG. 6A) were retested in an 8-point dose response ranging from 50 μM to 0.02 μM. The positive control (ginkgetin) again demonstrated dose-dependent activation of HDAC1 (maximal effect of 20% and plateau at 10 μM), HDAC2 ($AC_{50}$=28 μM, maximal effect 165%) and HDAC3 (maximal effect 20% at 100 μM). TSA demonstrated dose dependent inhibition of all HDAC isoforms as expected.

Compounds were considered as confirmed hits if their $AC_{50}$ curve showed dose-dependent activation of the HDAC1 activity in microfluidics-based assay. The two most active HTS hits, compounds DAC-001 and DAC-002 demonstrated activation of up to 287% and 221% with $AC_{50}$ values of 4.05 µM and 8.31 µM, respectively. These data, included in Table 3, demonstrate the successful discovery of compounds that activate the deacetylase activity of HDAC1 in vitro.

TABLE 3

Activation of HDAC1 by certain comopunds in a microfluidics-based assay with an acetylated peptidic substrate (FAM-TSRHKacKL)

| Compound ID | Average activation % during HTS (10 µM) | Maximum activation % during dose response (50 µM maximum) |
|---|---|---|
| Ginkgetin | 25.6 | 23 |
| Trichostatin A | 0 | 0 |
| DAC-001 | 130.5 | 287 |
| DAC-002 | 54.7 | 221 |
| DAC-003 | 24.6 | 34 |
| DAC-009 | 18.7 | 12 |
| DAC-012 | 17.7 | 26 |

Microfluidics-based deacetylase assays were also performed using recombinant HDAC2, HDAC3, and HDAC8 to determine the selectivity of the compounds. Many of the confirmed compounds also activated HDAC2 isoform to a similar or even greater extent. Some compounds activated HDAC3 and inhibited the HDAC8 isoform.

Example 4

Characterization of HDAC1 Activators in Cellular Models of Neurodegeneration

Figure 4:
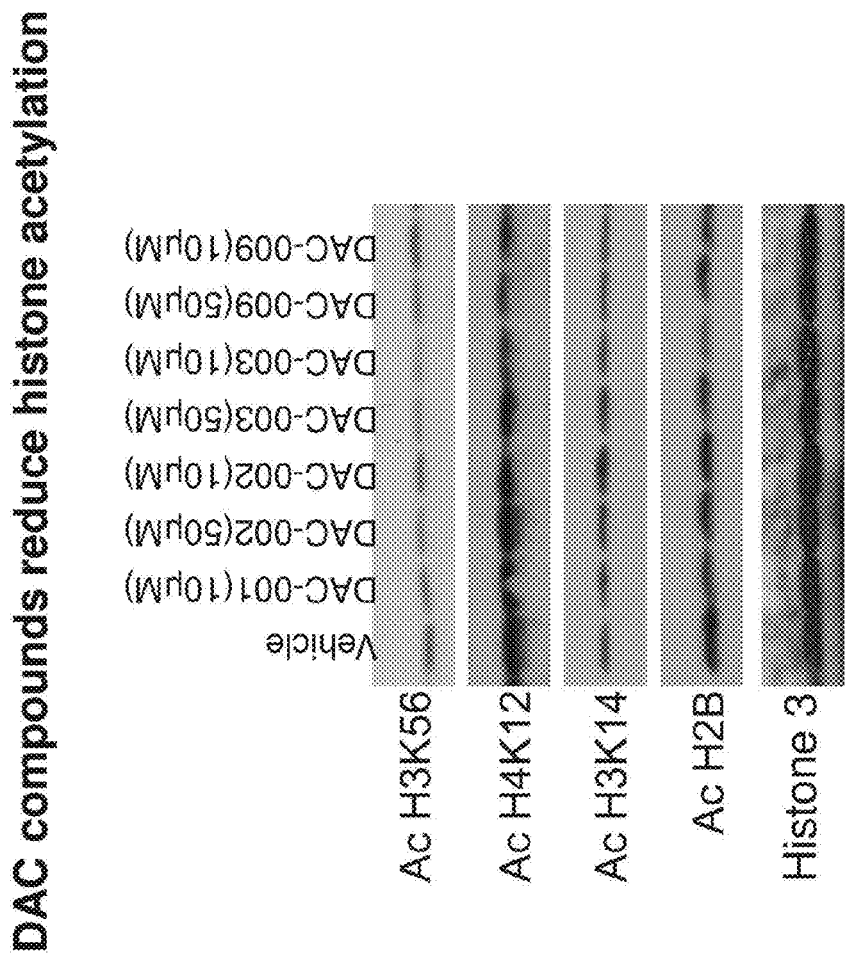
FIG. 4 shows that DAC compounds reduce histone acetylation. DAC compounds were added to HEK293T cells for 20 h. Vehicle was DMSO. Histones were acid-extracted and analyzed by Western blot for Ac-H3K56, Ac-H4K12, Ac-H3K14 and Ac-H2B. Histone 3 was used as the loading control.

Next, what was tested was whether a treatment of HDAC1 activators can increase HDAC1 enzymatic activity in cultured cells. Human HEK293T cells were treated with compounds at different concentrations (10 µM or 50 µM) for 20 h. Histone proteins were extracted, and Western blotting was used to analyze the acetylation of certain histone lysine residues known to be HDAC1 targets. Treatment with some compounds, such as DAC-001, DAC-002, DAC-003, and DAC-009, reduced the levels of Ac-H3K56, Ac-H3K14, Ac-H4K12 and Ac-H2B, indicating those compounds' ability to activate HDAC1 in cultured cells (FIG. 4).

HT-22 cells, a hippocampal neuron derived cell line, were used to model neurodegeneration. Two types of insults were used. Glutamate treatment induced oxidative stress by depleting glutathione. Etoposide, a topoisomerase II inhibitor, stressed cells through DNA damage. These two types of stresses have been documented in neurodegenerative diseases.

Figure 5A:
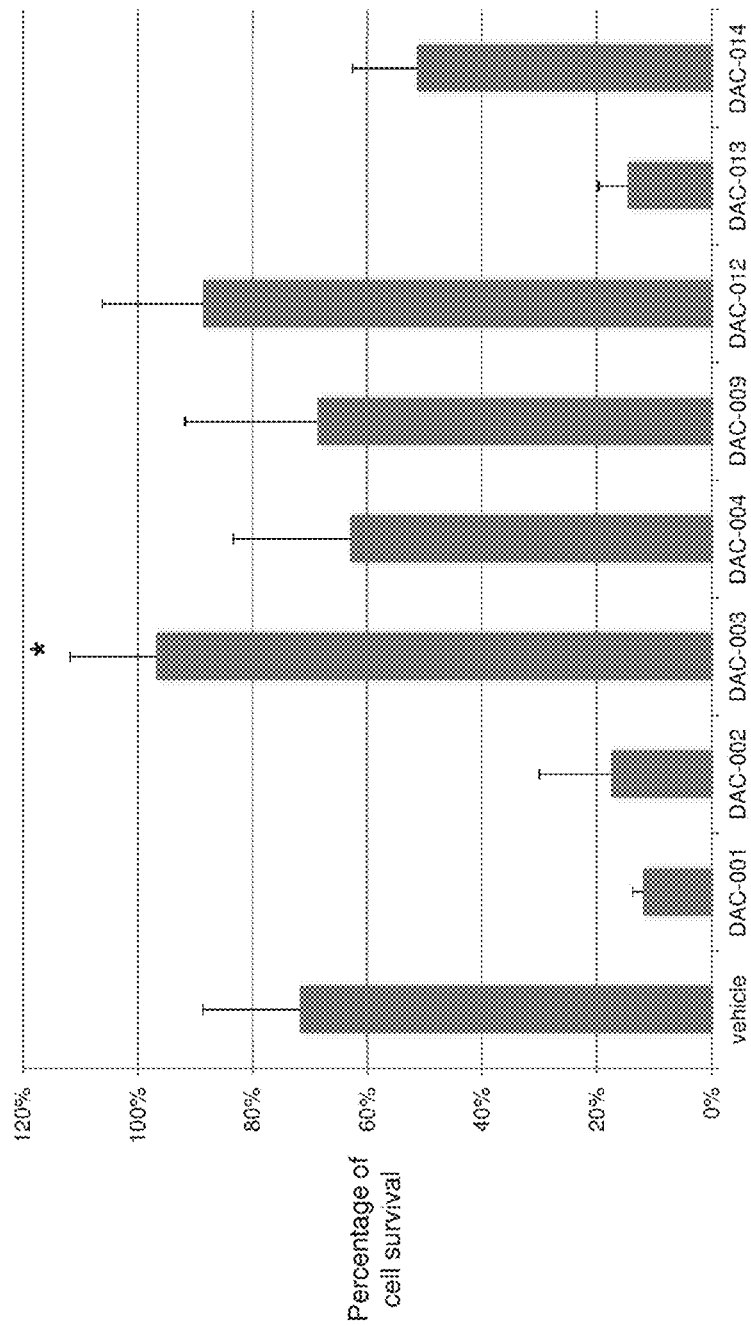
FIG. 5A shows that DAC compounds protect cells against oxidative stress. 10 μDAC-003 can significantly protect cells from oxidative insults (*p<0.05, compound versus vehicle treatment, student's t-test).

HT-22 cells were treated with compounds for 3 h prior to the addition of 2.5 mM glutamate. Cell viability was measured by CellTiter-Glo assays (Promega) (FIG. 5A). DAC-003 can significantly protect cells from oxidative stress (p<0.05, student's t-test). DAC-012 also showed a trend of protection.

Figure 5B:
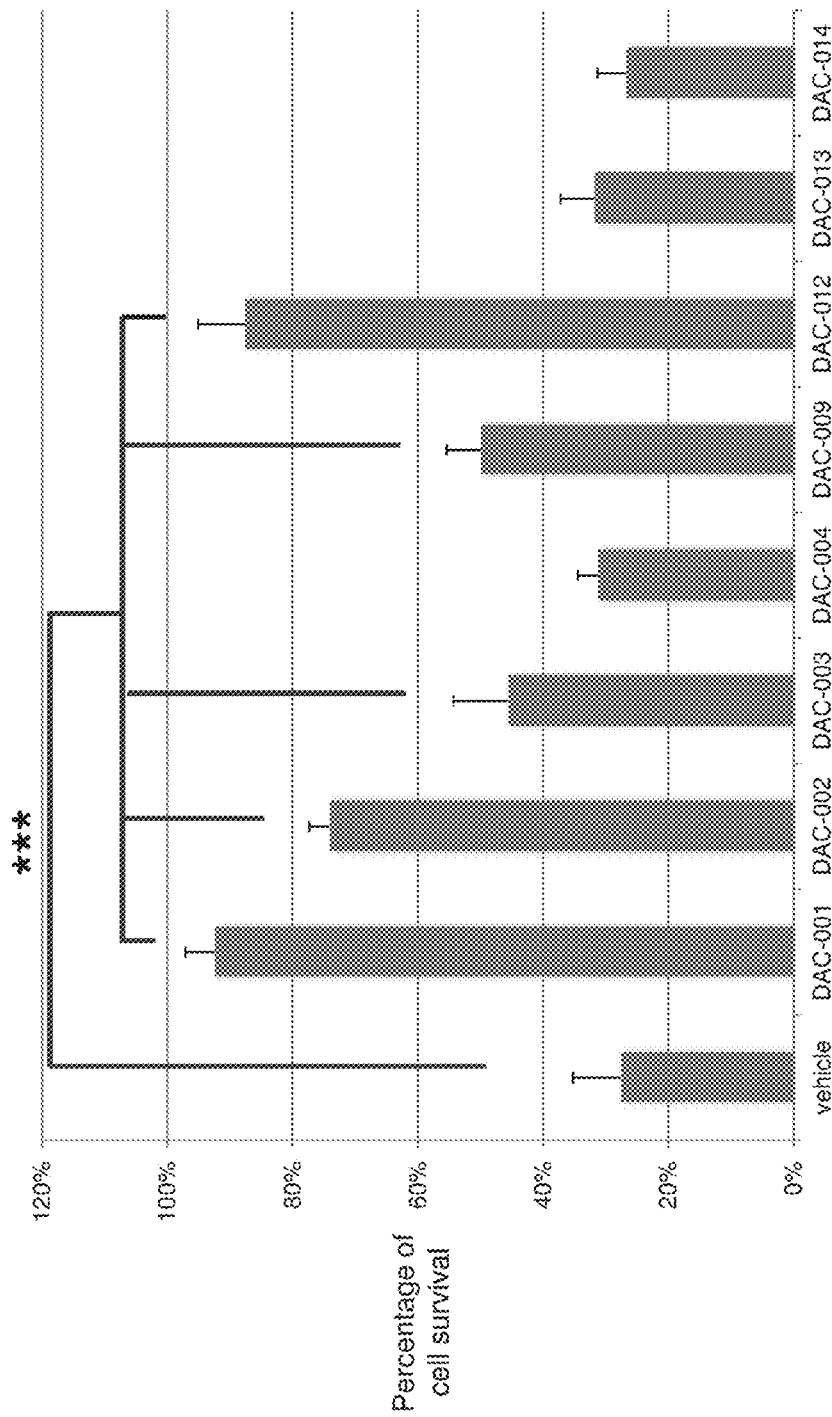
FIG. 5B shows that DAC compounds protect cells from DNA damage-induced stress. Cells were treated with etoposide, a topoisomerase II inhibitor, to generate DNA double strand breaks (DSB). It was found that DAC-001, DAC-002, DAC-003, DAC-009, and DAC-012 significantly protect cells from DSB-induced cell death (***p<0.001, compound versus vehicle treatment, student's t-test).

Similarly, HT-22 cells were pre-incubated with compounds (5 µM for DAC-001 and DAC-003; 10 µM for others) for 3 h. Then, 2 µM etoposide was added to the culture medium. Cell viability was measured 72 h later (FIG. 5B). Of the DAC compounds tested, DAC-001, DAC-002, DAC-003, DAC-009, and DAC-012 showed significant protection (p<0.001, student's t-test) against DNA damage stress. This result is consistent with previous findings that HDAC1 is directly involved in DNA damage repair, and that over-expression of HDAC1 is able to protect neurons from DNA damage.

Additionally, the safety of these compounds was tested in HT-22 cells (FIG. 5C). Cell survival was measured 72 h after compound treatment. Most compounds showed minimum effects (less than 10%) upon cell survival. This data also indicate that DAC compounds are less likely to affect cell proliferation.

The neuroprotection potential of the candidate compounds were also tested using a neuronal excitoxicity model. DIV 14 cortical neurons were treated with the compounds for 20 h. 50 µM glutamate was added to the culture 1 h before processing the samples for immunocytochemistry. MAP2 staining for the neuronal dendrites demonstrated that treatment with some of the compounds was able to protect neurons from excitotoxicity, as evidenced by their retention of dendrites. Ginkgetin was used as a positive control. Of the DAC compounds tested, DAC-002 and DAC-003 showed a trend of protection, while DAC-001 showed significant protection (p<0.01, student's t-test).

What is claimed is:

1. A compound of Formula (C-VII):

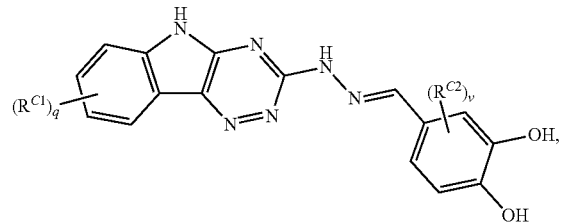

(C-VII)

or a pharmaceutically acceptable salt, tautomer, stereoisomer, or prodrug thereof, wherein:
each instance of $R^{C1}$ and $R^{C2}$ is independently selected from the group consisting of halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{C2a}$, $-N(R^{C2b})_2$, $-SR^{C2a}$, $-C(=O)R^{C2a}$, $-C(=O)OR^{C2a}$, $-C(=O)SR^{C2a}$, $-C(=O)N(R^{C2b})_2$, $-OC(=O)R^{C2a}$, $-OC(=O)OR^{C2a}$, $-OC(=O)SR^{C2a}$, $-OC(=O)N(R^{C2b})_2$, $-NR^{C2b}C(=O)R^{C2b}$, $-NR^{C2b}C(=O)OR^{C2a}$, $-NR^{C2b}C(=O)SR^{C2a}$, $-NR^{C2b}C(=O)N(R^{C2b})_2$, $-SC(=O)R^{C2a}$, $-SC(=O)OR^{C2a}$, $-SC(=O)SR^{C2a}$, $-SC(=O)N(R^{C2b})_2$, $-C(=NR^{C2b})R^{C2a}$, $-C(=NR^{C2b})OR^{C2a}$, $-C(=NR^{C2b})SR^{C2a}$, $-C(=NR^{C2b})N(R^{C2b})_2$, $-OC(=NR^{C2b})R^{C2a}$, $-OC(=NR^{C2b})OR^{C2a}$, $-OC(=NR^{C2b})SR^{C2a}$, $-OC(=NR^{C2b})N(R^{C2b})_2$, $-NR^{C2b}C(=NR^{C2b})R^{C2b}$, $-NR^{C2b}C(=NR^{C2b})OR^{C2a}$, $-NR^{C2b}C(=NR^{C2b})SR^{C2a}$, $-NR^{C2b}C(=NR^{C2b})N(R^{C2b})_2$, $-SC(=NR^{C2b})R^{C2a}$, $-SC(=NR^{C2b})OR^{C2a}$, $-SC(=NR^{C2b})SR^{C2a}$, $-SC(=NR^{C2b})N(R^{C2b})_2$, $-C(=S)R^{C2a}$, $-C(=S)OR^{C2a}$, $-C(=S)SR^{C2a}$, $-C(=S)N(R^{C2b})_2$, $-OC(=S)R^{C2a}$, $-OC(=S)OR^{C2a}$, $-OC(=S)SR^{C2a}$, $-OC(=S)N(R^{C2b})_2$, $-NR^{C2b}C(=S)R^{C2b}$, $-NR^{C2b}C(=S)OR^{C2a}$, $-NR^{C2b}C(=S)SR^{C2a}$, $-NR^{C2b}C(=S)N(R^{C2b})_2$, $-SC(=S)R^{C2a}$, $-SC(=S)OR^{C2a}$, $-SC(=S)SR^{C2a}$, —SC(=S)N(R$^{C2b}$)$_2$, —S(=O)R$^{C2a}$, —SO$_2$R$^{C2a}$, —NR$^{C2b}$SO$_2$R$^{C2a}$, —SO$_2$N(R$^{C2b}$)$_2$, —CN, —SCN, and —NO$_2$, wherein each occurrence of R$^{C2a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, and each occurrence of R$^{C2b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or two R$^{C2b}$ groups are joined to form an optionally substituted heterocyclic ring;

q is 0, 1, 2, 3, or 4; and v is 0, 1, 2, or 3;

provided that the compound is not of the formula:

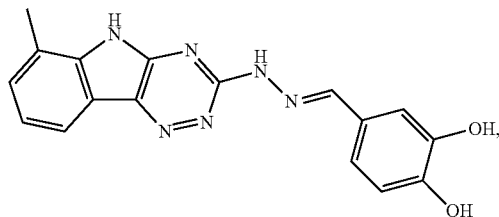 [SMILES: Cc1cccc2c1[nH]c1nc(N/N=C/c3ccc(O)c(O)c3)nnc12]

or a pharmaceutically acceptable salt thereof.

2. A pharmaceutical composition comprising a compound of claim 1, or a pharmaceutically acceptable salt thereof, and optionally a pharmaceutically acceptable excipient.

3. The compound of claim 1, wherein the compound is of the formula:

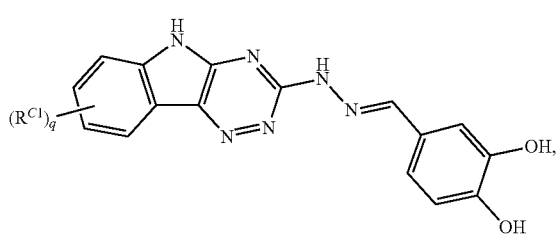

or a pharmaceutically acceptable salt, tautomer, stereoisomer, or prodrug thereof.

4. The compound of claim 1, wherein the compound is of the formula:

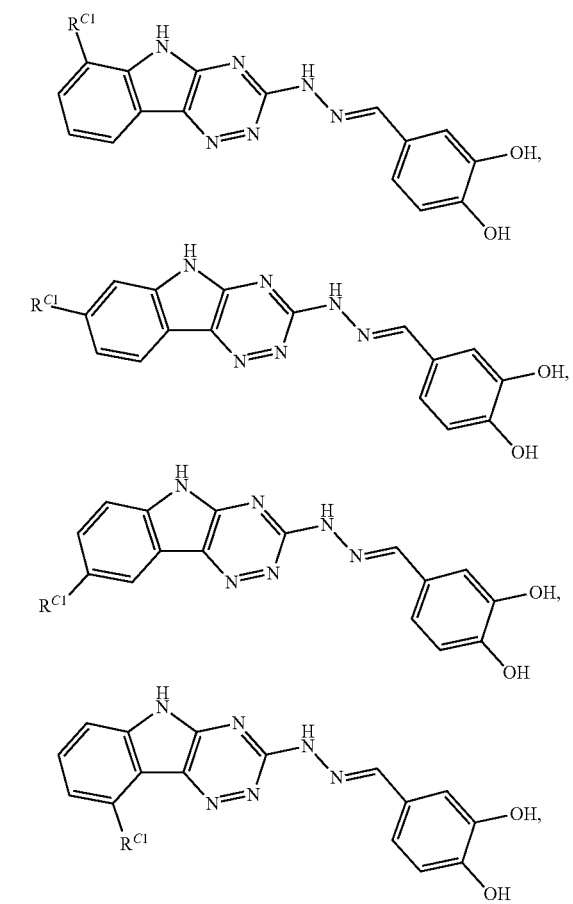

or a pharmaceutically acceptable salt, tautomer, stereoisomer, or prodrug thereof.

5. The compound of claim 1, wherein at least one R$^{C1}$ is C$_{1-6}$ alkyl.

6. The compound of claim 1, wherein at least one R$^{C1}$ is methyl.

7. The compound of claim 1, wherein q is 0.

8. The compound of claim 1, wherein q is 1.

9. The compound of claim 1, wherein at least one R$^{C2}$ is halogen.

10. The compound of claim 1, wherein at least one R$^{C2}$ is —OR$^{C2a}$.

11. The compound of claim 10, wherein R$^{C2a}$ is hydrogen.

12. The compound of claim 1, wherein v is 1.

* * * * *